(12) United States Patent  (10) Patent No.: US 8,795,166 B2
Roth et al.  (45) Date of Patent: *Aug. 5, 2014

(54) REMOTE TISSUE RETRACTION DEVICE

(75) Inventors: Alex T. Roth, Redwood city, CA (US); Craig Gerbi, Mountain View, CA (US); Andrew H. Hancock, Fremont, CA (US); Gary Weller, Los Gatos, CA (US); Christopher Julian, Los Gatos, CA (US); James Gannoe, West Milford, NJ (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 483 days.

This patent is subject to a terminal disclaimer.

(21) Appl. No.: 12/979,242

(22) Filed: Dec. 27, 2010

(65) Prior Publication Data

US 2011/0092777 A1  Apr. 21, 2011

Related U.S. Application Data

(63) Continuation of application No. 11/955,079, filed on Dec. 12, 2007, which is a continuation of application No. 11/282,320, filed on Nov. 17, 2005, now Pat. No. 8,454,503, which is a continuation-in-part of application No. 10/991,140, filed on Nov. 17, 2004, now abandoned.

(51) Int. Cl.
*A61B 1/32* (2006.01)

(52) U.S. Cl.
USPC ........................................... 600/219

(58) Field of Classification Search
USPC ................ 606/139, 148; 600/201–206, 104
See application file for complete search history.

(56) References Cited

U.S. PATENT DOCUMENTS 2,108,206 A 2/1938 Meeker
2,508,690 A 7/1948 Schmerl
(Continued)

FOREIGN PATENT DOCUMENTS

EP 0 137 878 A1 4/1985
EP 137878 A1 4/1985
(Continued)

OTHER PUBLICATIONS

Benjamin, S.B., et al., A Double-Blind Cross Over Study of the Garren-Edwards anti-Obesity Bubblem Abstract Submitted to A/S/G/E/ 1987, Georgetown University Hospital and Fairfax Hospital, Washington, D.C. and Fairfax, VA.

(Continued)

*Primary Examiner* — Jan Christopher Merene
(74) *Attorney, Agent, or Firm* — Mintz Levin Cohn Ferris Glovsky and Popeo, P.C.

(57) ABSTRACT

A medical device for managing tissue in an organ, such as the stomach, for retracting or positioning tissue and related organs to allow certain regions of the stomach to be acquired for a gastroplasty procedure. The medical device includes an elongated body having a proximal end and a distal end, and a tissue treatment device attached to the distal end of the elongated body. The tissue treatment device includes a first jaw opposite a second jaw, and each jaw is adapted to acquire tissue. A retractor is disposed along the tissue treatment device and adapted to be moveable from a delivery position to a retraction position to move or manage the tissue of the stomach. The medical device also includes a collapsible barrier disposed between the first and second jaws of the tissue treatment device to direct tissue into the first and second jaws separately.

19 Claims, 65 Drawing Sheets

(56) References Cited

U.S. PATENT DOCUMENTS

| | | |
|---|---|---|
| 3,119,392 A | 1/1964 | Zeiss et al. |
| 3,372,443 A | 3/1968 | Daddona, Jr. |
| 3,395,710 A | 8/1968 | Stratton et al. |
| 3,729,006 A | 4/1973 | Wilder et al. |
| 3,771,516 A | 11/1973 | Corriero |
| 3,986,493 A | 10/1976 | Hendren, III |
| 4,057,065 A | 11/1977 | Thow |
| 4,063,561 A | 12/1977 | McKenna |
| 4,133,315 A | 1/1979 | Berman et al. |
| 4,134,405 A | 1/1979 | Smit |
| 4,198,982 A | 4/1980 | Fortner et al. |
| 4,246,893 A | 1/1981 | Berson |
| 4,258,705 A | 3/1981 | Sorensen et al. |
| 4,311,146 A | 1/1982 | Wonder |
| 4,315,509 A | 2/1982 | Smit |
| 4,343,066 A | 8/1982 | Lance |
| 4,402,445 A | 9/1983 | Green |
| 4,416,267 A | 11/1983 | Garren et al. |
| 4,445,897 A | 5/1984 | Ekbladh et al. |
| 4,458,681 A | 7/1984 | Hopkins |
| 4,485,805 A | 12/1984 | Foster, Jr. |
| 4,501,264 A | 2/1985 | Rockey |
| 4,547,192 A | 10/1985 | Brodsky et al. |
| 4,558,699 A | 12/1985 | Bashour |
| 4,592,339 A | 6/1986 | Kuzmak et al. |
| 4,592,354 A | 6/1986 | Rothfuss |
| 4,598,699 A | 7/1986 | Garren et al. |
| 4,607,618 A | 8/1986 | Angelchik |
| 4,610,383 A | 9/1986 | Rothfuss et al. |
| 4,636,205 A | 1/1987 | Steer |
| 4,641,653 A | 2/1987 | Rockey |
| 4,643,169 A | 2/1987 | Koss et al. |
| 4,646,722 A | 3/1987 | Silverstein et al. |
| 4,648,383 A | 3/1987 | Angelchik |
| 4,671,287 A | 6/1987 | Fiddian-Green |
| 4,694,827 A | 9/1987 | Weiner et al. |
| 4,696,288 A | 9/1987 | Kuzmak et al. |
| 4,716,900 A | 1/1988 | Ravo et al. |
| 4,723,547 A | 2/1988 | Kullas et al. |
| 4,739,758 A | 4/1988 | Lai et al. |
| 4,744,363 A | 5/1988 | Hasson |
| 4,773,393 A | 9/1988 | Haber et al. |
| 4,790,294 A | 12/1988 | Allred, III et al. |
| 4,795,430 A | 1/1989 | Quinn et al. |
| 4,803,985 A | 2/1989 | Hill |
| 4,841,888 A | 6/1989 | Mills et al. |
| 4,892,244 A | 1/1990 | Fox et al. |
| 4,899,747 A | 2/1990 | Garren et al. |
| 4,905,693 A | 3/1990 | Ravo |
| 4,911,148 A | 3/1990 | Sosnowski et al. |
| 4,925,446 A | 5/1990 | Garay et al. |
| 4,927,428 A | 5/1990 | Richards |
| 4,969,474 A | 11/1990 | Schwarz |
| 5,037,021 A | 8/1991 | Mills et al. |
| 5,059,193 A | 10/1991 | Kuslich |
| 5,080,663 A | 1/1992 | Mills et al. |
| 5,084,061 A | 1/1992 | Gau et al. |
| 5,112,310 A | 5/1992 | Grobe |
| 5,129,915 A | 7/1992 | Cantenys |
| 5,146,933 A | 9/1992 | Boyd |
| 5,156,609 A | 10/1992 | Nakao et al. |
| 5,171,233 A | 12/1992 | Amplatz et al. |
| 5,178,133 A | 1/1993 | Pena |
| 5,195,505 A | 3/1993 | Josefsen |
| 5,197,649 A | 3/1993 | Bessler et al. |
| 5,220,928 A | 6/1993 | Oddsen et al. |
| 5,222,961 A | 6/1993 | Nakao et al. |
| 5,226,429 A | 7/1993 | Kuzmak |
| 5,234,454 A | 8/1993 | Bangs |
| 5,235,966 A | 8/1993 | Jamner |
| 5,246,456 A | 9/1993 | Wilkinson |
| 5,248,302 A | 9/1993 | Patrick et al. |
| 5,250,058 A | 10/1993 | Miller et al. |
| 5,254,126 A | 10/1993 | Filipi et al. |
| 5,259,366 A | 11/1993 | Reydel et al. |
| 5,259,399 A | 11/1993 | Brown |
| 5,261,920 A | 11/1993 | Main et al. |
| 5,263,629 A | 11/1993 | Trumbull et al. |
| 5,284,128 A | 2/1994 | Hart |
| 5,297,536 A | 3/1994 | Wilk |
| 5,301,658 A | 4/1994 | Zhu et al. |
| 5,306,300 A | 4/1994 | Berry |
| 5,309,896 A | 5/1994 | Moll et al. |
| 5,309,927 A | 5/1994 | Welch |
| 5,318,528 A | 6/1994 | Heaven et al. |
| 5,318,530 A | 6/1994 | Nelson, Jr. |
| 5,327,914 A | 7/1994 | Shlain |
| 5,330,486 A | 7/1994 | Wilk |
| 5,330,503 A | 7/1994 | Yoon |
| 5,331,975 A | 7/1994 | Bonutti |
| 5,334,209 A | 8/1994 | Yoon |
| 5,334,210 A | 8/1994 | Gianturco |
| 5,345,949 A | 9/1994 | Shlain |
| 5,346,501 A | 9/1994 | Regula et al. |
| 5,355,897 A | 10/1994 | Pietrafitta et al. |
| 5,358,496 A | 10/1994 | Ortiz et al. |
| 5,376,095 A | 12/1994 | Ortiz |
| 5,382,231 A | 1/1995 | Shlain |
| 5,395,030 A | 3/1995 | Kuramoto et al. |
| 5,395,367 A | 3/1995 | Wilk |
| 5,403,312 A | 4/1995 | Yates et al. |
| 5,403,326 A | 4/1995 | Harrison et al. |
| 5,409,012 A | 4/1995 | Sahatjian |
| 5,411,408 A | 5/1995 | Diviesti et al. |
| 5,411,508 A | 5/1995 | Bessler et al. |
| 5,425,705 A * | 6/1995 | Evard et al. ............... 604/28 |
| 5,433,721 A | 7/1995 | Hooven et al. |
| 5,437,291 A | 8/1995 | Pasricha et al. |
| 5,441,044 A * | 8/1995 | Tovey et al. ............... 600/234 |
| 5,449,368 A | 9/1995 | Kuzmak |
| 5,452,837 A | 9/1995 | Williamson, IV et al. |
| 5,458,131 A | 10/1995 | Wilk |
| 5,462,559 A | 10/1995 | Ahmed |
| D364,327 S * | 11/1995 | Graham ............... D8/105 |
| 5,465,894 A | 11/1995 | Clark et al. |
| 5,467,763 A | 11/1995 | McMahon et al. |
| 5,467,911 A | 11/1995 | Tsuruta et al. |
| 5,486,183 A | 1/1996 | Middleman et al. |
| 5,487,757 A | 1/1996 | Truckai et al. |
| 5,489,058 A | 2/1996 | Plyley et al. |
| 5,489,269 A | 2/1996 | Aldrich et al. |
| 5,501,654 A | 3/1996 | Failla et al. |
| 5,503,635 A | 4/1996 | Sauer et al. |
| 5,522,788 A | 6/1996 | Kuzmak |
| 5,527,319 A | 6/1996 | Green et al. |
| 5,535,935 A | 7/1996 | Vidal et al. |
| 5,542,949 A | 8/1996 | Yoon |
| 5,549,621 A | 8/1996 | Bessler et al. |
| 5,551,622 A | 9/1996 | Yoon |
| 5,555,898 A | 9/1996 | Suzuki et al. |
| 5,558,665 A | 9/1996 | Kieturakis |
| 5,571,116 A | 11/1996 | Bolanos et al. |
| 5,577,654 A | 11/1996 | Bishop |
| 5,578,044 A | 11/1996 | Gordon et al. |
| 5,582,616 A | 12/1996 | Bolduc et al. |
| 5,584,861 A | 12/1996 | Swain et al. |
| 5,588,579 A | 12/1996 | Schnut et al. |
| 5,599,279 A | 2/1997 | Slotman |
| 5,601,604 A | 2/1997 | Vincent |
| 5,603,443 A | 2/1997 | Clark et al. |
| 5,607,094 A | 3/1997 | Clark et al. |
| 5,624,381 A | 4/1997 | Kieturakis |
| 5,626,588 A | 5/1997 | Sauer et al. |
| 5,639,008 A | 6/1997 | Gallagher et al. |
| 5,649,937 A | 7/1997 | Bito et al. |
| 5,651,769 A | 7/1997 | Waxman et al. |
| 5,655,698 A | 8/1997 | Yoon |
| 5,656,012 A * | 8/1997 | Sienkiewicz ............... 600/204 |
| 5,662,664 A | 9/1997 | Gordon et al. |
| 5,662,667 A | 9/1997 | Knodel |
| 5,667,520 A | 9/1997 | Bonutti |
| 5,676,659 A | 10/1997 | McGurk |
| 5,676,674 A | 10/1997 | Bolanos et al. |
| 5,681,263 A | 10/1997 | Flesch |

(56) References Cited

U.S. PATENT DOCUMENTS

| | | |
|---|---|---|
| 5,683,349 A | 11/1997 | Makower et al. |
| 5,685,868 A | 11/1997 | Lundquist |
| 5,690,656 A | 11/1997 | Cope et al. |
| 5,697,943 A | 12/1997 | Sauer et al. |
| 5,707,382 A | 1/1998 | Sierocuk et al. |
| 5,722,990 A | 3/1998 | Sugarbaker et al. |
| 5,728,178 A | 3/1998 | Buffington et al. |
| 5,735,848 A | 4/1998 | Yates et al. |
| 5,749,893 A | 5/1998 | Vidal et al. |
| 5,755,661 A * | 5/1998 | Schwartzman ............... 600/216 |
| 5,755,730 A | 5/1998 | Swain et al. |
| 5,766,216 A | 6/1998 | Gangal et al. |
| 5,776,054 A | 7/1998 | Bobra |
| 5,782,844 A | 7/1998 | Yoon et al. |
| 5,788,715 A | 8/1998 | Watson, Jr. et al. |
| 5,792,153 A | 8/1998 | Swain et al. |
| 5,797,931 A | 8/1998 | Bito et al. |
| 5,810,851 A | 9/1998 | Yoon |
| 5,810,855 A | 9/1998 | Rayburn et al. |
| 5,810,882 A | 9/1998 | Bolduc et al. |
| 5,816,471 A | 10/1998 | Plyley et al. |
| 5,820,584 A | 10/1998 | Crabb |
| 5,824,008 A | 10/1998 | Bolduc et al. |
| 5,827,298 A | 10/1998 | Hart et al. |
| 5,833,690 A | 11/1998 | Yates et al. |
| 5,836,311 A | 11/1998 | Borst et al. |
| 5,839,639 A | 11/1998 | Sauer et al. |
| 5,860,581 A | 1/1999 | Robertson et al. |
| 5,861,036 A | 1/1999 | Godin |
| 5,865,730 A | 2/1999 | Fox et al. |
| 5,868,141 A | 2/1999 | Ellias |
| 5,868,760 A | 2/1999 | McGuckin, Jr. |
| 5,876,448 A | 3/1999 | Thompson et al. |
| 5,879,371 A | 3/1999 | Gardiner et al. |
| 5,887,594 A | 3/1999 | LoCicero, III |
| 5,888,196 A | 3/1999 | Bonutti |
| 5,897,534 A | 4/1999 | Heim et al. |
| 5,897,562 A | 4/1999 | Bolanos et al. |
| 5,904,147 A | 5/1999 | Conlan et al. |
| 5,906,625 A | 5/1999 | Bito et al. |
| 5,910,105 A | 6/1999 | Swain et al. |
| 5,910,149 A | 6/1999 | Kuzmak |
| 5,921,993 A | 7/1999 | Yoon |
| 5,927,284 A | 7/1999 | Borst et al. |
| 5,928,264 A | 7/1999 | Sugarbaker et al. |
| 5,935,107 A | 8/1999 | Taylor et al. |
| 5,938,669 A | 8/1999 | Klaiber et al. |
| 5,941,849 A | 8/1999 | Amos, Jr. et al. |
| 5,947,983 A | 9/1999 | Solar et al. |
| 5,964,772 A | 10/1999 | Bolduc et al. |
| 5,964,782 A | 10/1999 | Lafontaine et al. |
| 5,970,149 A | 10/1999 | Johnson |
| 5,972,001 A | 10/1999 | Yoon |
| 5,972,002 A | 10/1999 | Bark et al. |
| 5,976,161 A | 11/1999 | Kirsch et al. |
| 5,980,537 A | 11/1999 | Ouchi |
| 5,993,464 A | 11/1999 | Knodel |
| 5,993,473 A | 11/1999 | Chan et al. |
| 6,009,582 A * | 1/2000 | Harrison et al. .................. 7/118 |
| 6,013,027 A | 1/2000 | Khan et al. |
| 6,015,378 A | 1/2000 | Borst et al. |
| 6,030,364 A | 2/2000 | Durgin et al. |
| 6,030,392 A | 2/2000 | Dakov |
| 6,042,538 A | 3/2000 | Puskas |
| 6,044,847 A | 4/2000 | Carter et al. |
| 6,067,991 A | 5/2000 | Forsell |
| 6,074,343 A | 6/2000 | Nathanson et al. |
| 6,083,241 A | 7/2000 | Longo et al. |
| 6,086,600 A | 7/2000 | Kortenbach |
| 6,113,609 A | 9/2000 | Adams |
| 6,119,913 A | 9/2000 | Adams et al. |
| 6,120,513 A | 9/2000 | Bailey et al. |
| 6,136,006 A | 10/2000 | Johnson et al. |
| D433,915 S * | 11/2000 | Elsener, Sr. ................... D8/105 |
| 6,142,957 A | 11/2000 | Diamond et al. |
| 6,159,146 A | 12/2000 | El Gazayerli |
| 6,159,195 A | 12/2000 | Ha et al. |
| 6,165,183 A | 12/2000 | Kuehn et al. |
| 6,179,195 B1 | 1/2001 | Adams et al. |
| 6,186,942 B1 | 2/2001 | Sullivan et al. |
| 6,186,985 B1 | 2/2001 | Snow |
| 6,197,022 B1 | 3/2001 | Baker |
| 6,200,318 B1 | 3/2001 | Har-Shai et al. |
| 6,206,822 B1 | 3/2001 | Foley et al. |
| 6,206,893 B1 | 3/2001 | Klein et al. |
| 6,224,614 B1 | 5/2001 | Yoon |
| 6,231,561 B1 | 5/2001 | Frazier et al. |
| 6,248,058 B1 | 6/2001 | Silverman et al. |
| 6,254,642 B1 | 7/2001 | Taylor |
| 6,273,897 B1 | 8/2001 | Dalessandro et al. |
| 6,279,809 B1 | 8/2001 | Nicolo |
| 6,290,674 B1 | 9/2001 | Roue et al. |
| 6,290,705 B1 | 9/2001 | Chan et al. |
| 6,293,923 B1 | 9/2001 | Yachia et al. |
| 6,302,917 B1 | 10/2001 | Dua et al. |
| 6,312,437 B1 | 11/2001 | Kortenbach |
| 6,328,689 B1 | 12/2001 | Gonzalez et al. |
| 6,334,865 B1 | 1/2002 | Redmond et al. |
| 6,338,345 B1 | 1/2002 | Johnson et al. |
| 6,352,543 B1 | 3/2002 | Cole |
| 6,358,197 B1 | 3/2002 | Silverman et al. |
| 6,379,366 B1 | 4/2002 | Fleischmann et al. |
| 6,387,104 B1 | 5/2002 | Pugsley, Jr. et al. |
| 6,398,795 B1 | 6/2002 | McAlister et al. |
| 6,413,234 B1 | 7/2002 | Thompson et al. |
| 6,416,535 B1 | 7/2002 | Lazarus |
| 6,423,087 B1 | 7/2002 | Sawada |
| 6,432,040 B1 | 8/2002 | Meah |
| 6,447,533 B1 | 9/2002 | Adams |
| 6,451,042 B1 | 9/2002 | Bonutti |
| 6,460,543 B1 | 10/2002 | Forsell |
| 6,475,136 B1 | 11/2002 | Forsell |
| 6,491,707 B2 | 12/2002 | Makower et al. |
| 6,494,888 B1 | 12/2002 | Laufer et al. |
| 6,506,196 B1 | 1/2003 | Laufer |
| 6,533,762 B2 | 3/2003 | Kanner et al. |
| 6,535,764 B2 | 3/2003 | Imran et al. |
| 6,540,789 B1 | 4/2003 | Silverman et al. |
| 6,551,310 B1 | 4/2003 | Ganz et al. |
| 6,554,844 B2 | 4/2003 | Lee et al. |
| 6,558,400 B2 | 5/2003 | Deem et al. |
| 6,561,969 B2 | 5/2003 | Frazier et al. |
| 6,572,629 B2 | 6/2003 | Kalloo et al. |
| 6,579,301 B1 | 6/2003 | Bales et al. |
| 6,592,596 B1 | 7/2003 | Geitz |
| 6,605,037 B1 | 8/2003 | Moll et al. |
| 6,626,899 B2 | 9/2003 | Houser et al. |
| 6,629,987 B1 | 10/2003 | Gambale et al. |
| 6,632,227 B2 | 10/2003 | Adams |
| 6,656,194 B1 | 12/2003 | Gannoe et al. |
| 6,663,598 B1 | 12/2003 | Carrillo, Jr. et al. |
| 6,663,639 B1 | 12/2003 | Laufer et al. |
| 6,663,640 B2 | 12/2003 | Kortenbach |
| 6,675,809 B2 | 1/2004 | Stack et al. |
| 6,682,520 B2 | 1/2004 | Ingenito |
| 6,689,062 B1 | 2/2004 | Mesallum |
| 6,692,485 B1 | 2/2004 | Brock et al. |
| 6,716,222 B2 | 4/2004 | McAlister et al. |
| 6,733,512 B2 | 5/2004 | McGhan |
| 6,736,822 B2 | 5/2004 | McClellan et al. |
| 6,740,098 B2 | 5/2004 | Abrams et al. |
| 6,740,121 B2 | 5/2004 | Geitz |
| 6,746,460 B2 | 6/2004 | Gannoe et al. |
| 6,746,489 B2 | 6/2004 | Dua et al. |
| 6,754,536 B2 | 6/2004 | Swoyer et al. |
| 6,755,849 B1 | 6/2004 | Gowda et al. |
| 6,755,869 B2 | 6/2004 | Geitz |
| 6,756,364 B2 | 6/2004 | Barbier et al. |
| 6,764,518 B2 | 7/2004 | Godin |
| 6,773,440 B2 | 8/2004 | Gannoe et al. |
| 6,773,441 B1 | 8/2004 | Laufer et al. |
| 6,786,898 B2 | 9/2004 | Guenst |
| 6,790,214 B2 | 9/2004 | Kraemer et al. |
| 6,802,868 B2 | 10/2004 | Silverman et al. |

(56) References Cited

U.S. PATENT DOCUMENTS

| | | |
|---|---|---|
| 6,821,285 B2 | 11/2004 | Laufer et al. |
| 6,830,546 B1 | 12/2004 | Chin et al. |
| 6,835,199 B2 | 12/2004 | McGuckin, Jr. et al. |
| 6,835,200 B2 | 12/2004 | Laufer et al. |
| 6,837,848 B2 | 1/2005 | Bonner et al. |
| 6,840,423 B2 | 1/2005 | Adams et al. |
| 6,845,776 B2 | 1/2005 | Stack et al. |
| 6,896,682 B1 | 5/2005 | McClellan et al. |
| 6,916,332 B2 | 7/2005 | Adams |
| 6,926,722 B2 | 8/2005 | Geitz |
| 6,966,919 B2 | 11/2005 | Sixto, Jr. et al. |
| 6,973,882 B2 | 12/2005 | Baechle et al. |
| 6,981,978 B2 | 1/2006 | Gannoe |
| 6,991,643 B2 | 1/2006 | Saadat |
| 6,994,715 B2 | 2/2006 | Gannoe et al. |
| 7,020,531 B1 | 3/2006 | Colliou et al. |
| 7,025,791 B2 | 4/2006 | Levine et al. |
| 7,033,373 B2 | 4/2006 | de la Torre et al. |
| 7,033,378 B2 | 4/2006 | Smith et al. |
| 7,033,384 B2 | 4/2006 | Gannoe et al. |
| 7,037,343 B2 | 5/2006 | Imran |
| 7,037,344 B2 | 5/2006 | Kagan et al. |
| 7,063,715 B2 | 6/2006 | Onuki et al. |
| 7,083,629 B2 | 8/2006 | Weller et al. |
| 7,083,630 B2 | 8/2006 | DeVries et al. |
| 7,087,011 B2 | 8/2006 | Cabiri et al. |
| 7,090,684 B2 | 8/2006 | McGuckin, Jr. et al. |
| 7,097,650 B2 | 8/2006 | Weller et al. |
| 7,141,055 B2 | 11/2006 | Abrams et al. |
| 7,211,094 B2 | 5/2007 | Gannoe et al. |
| 7,214,233 B2 | 5/2007 | Gannoe et al. |
| 7,220,237 B2 | 5/2007 | Gannoe et al. |
| 7,229,428 B2 | 6/2007 | Gannoe et al. |
| 7,288,099 B2 | 10/2007 | Deem et al. |
| 7,288,101 B2 | 10/2007 | Deem et al. |
| 7,789,848 B2 | 9/2010 | Gannoe et al. |
| 7,918,869 B2 | 4/2011 | Saadat et al. |
| 8,403,838 B2 | 3/2013 | Roth et al. |
| 8,403,839 B2 | 3/2013 | Roth et al. |
| 8,454,503 B2 | 6/2013 | Roth et al. |
| 2001/0014800 A1 | 8/2001 | Frazier et al. |
| 2001/0020190 A1 | 9/2001 | Taylor |
| 2001/0037127 A1 | 11/2001 | De Hoyos Garza |
| 2002/0022851 A1 | 2/2002 | Kalloo et al. |
| 2002/0035361 A1 | 3/2002 | Houser et al. |
| 2002/0040226 A1 | 4/2002 | Laufer et al. |
| 2002/0047036 A1 | 4/2002 | Sullivan et al. |
| 2002/0058967 A1 | 5/2002 | Jervis |
| 2002/0072761 A1 | 6/2002 | Abrams et al. |
| 2002/0077661 A1 | 6/2002 | Saadat |
| 2002/0078967 A1 | 6/2002 | Sixto, Jr. et al. |
| 2002/0082621 A1 | 6/2002 | Schurr et al. |
| 2002/0143346 A1 | 10/2002 | McGuckin, Jr. et al. |
| 2002/0165589 A1 | 11/2002 | Imran et al. |
| 2002/0183768 A1 | 12/2002 | Deem et al. |
| 2002/0193816 A1 | 12/2002 | Laufer et al. |
| 2003/0040764 A1 | 2/2003 | Adams |
| 2003/0040804 A1 | 2/2003 | Stack et al. |
| 2003/0040808 A1 | 2/2003 | Stack et al. |
| 2003/0045778 A1 | 3/2003 | Ohline et al. |
| 2003/0065340 A1 | 4/2003 | Geitz |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0109931 A1 | 6/2003 | Geitz |
| 2003/0109935 A1 | 6/2003 | Geitz |
| 2003/0120285 A1 | 6/2003 | Kortenbach |
| 2003/0120289 A1 | 6/2003 | McGuckin, Jr. et al. |
| 2003/0132267 A1 | 7/2003 | Adams et al. |
| 2003/0158563 A1 | 8/2003 | McClellan et al. |
| 2003/0158601 A1 | 8/2003 | Silverman et al. |
| 2003/0171760 A1 | 9/2003 | Gambale |
| 2003/0208209 A1 | 11/2003 | Gambale et al. |
| 2003/0216754 A1 | 11/2003 | Kraemer et al. |
| 2003/0225312 A1 | 12/2003 | Suzuki et al. |
| 2004/0006351 A1 | 1/2004 | Gannoe et al. |
| 2004/0009224 A1 | 1/2004 | Miller |
| 2004/0010245 A1 | 1/2004 | Cerier et al. |
| 2004/0010271 A1 | 1/2004 | Kortenbach |
| 2004/0024386 A1 | 2/2004 | Deem et al. |
| 2004/0030347 A1 | 2/2004 | Gannoe et al. |
| 2004/0037865 A1 | 2/2004 | Miller |
| 2004/0039452 A1 | 2/2004 | Bessler |
| 2004/0044354 A1 | 3/2004 | Gannoe et al. |
| 2004/0049209 A1 | 3/2004 | Benchetrit |
| 2004/0059349 A1 | 3/2004 | Sixto, Jr. et al. |
| 2004/0059354 A1 | 3/2004 | Smith et al. |
| 2004/0059358 A1 | 3/2004 | Kortenbach et al. |
| 2004/0082963 A1 | 4/2004 | Gannoe et al. |
| 2004/0087977 A1 | 5/2004 | Nolan et al. |
| 2004/0088008 A1 | 5/2004 | Gannoe et al. |
| 2004/0089313 A1 | 5/2004 | Utley et al. |
| 2004/0092892 A1 | 5/2004 | Kagan et al. |
| 2004/0092974 A1 | 5/2004 | Gannoe et al. |
| 2004/0097989 A1 | 5/2004 | Molina Trigueros |
| 2004/0107004 A1 | 6/2004 | Levine et al. |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0122526 A1 | 6/2004 | Imran |
| 2004/0133147 A1 | 7/2004 | Woo |
| 2004/0133238 A1 | 7/2004 | Cerier |
| 2004/0138525 A1 | 7/2004 | Saadat |
| 2004/0138526 A1 | 7/2004 | Guenst |
| 2004/0138529 A1 | 7/2004 | Wiltshire et al. |
| 2004/0138531 A1 | 7/2004 | Bonner et al. |
| 2004/0138682 A1 | 7/2004 | Onuki et al. |
| 2004/0147958 A1 | 7/2004 | Lam et al. |
| 2004/0148021 A1 | 7/2004 | Cartledge et al. |
| 2004/0148034 A1 | 7/2004 | Kagan et al. |
| 2004/0158264 A1 | 8/2004 | Adams et al. |
| 2004/0158331 A1 | 8/2004 | Stack et al. |
| 2004/0162568 A1 | 8/2004 | Saadat |
| 2004/0167546 A1 | 8/2004 | Saadat et al. |
| 2004/0172141 A1 | 9/2004 | Stack et al. |
| 2004/0181242 A1 | 9/2004 | Stack et al. |
| 2004/0193190 A1 | 9/2004 | Liddicoat et al. |
| 2004/0194157 A1 | 9/2004 | Meguid |
| 2004/0194790 A1 | 10/2004 | Laufer et al. |
| 2004/0210243 A1 | 10/2004 | Gannoe et al. |
| 2004/0215180 A1 | 10/2004 | Starkebaum et al. |
| 2004/0220682 A1 | 11/2004 | Levine et al. |
| 2004/0225183 A1 | 11/2004 | Michlitsch et al. |
| 2004/0225194 A1 | 11/2004 | Smith et al. |
| 2004/0225305 A1 | 11/2004 | Ewers et al. |
| 2004/0236357 A1 | 11/2004 | Kraemer et al. |
| 2004/0248034 A1 | 12/2004 | Henderson et al. |
| 2004/0249362 A1 | 12/2004 | Levine et al. |
| 2004/0267303 A1 | 12/2004 | Guenst |
| 2005/0010162 A1 | 1/2005 | Utley et al. |
| 2005/0021681 A1 | 1/2005 | Oommen |
| 2005/0033328 A1 | 2/2005 | Laufer et al. |
| 2005/0038415 A1 | 2/2005 | Rohr et al. |
| 2005/0038462 A1 | 2/2005 | Lubock et al. |
| 2005/0049718 A1 | 3/2005 | Dann et al. |
| 2005/0055038 A1 | 3/2005 | Kelleher et al. |
| 2005/0055039 A1 | 3/2005 | Burnett et al. |
| 2005/0065401 A1 | 3/2005 | Saadat et al. |
| 2005/0075622 A1 | 4/2005 | Levine et al. |
| 2005/0075653 A1 | 4/2005 | Saadat et al. |
| 2005/0080435 A1 | 4/2005 | Smith et al. |
| 2005/0080438 A1 | 4/2005 | Weller et al. |
| 2005/0080444 A1 | 4/2005 | Kraemer et al. |
| 2005/0085787 A1 | 4/2005 | Laufer |
| 2005/0088100 A1 | 4/2005 | Chen et al. |
| 2005/0096750 A1 | 5/2005 | Kagan et al. |
| 2005/0119524 A1 | 6/2005 | Sekine et al. |
| 2005/0119671 A1 | 6/2005 | Reydel et al. |
| 2005/0119674 A1 | 6/2005 | Gingras |
| 2005/0143760 A1 | 6/2005 | Imran |
| 2005/0148818 A1 | 7/2005 | Mesallum |
| 2005/0149067 A1 | 7/2005 | Takemoto et al. |
| 2005/0149114 A1 | 7/2005 | Cartledge et al. |
| 2005/0154390 A1 | 7/2005 | Biedermann et al. |

(56) References Cited

U.S. PATENT DOCUMENTS

| | | |
|---|---|---|
| 2005/0177176 A1 | 8/2005 | Gerbi et al. |
| 2005/0192599 A1 | 9/2005 | Demarais |
| 2005/0192601 A1 | 9/2005 | Demarais |
| 2005/0194038 A1 | 9/2005 | Brabec et al. |
| 2005/0194294 A1 | 9/2005 | Oexle et al. |
| 2005/0194312 A1 | 9/2005 | Niemeyer et al. |
| 2005/0195925 A1 | 9/2005 | Traber |
| 2005/0195944 A1 | 9/2005 | Bartels et al. |
| 2005/0196356 A1 | 9/2005 | Leinen et al. |
| 2005/0197540 A1 | 9/2005 | Liedtke |
| 2005/0197622 A1 | 9/2005 | Blumenthal et al. |
| 2005/0197684 A1 | 9/2005 | Koch |
| 2005/0198476 A1 | 9/2005 | Gazsi et al. |
| 2005/0203547 A1 | 9/2005 | Weller et al. |
| 2005/0203548 A1 | 9/2005 | Weller et al. |
| 2005/0216041 A1 | 9/2005 | Okada et al. |
| 2005/0228415 A1 | 10/2005 | Gertner |
| 2005/0228504 A1 | 10/2005 | Demarais |
| 2005/0256533 A1 | 11/2005 | Roth et al. |
| 2005/0256587 A1 | 11/2005 | Egan |
| 2006/0020247 A1 | 1/2006 | Kagan et al. |
| 2006/0020254 A1 | 1/2006 | Hoffmann |
| 2006/0020276 A1 | 1/2006 | Saadat et al. |
| 2006/0036267 A1 | 2/2006 | Saadat et al. |
| 2006/0106288 A1 | 5/2006 | Roth et al. |
| 2006/0111735 A1 | 5/2006 | Crainich |
| 2006/0122462 A1 | 6/2006 | Roth et al. |
| 2006/0142787 A1 | 6/2006 | Weller et al. |
| 2006/0151568 A1 | 7/2006 | Weller et al. |
| 2008/0091077 A1 | 4/2008 | Roth et al. |
| 2008/0091078 A1 | 4/2008 | Roth et al. |
| 2008/0091079 A1 | 4/2008 | Roth et al. |
| 2009/0254099 A1 | 10/2009 | Baker |
| 2009/0275975 A1 | 11/2009 | Albrecht et al. |
| 2011/0124964 A1 | 5/2011 | Nobis |

FOREIGN PATENT DOCUMENTS

| | | | |
|---|---|---|---|
| EP | 0 174 843 A1 | 3/1986 | |
| EP | 0 246 999 A1 | 11/1987 | |
| EP | 246999 B1 | 12/1987 | |
| EP | 174843 A1 | 12/1991 | |
| EP | 0 540 010 A2 | 5/1993 | |
| EP | 540010 A3 | 10/1993 | |
| FR | 2 768 324 A1 | 3/1999 | |
| FR | 2768324 | 3/1999 | |
| JP | 63277063 A | 11/1988 | |
| JP | 63279854 | 11/1988 | |
| JP | 63302863 A | 12/1988 | |
| JP | 01049572 A | 2/1989 | |
| JP | 04297219 | 10/1992 | |
| WO | WO 94/18893 A1 | 9/1994 | |
| WO | WO 99/17662 A1 | 4/1999 | |
| WO | WO 99/53827 A1 | 10/1999 | |
| WO | WO 00/07640 A2 | 2/2000 | |
| WO | WO 00/32137 A1 | 6/2000 | |
| WO | WO 00/48656 A1 | 8/2000 | |
| WO | WO 00/78227 A1 | 12/2000 | |
| WO | WO 00/78229 A1 | 12/2000 | |
| WO | WO 01/26557 A1 | 4/2001 | |
| WO | WO 01/28432 A1 | 4/2001 | |
| WO | WO 01/66018 A1 | 9/2001 | |
| WO | WO 01/67964 A2 | 9/2001 | |
| WO | WO 01/85034 A1 | 11/2001 | |
| WO | WO 02/24080 A2 | 3/2002 | |
| WO | WO 02/35980 A2 | 5/2002 | |
| WO | WO 02/39880 A2 | 5/2002 | |
| WO | WO 02/071951 A1 | 9/2002 | |
| WO | WO 02/091961 A1 | 11/2002 | |
| WO | WO 02/096327 A2 | 12/2002 | |
| WO | WO 03/007796 A2 | 1/2003 | |
| WO | WO 03/017882 A2 | 3/2003 | |
| WO | WO 03/078721 A2 | 9/2003 | |
| WO | WO 03/086247 A1 | 10/2003 | |
| WO | WO 03/088844 A1 | 10/2003 | |
| WO | WO 03/094785 A1 | 11/2003 | |
| WO | WO 03/099140 A1 | 12/2003 | |
| WO | WO 03/105563 A2 | 12/2003 | |
| WO | WO 03/105671 A2 | 12/2003 | |
| WO | WO 2004/009269 A2 | 1/2004 | |
| WO | WO 2004/014237 A1 | 2/2004 | |
| WO | WO 2004/017863 A2 | 3/2004 | |
| WO | WO 2004/019787 A2 | 3/2004 | |
| WO | WO 2004/019788 A3 | 3/2004 | |
| WO | WO 2004/019826 A1 | 3/2004 | |
| WO | WO 2004/037064 A2 | 5/2004 | |
| WO | WO 2004/049911 A2 | 6/2004 | |
| WO | WO 2004/058102 A2 | 7/2004 | |
| WO | WO 2004/060150 A1 | 7/2004 | |
| WO | WO 2004/087014 A2 | 10/2004 | |
| WO | WO 2004/103189 A1 | 12/2004 | |
| WO | WO 2005/023118 A1 | 3/2005 | |
| WO | WO 2005/037152 A1 | 4/2005 | |
| WO | WO 2005/058239 A2 | 6/2005 | |
| WO | WO 2005/060882 A1 | 7/2005 | |
| WO | WO 2006/078781 A1 | 7/2006 | |

OTHER PUBLICATIONS

Benjamin, S.B., Small Bowel Obstruction and the Garren-Edwards Bubble, Lessons to be Learned? Abstracts Submitted to A/S/G/E 1987, Division of Gastroenterology, Department of Medicine, Georgetown University Hospital, Washington, D.C.

Boyle, Thomas M., M.D., et al., Small Instestinal Obstruction Secondary to Obturation by a Garren Gastric Bubble, The American Journal of Gastroenterology, vol. 82, No. 1, pp. 51-53, 1987.

Buchler, M.W., M.D. et al., A Technique for Gastroplasty as a Substitute for the Esophagus: Fundus Rotation Gastroplasty, Journal of the American College of Surgeons, vol. 182, pp. 241-245, Mar. 1996.

Cass, O.W., et al., Long-Term Follow-Up of Patients With Percutaneous Endoscopic Gastrostomy (PEG), Abstracts Submitted to A/S/G/E 1987, Department of Medicine, Hennepin County Medical Center, Minneapolis, MN 55415.

Chang, Craig G. M.D. , et al.. Gastro-Clip.RTM. Gastroplasty: A Very Long-Term Complication, Obesity Surgery, 14, .COPYRGT. FD-Communications Inc. 2004.

Clark, Charlene, R.N., The Gastric Bubble: Medicine, Magic or Mania? SGA Journal, vol. 9, No. 2, pp. 45-47, Fall 1986.

Cummings, D.E. et al. (2002). "Plasma Ghrelin Levels After Diet-Induced Weight Loss or Gastric Bypass Surgery," N. Engl. J. Med. 346(21):1623-1630.

Davenport, Horace W., Ph.D., D.Sc., Physiology of the Digestive Tract: An Introductory Text, 3d Ed., Cover and Table of Contents (undated).

DeMeester, Tom T., M.D., "Evolving Concepts of Reflux: The Ups and Downs of the LES," Canadian Journal of Gastroenterology, vol. 16, No. 5, pp. 327-331, 2002.

Power Medical Interventions Digital and Wireless Medical Technology, Product Innovation: SurgASSIST.TM., Internet Website—www/pmi2.com/access.sub.—flexability.asp, 6 pages, visited May 29, 2003.

Snowden Pencer, Diamon-Flex Angled Snake Retractor (class 1, 878.4800), Appendix F.f, Undated.

De Waele, B., M.D., et al., Intragastric Balloons for Preoperative Weight Reduction, Obesity Surgery, vol. 10, pp. 58-60, 2000.

Edell, Steven L., et al., Radiographic Evaluation of the Garren Gastric Bubble, American Journal of Radiology, vol. 145, pp. 49-50, Jul. 1985.

Endo Gia* Universal, Single UseStapler and Endo GIA Roticulator*, Brochure, 8 pages, Undated.

Filipi, Charles J. M.D., et al., Transoral, Flexible Endoscopic Suturing for Treatment of GERD: A Multicenter Trial, Gastrointestinal Endoscopy,. vol. 53, No. 4, pp. 416-422, 2001.

Gray, Henry, R.R.S., Anatomy of the Human Body, The Digestive System, Thirtieth American Edition, pp. 1466-1467 (Undated).

Guidant, Internet, AXIUS™ Vacuum 2 Stabilizer Systems, Internet Website—www.guidant.com/products/axius_vacuum.shtml, 8 pages, visited May 27, 2003.

(56) References Cited

OTHER PUBLICATIONS

Gukovsky-Reicher, S., M.D. et al., Expandable Metal Esophageal Stents: Efficacy and Safety. Review of Current Literature Data and of 53 Stents Placed at Harbor—UCLA Medical Center, www.medscape.com/viewarticle/423508_print pp. 1-20, Medscape General Medicine 4(1), 2003 © 2002 Medscape, downloaded Oct. 9, 2006.

Hepworth, Clive C. FRCS et al., Mechanical Endoscopic Methods of Haemostasis for Bleeding Peptic Ulcers: A Review, Bailliere's Clinical Gastroenterology, vol. 14, No. 3 pp. 467-476, 2000.

Ikeda, Y. et al., New Suturing Device for Transanal Endoscopic Microsurgery, Blackwell Science Ltd. p. 1290, 1997.

Johnson & Johnson Gatewaysm Endopath 3mm, 5mm and 10 mm Diameter Endoscopic Instruments, Internet Website—www.inigateway.com/home.ihtml?loc=USENG&page=viewContent&parentId=0900 . . . , 3 pages, visited May 29, 2003.

Kirby, Donald F., Incomplete Small Bowel Obstruction by the Garren-Edwards Gastric Bubble Necessitating Surgical Intervention, The American Journal of Gastroenterology, vol. 82, No. 3, pp. 251-253, 1987.

Nieben, Ole Gyring, et al., Intragastric Balloon as an Artificial Bezoar for Treatment of Obesity, The Lancet, pp. 198-199, Jan. 23, 1982.

Percival, Walter L., M.D., "The Balloon Diet": A Noninvasive Treatment for Morbid Obesity. Preliminary Report of 1908 Patients, The Canadian Journal of Surgery, vol. 27, No. 2, pp. 135-136, Mar. 1984.

Stoltenberg, P.H., et al., Intragastric Balloon Therapy of Obesity: A Randomized Double-Blind Trial, Abstracts of Papers 1985, Scott & White Clinic, Texas A&M College of Medicine, Temple, Texas.

Swain, C. Paul, M.D. et al., An Endoscopic Sewing Machine, Gastrointestinal Edoscopy, vol. 32, No. 1 pp. 36-38 1986.

Swain, C. Paul, M.D., Endoscopic Sewing and Stapling Machines, Endoscopy pp. 205-210, © Georg Thieme Verlag Stuttgart, New York, 1997.

Swain, C. Paul, M.D. et al., An Endoscopic Stapling Device: The Development of a New Flexible Endoscopically Controlled Device for Placing Multiple Transmural Staples in Gastrointestinal Tissue, Gastrointestinal Endoscopy, vol. 35, No. 4, pp. 338-339, 1989.

Swain, C. Paul, M.D., Endoscopic Suturing, Bailliere's Clinical Gastroenterology, Bailliere's Tindall,, vol. 13 No. 1, pp. 97-108, 1999.

Taylor, T. Vincent, et al., Gastric Balloons for Obesity, The Lancet, Abstract, Mar. 27, 1982.

Vandenplas, Y., et al., Intragastric Balloons in Adolescents With Morbid Obesity, European Journal of Gastroenterology & Hepatology, vol. 11, No. 3, pp. 243-245, 1999.

Villar, Hugo V., M.D., et al., Mechanisms of Satiety and Gastric Emptying After Gastric Partitioning and Bypass, Surgery, pp. 229-236, Aug. 1981.

Wullstein, C., et al., Compression Anastomosis (AKA-2) in Colorectal Surgery: Results in 442 Consecutive Patients, British Journal of Surgery 2000, pp. 1071-1075.

\* cited by examiner

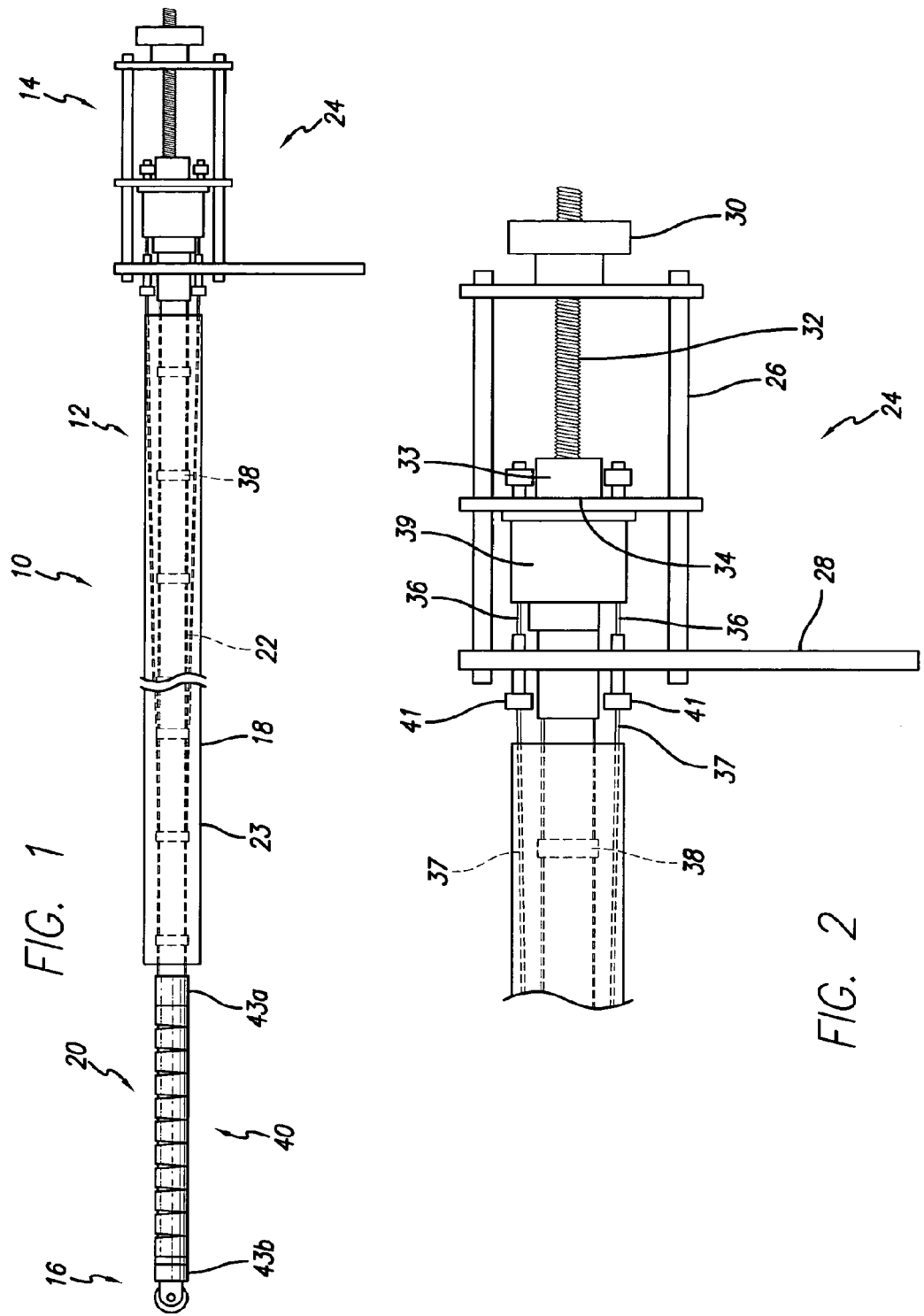

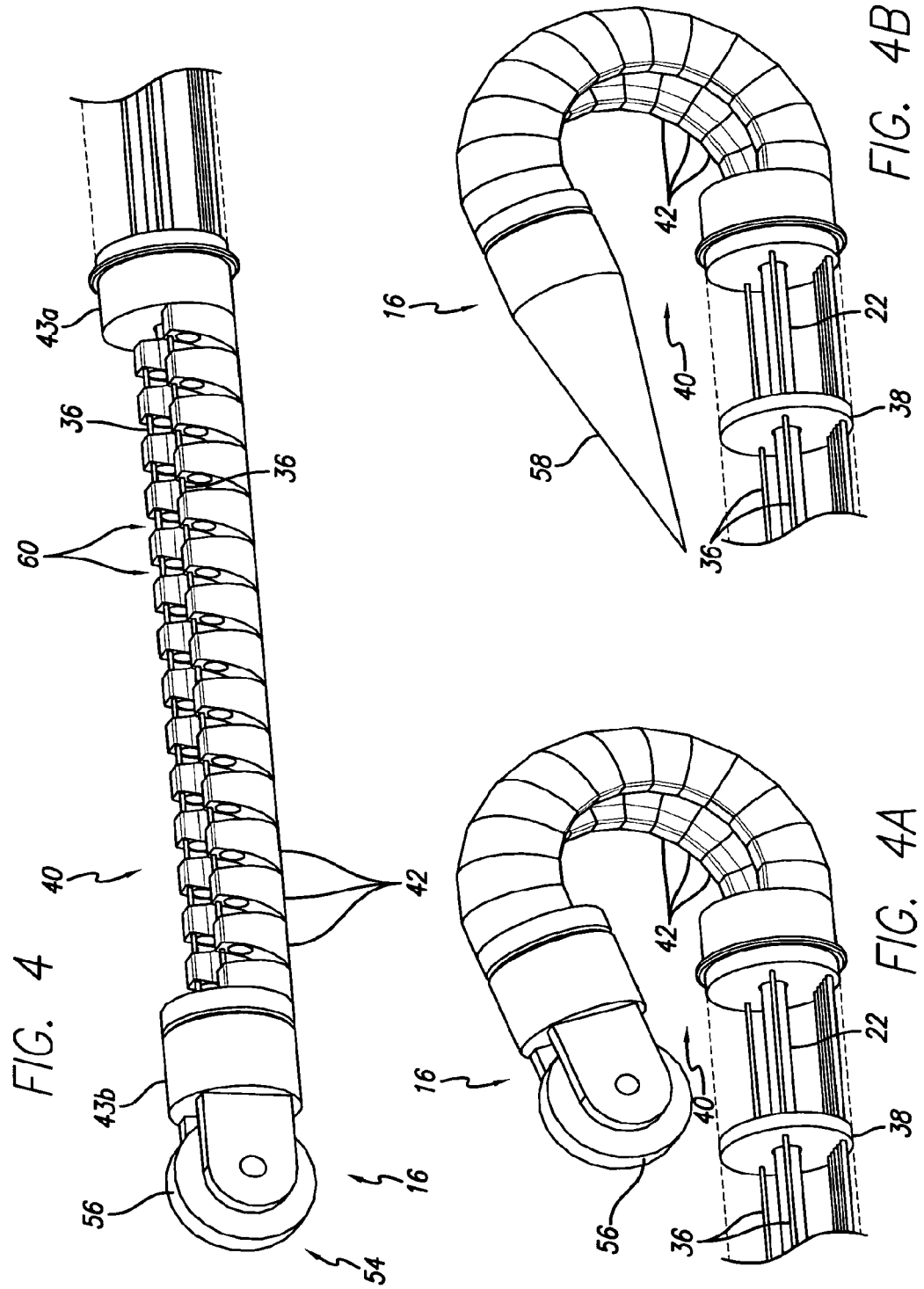

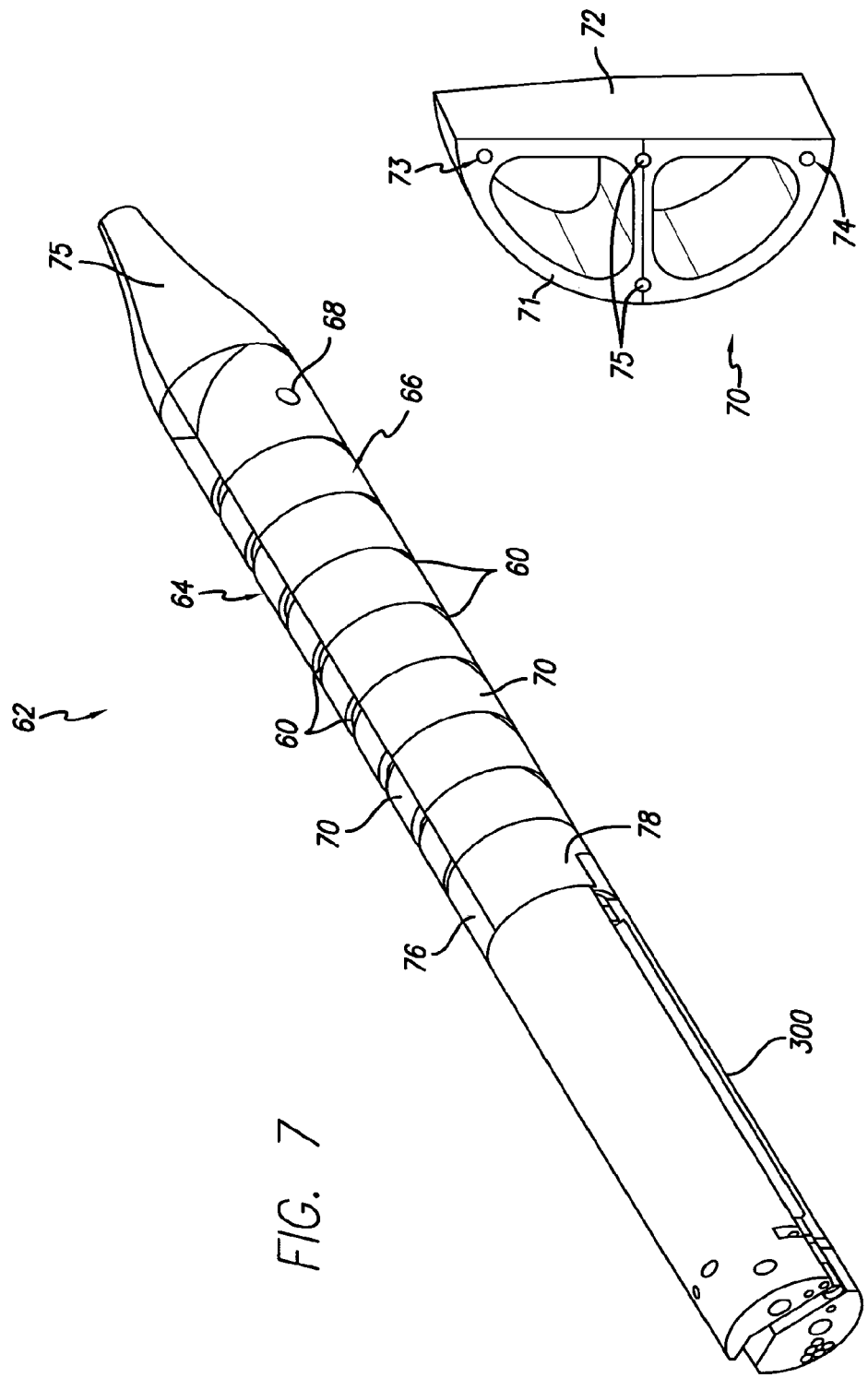

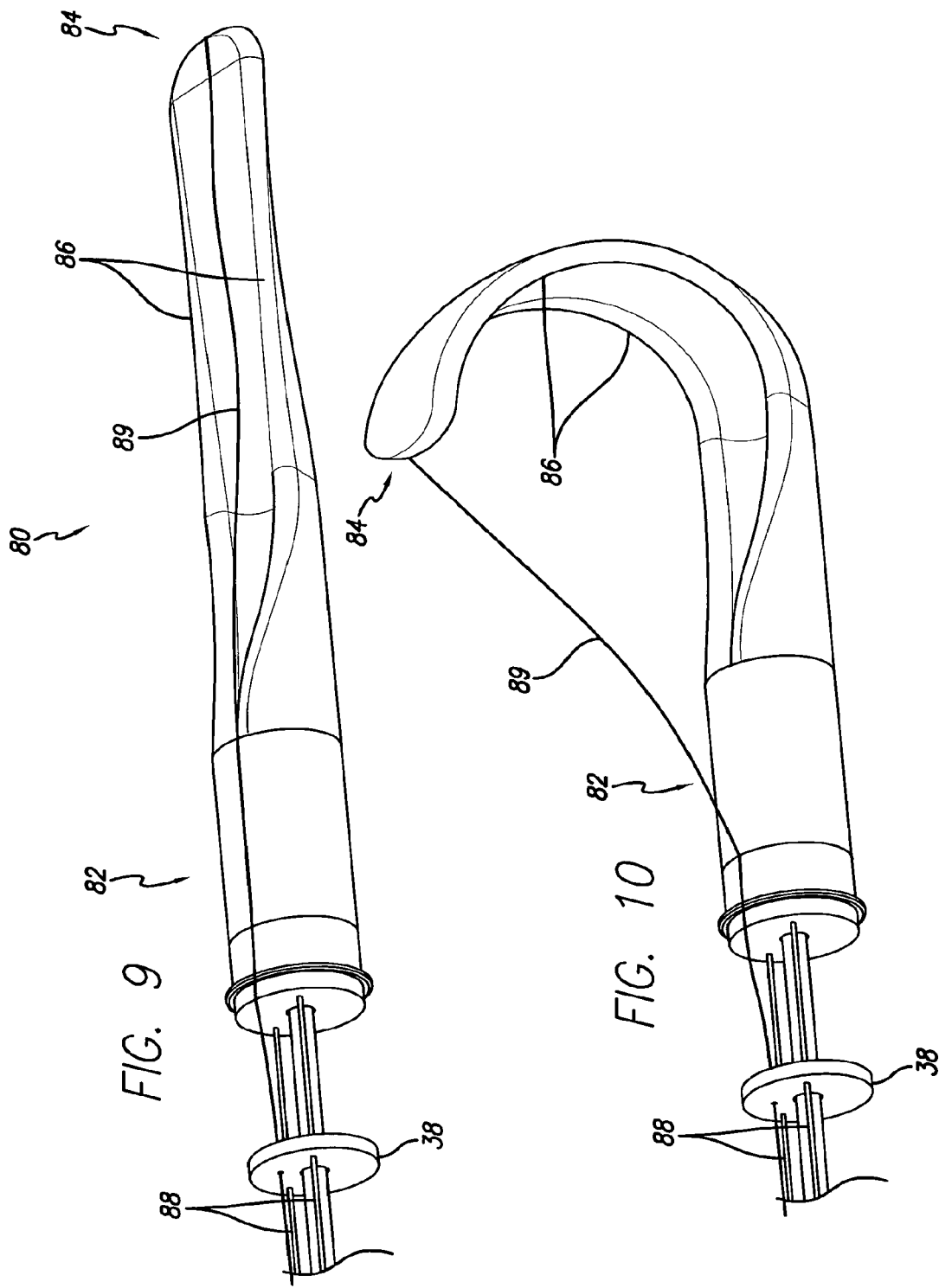

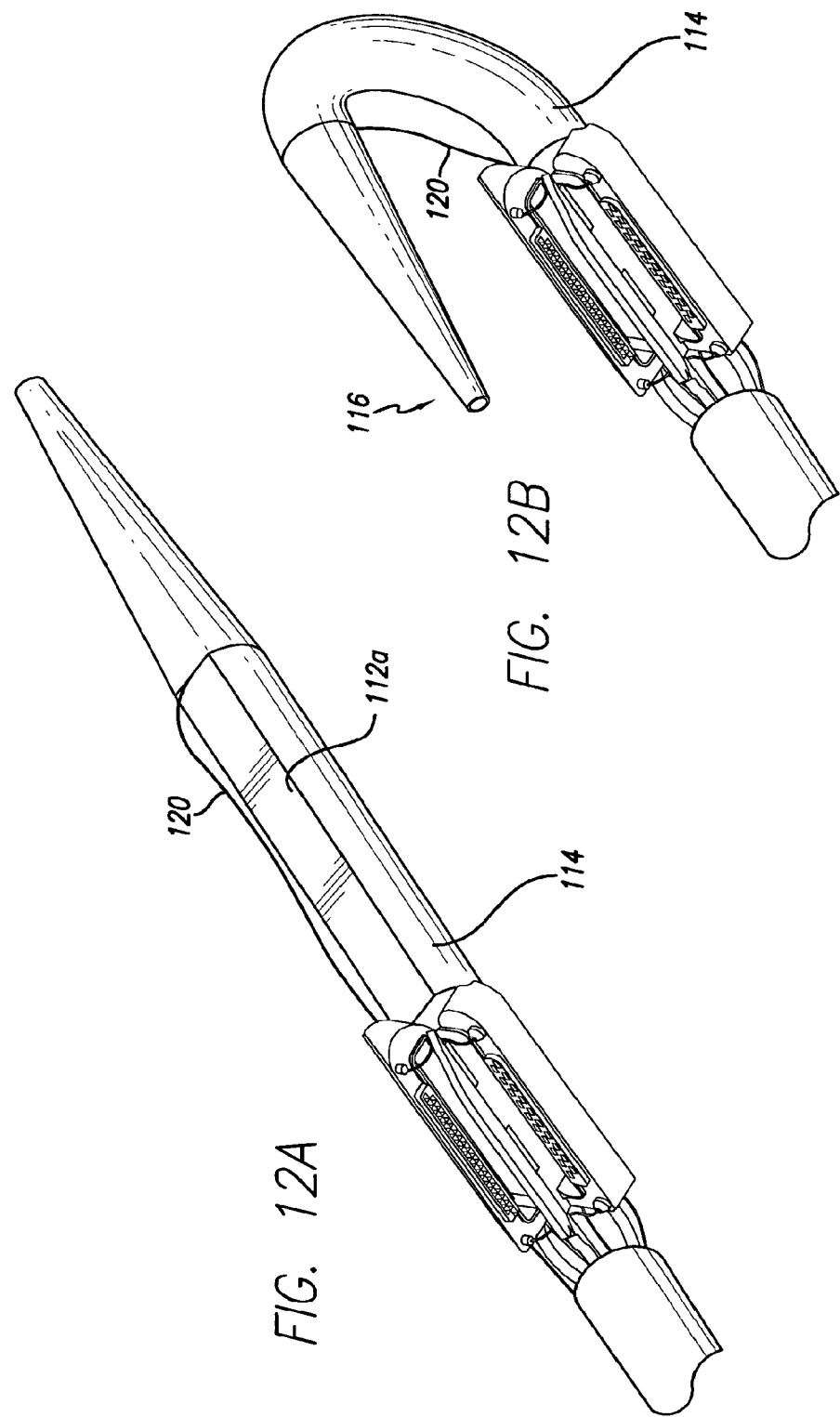

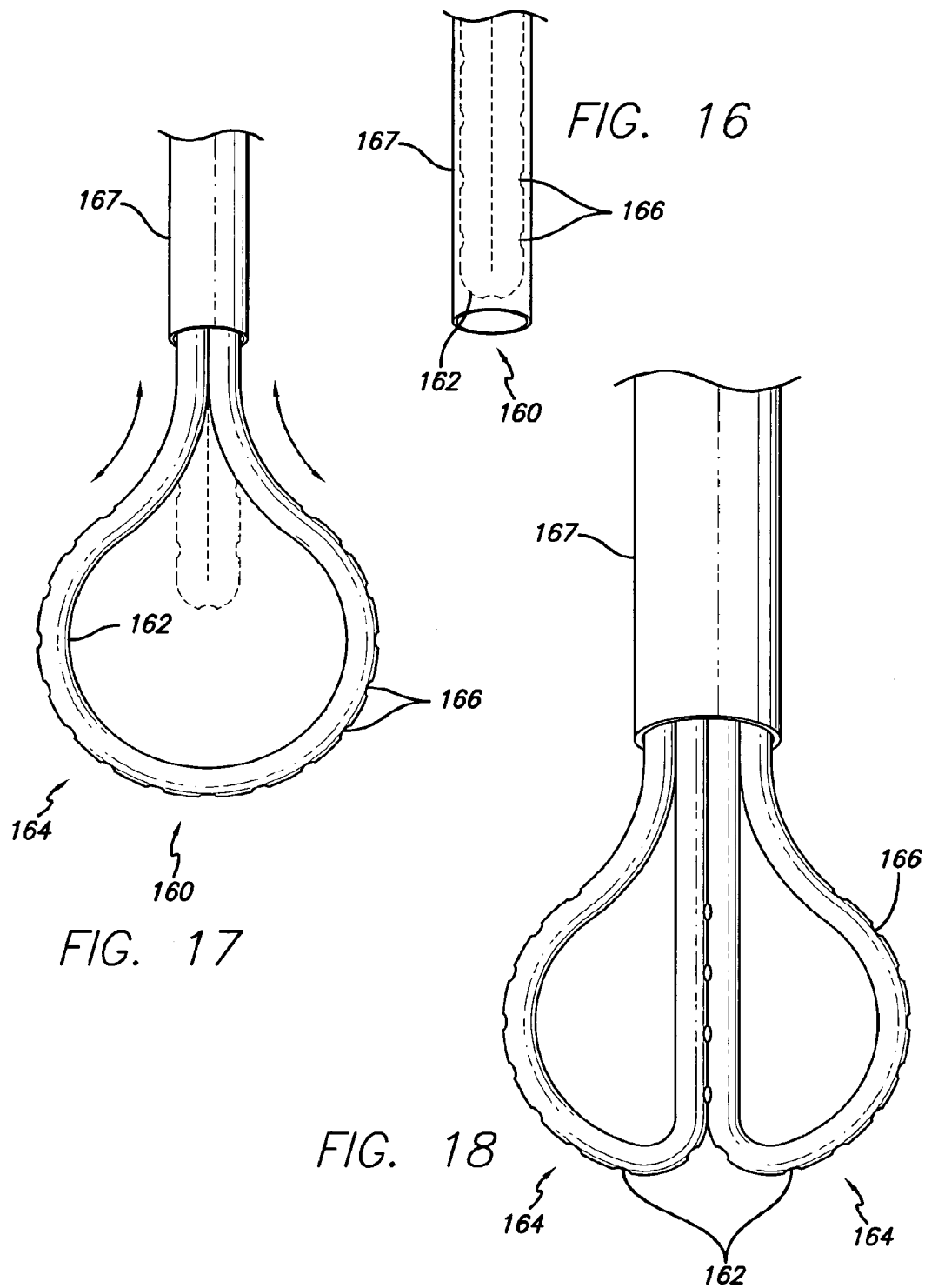

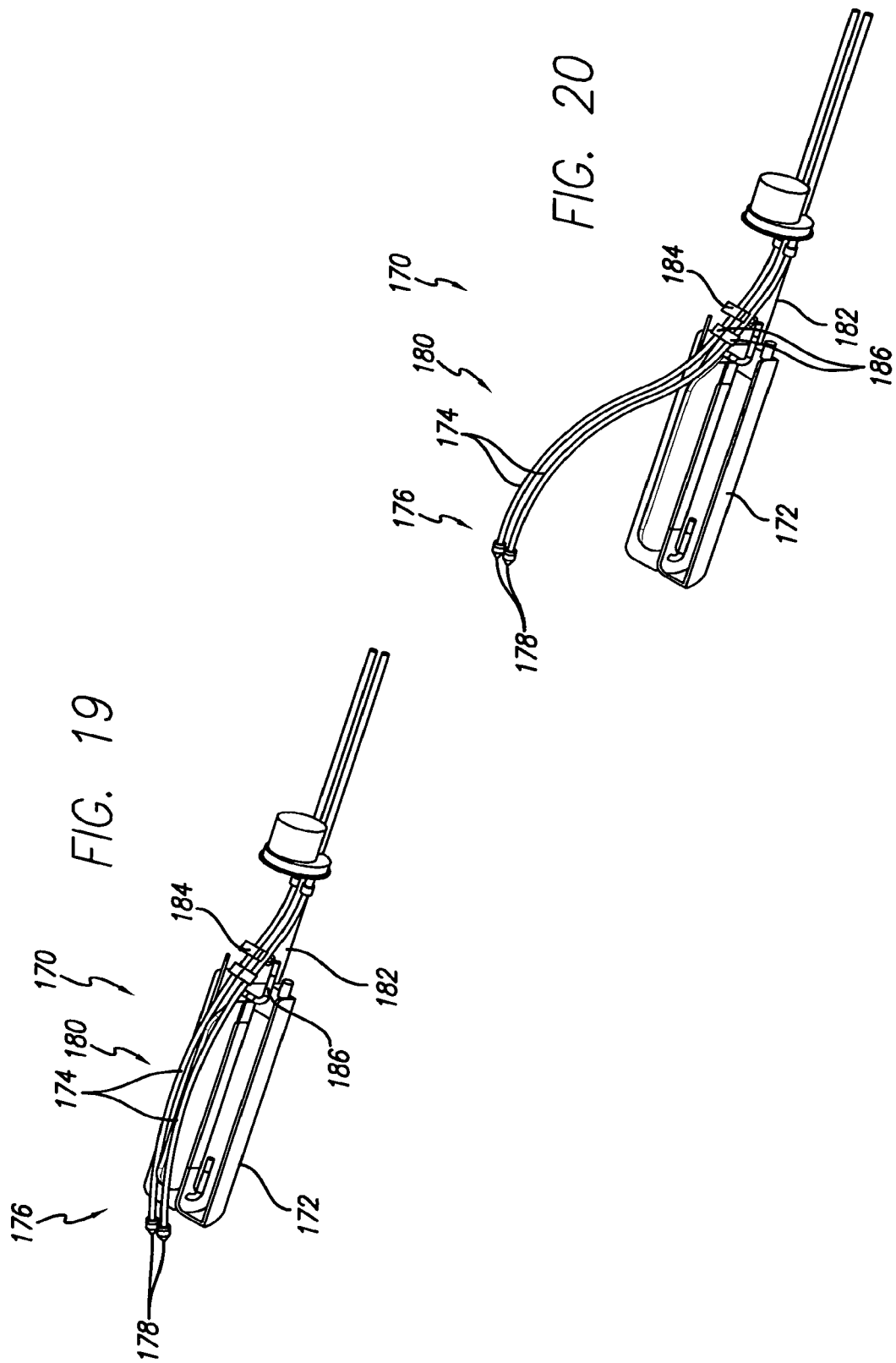

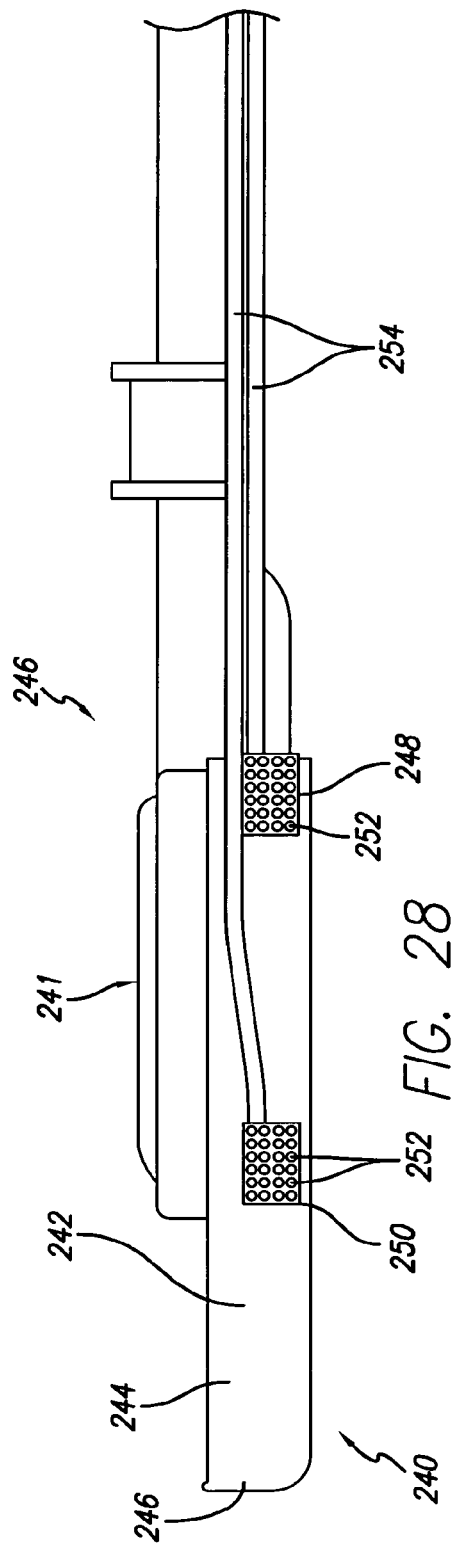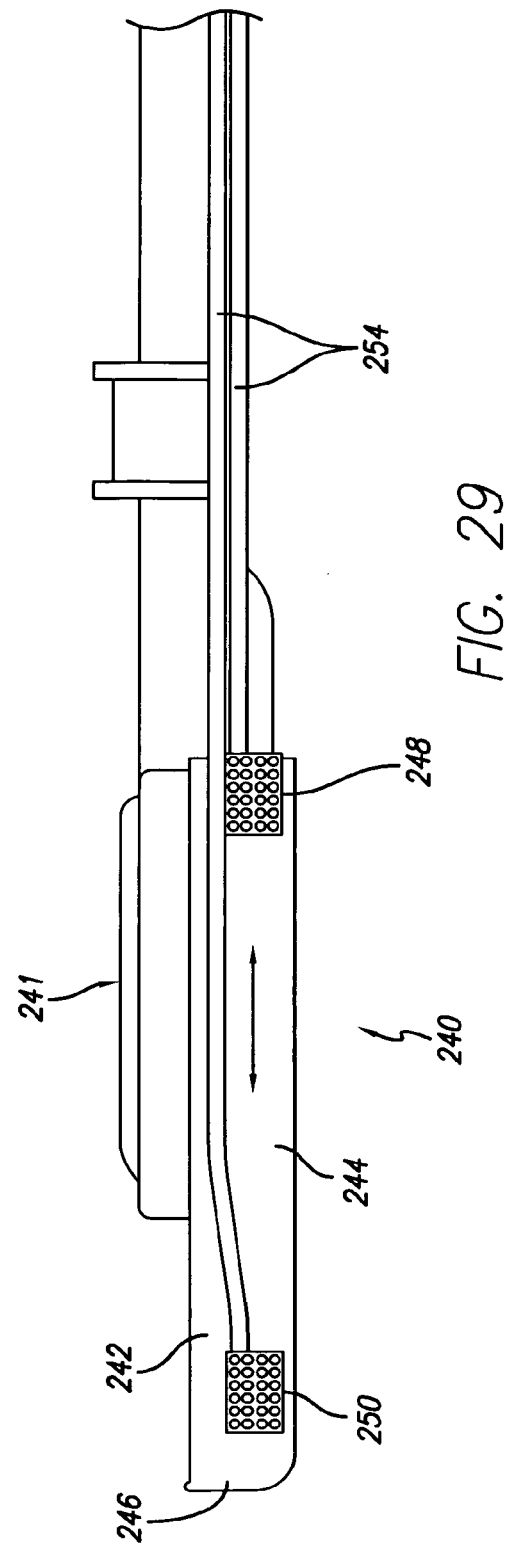

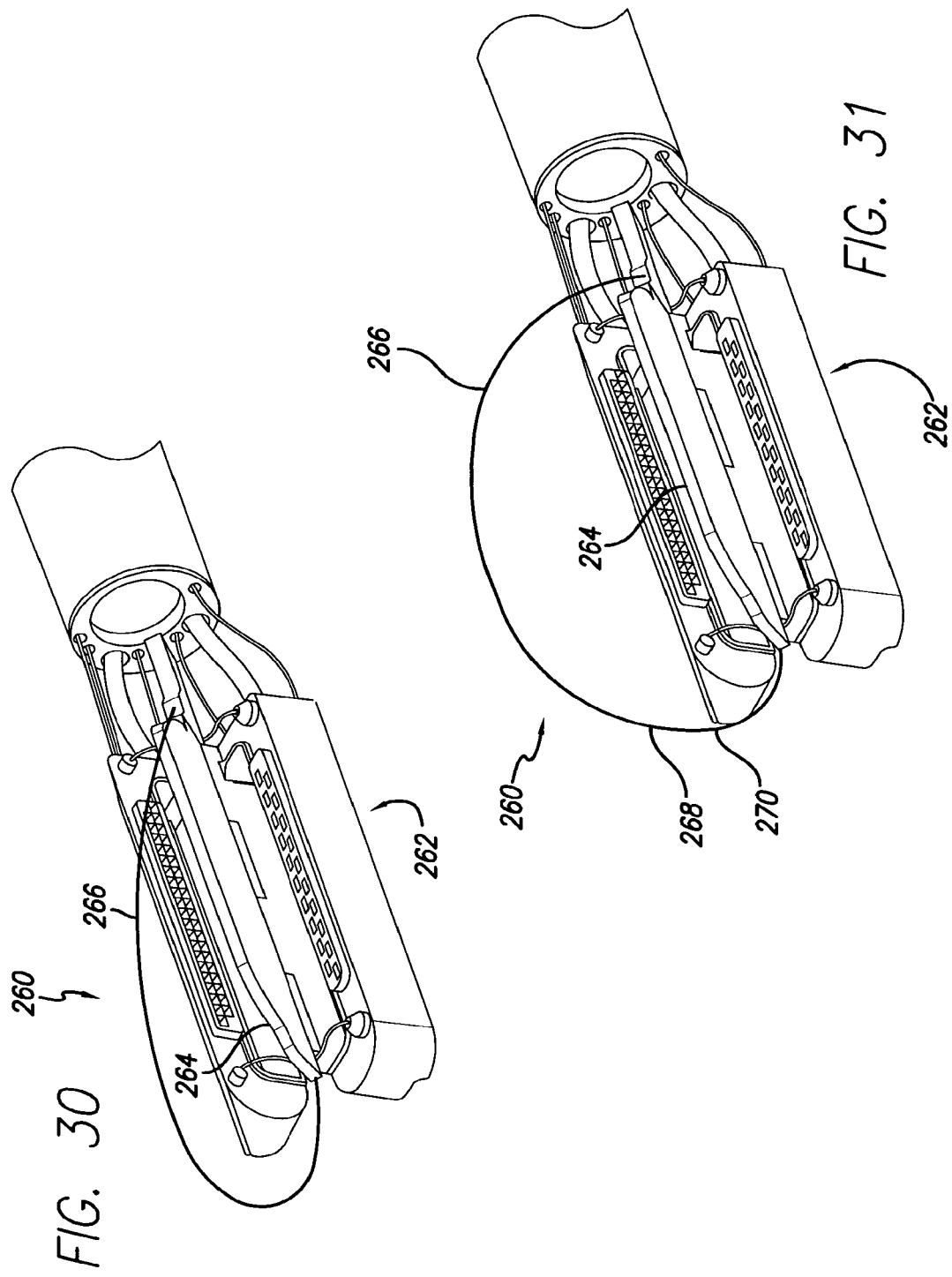

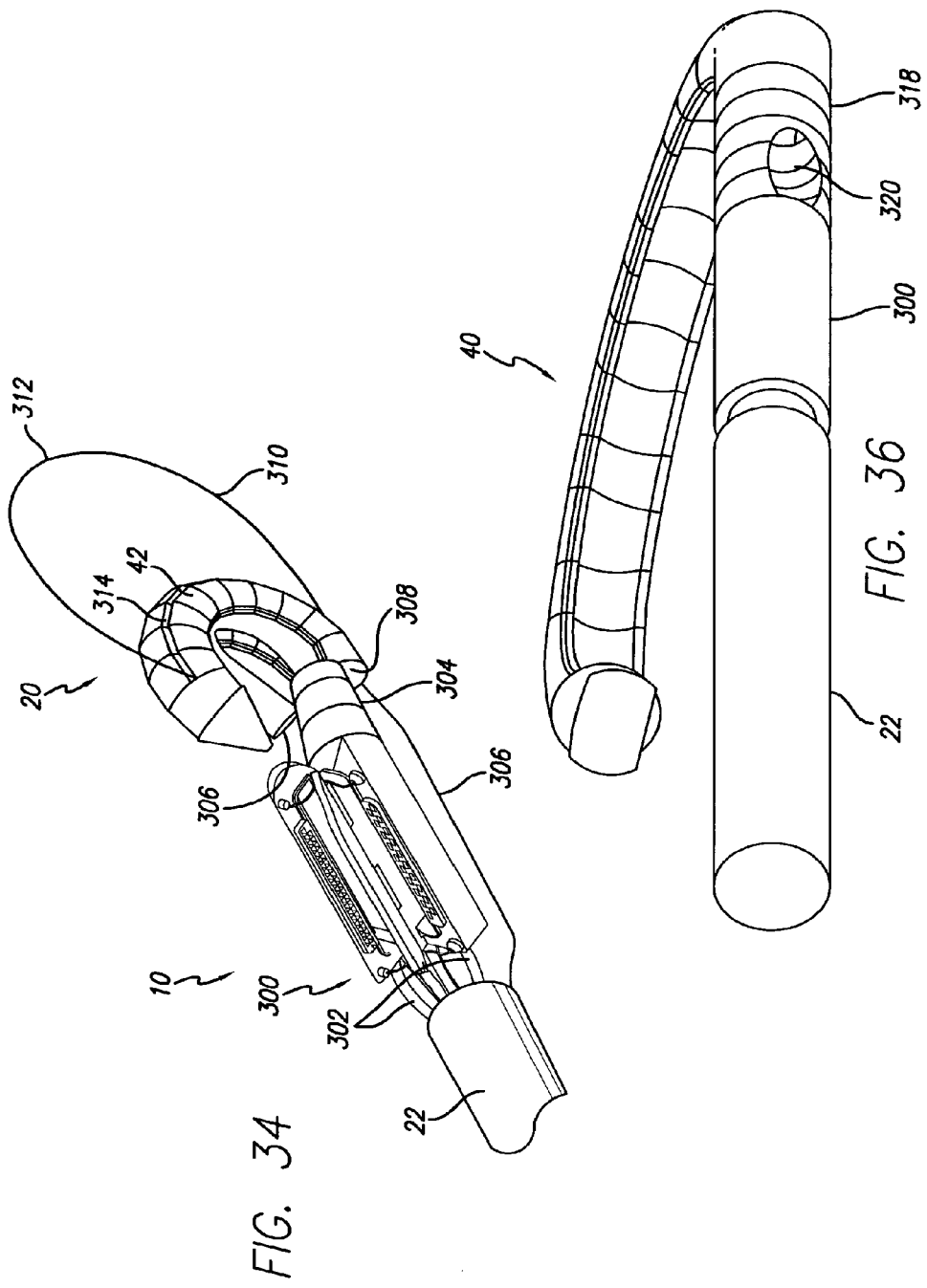

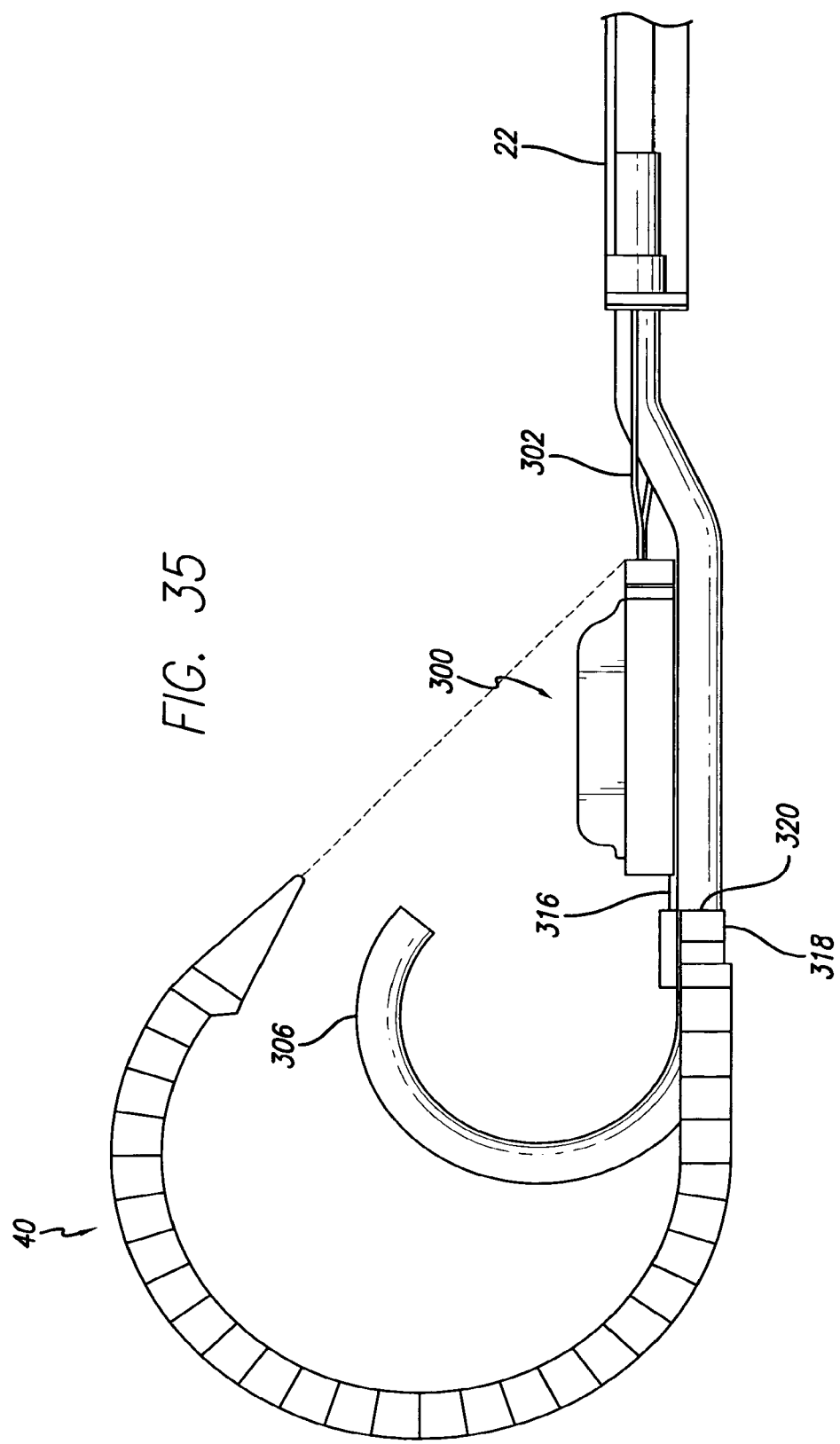

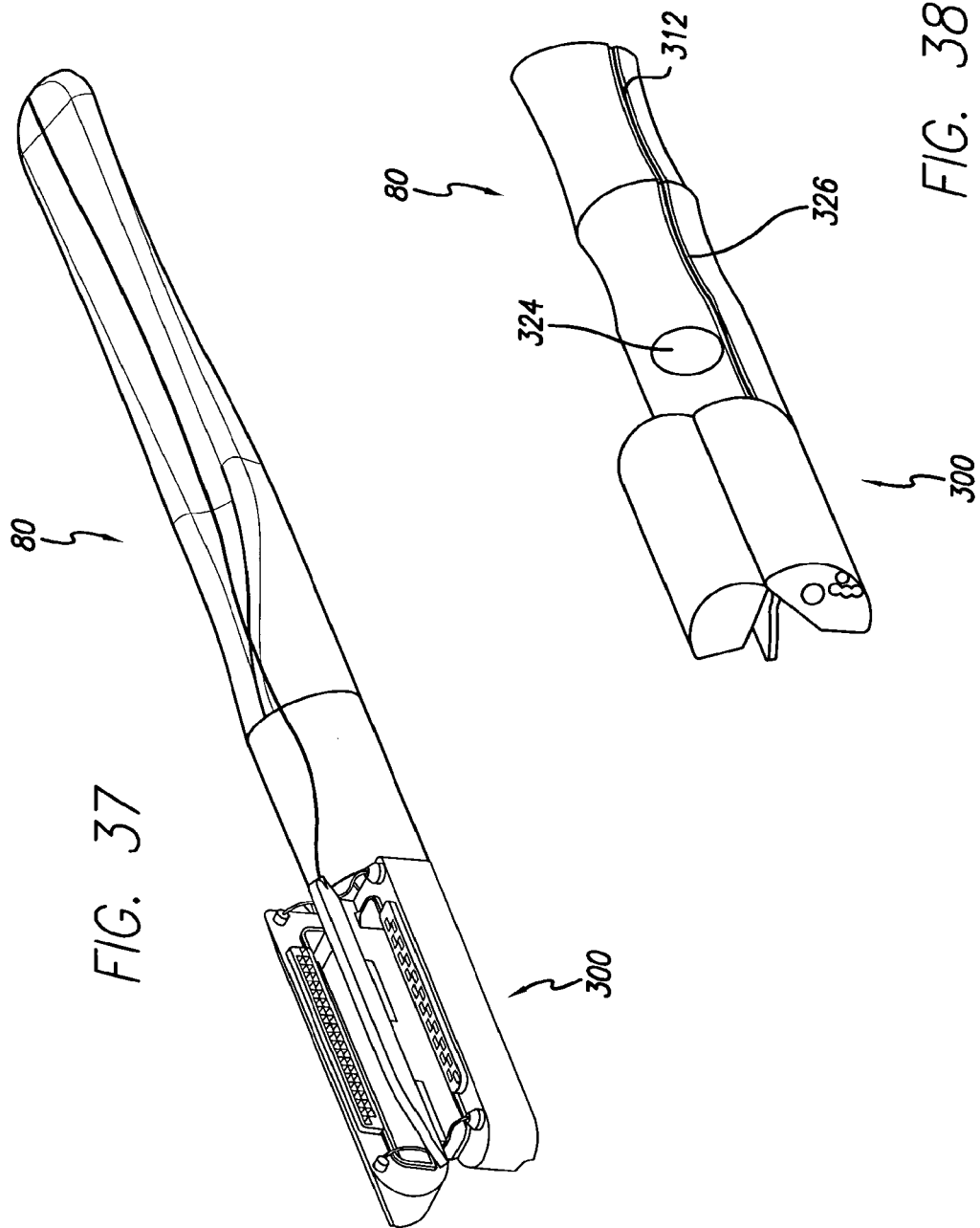

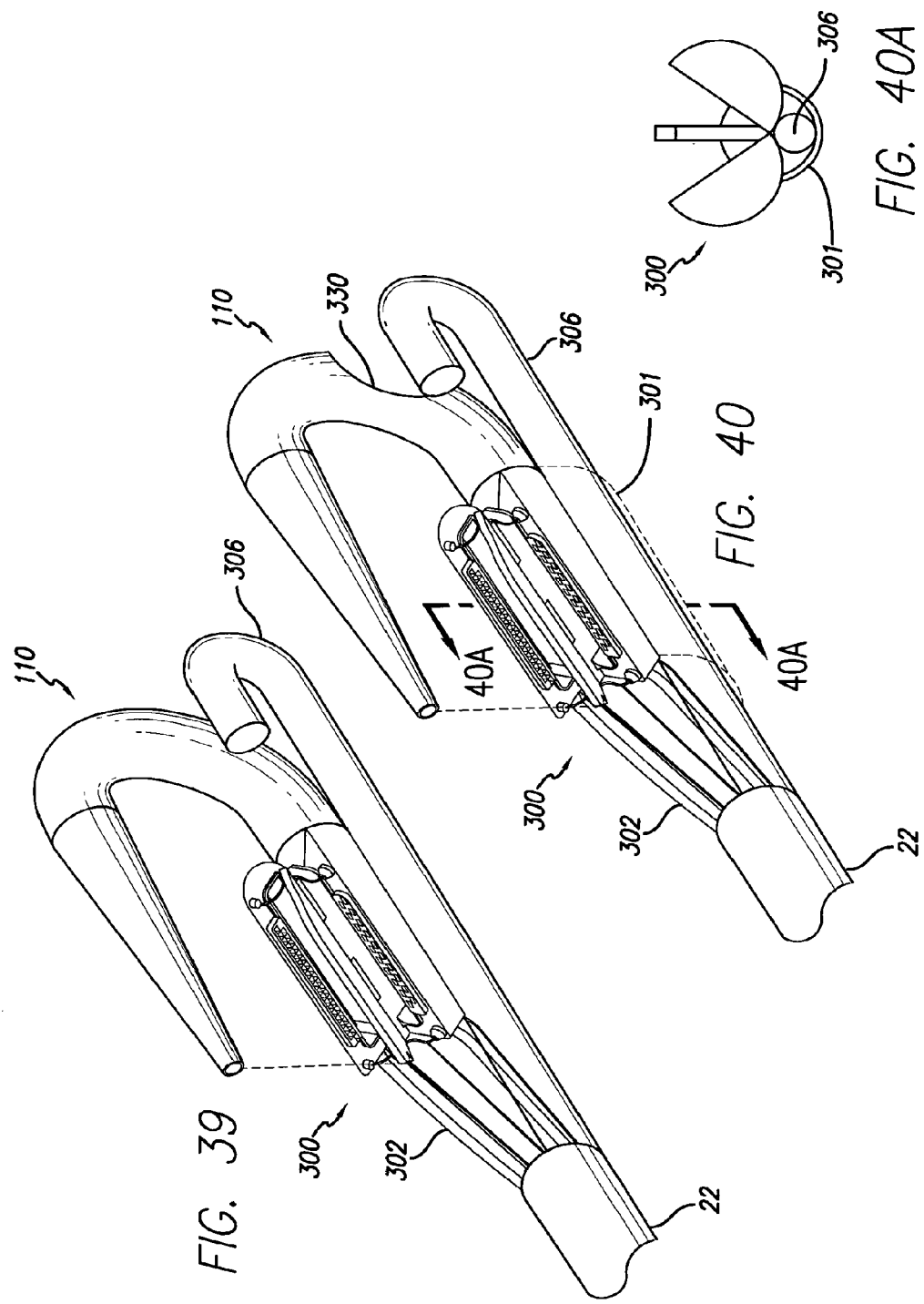

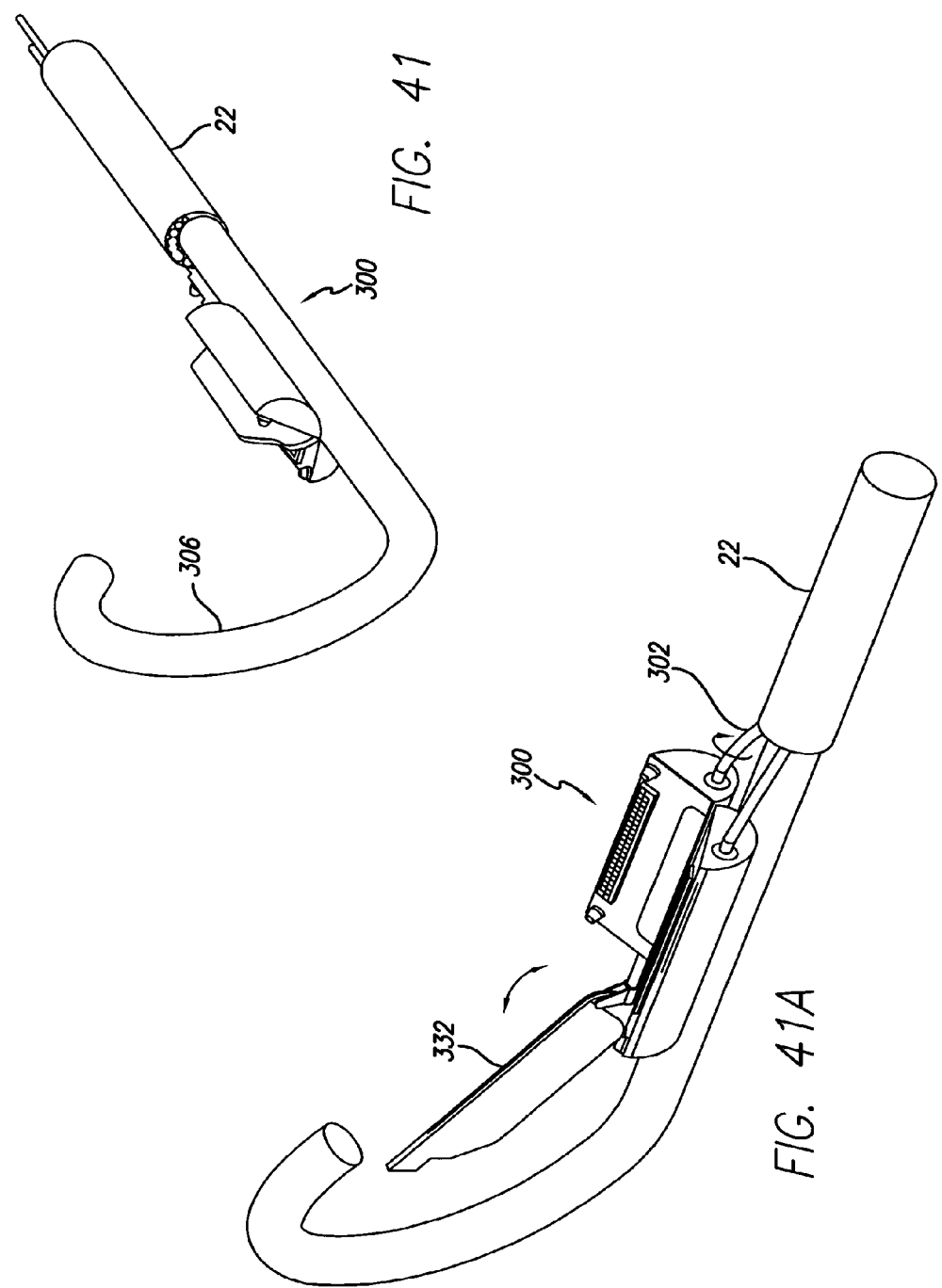

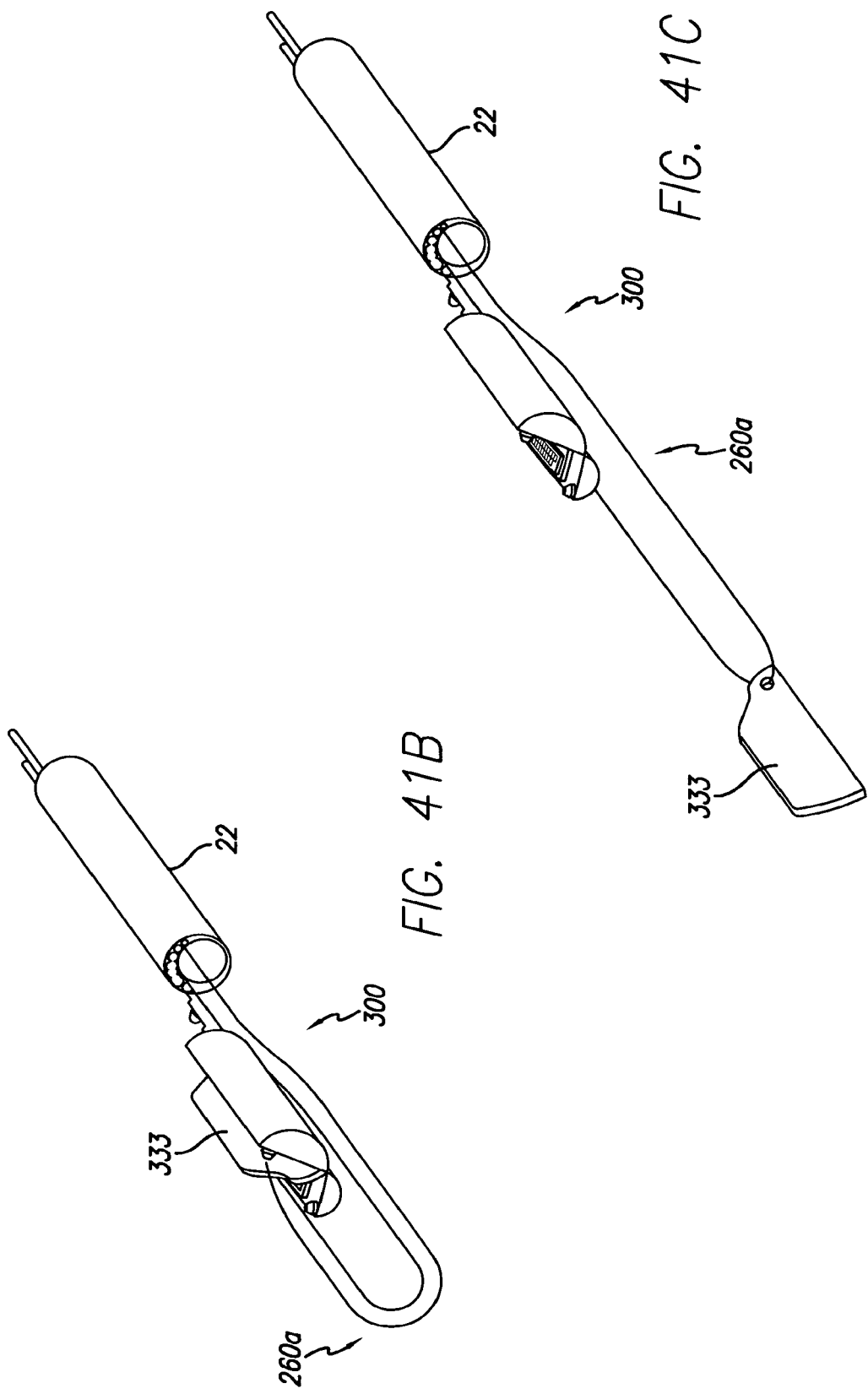

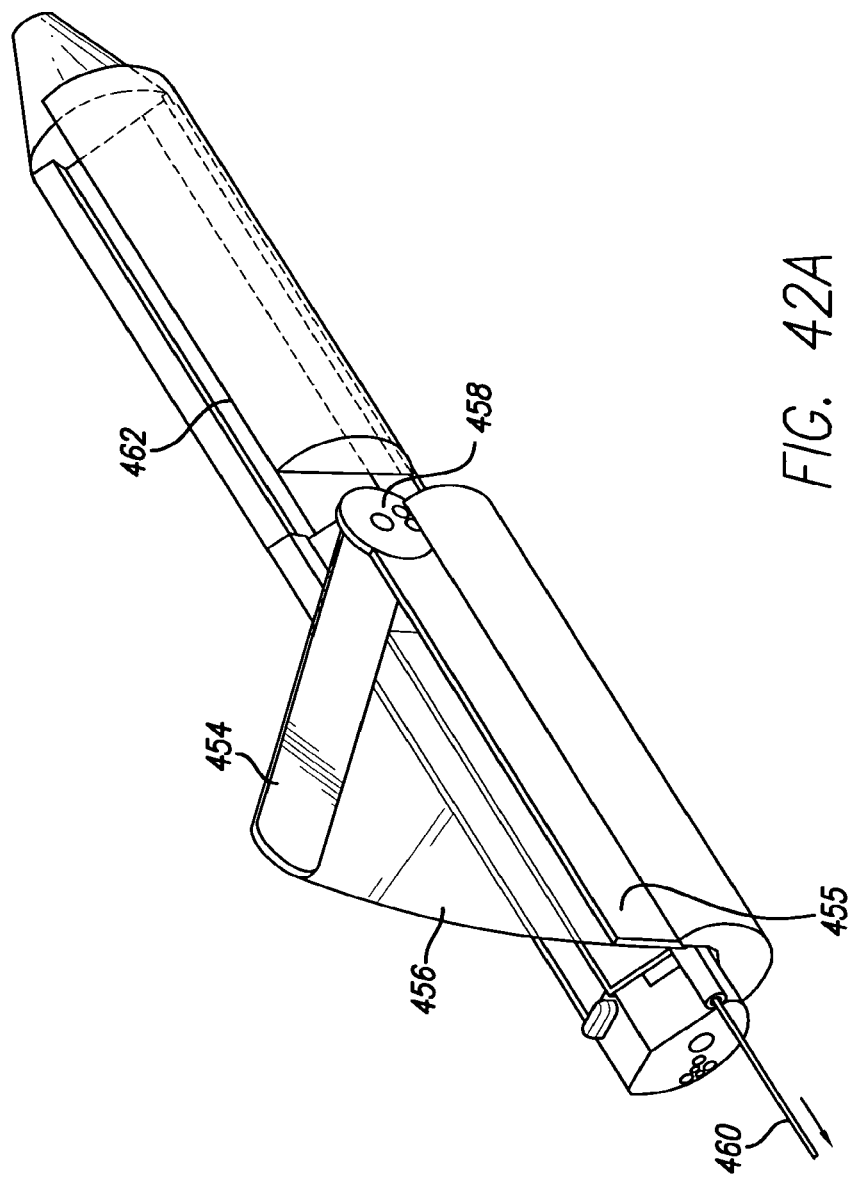

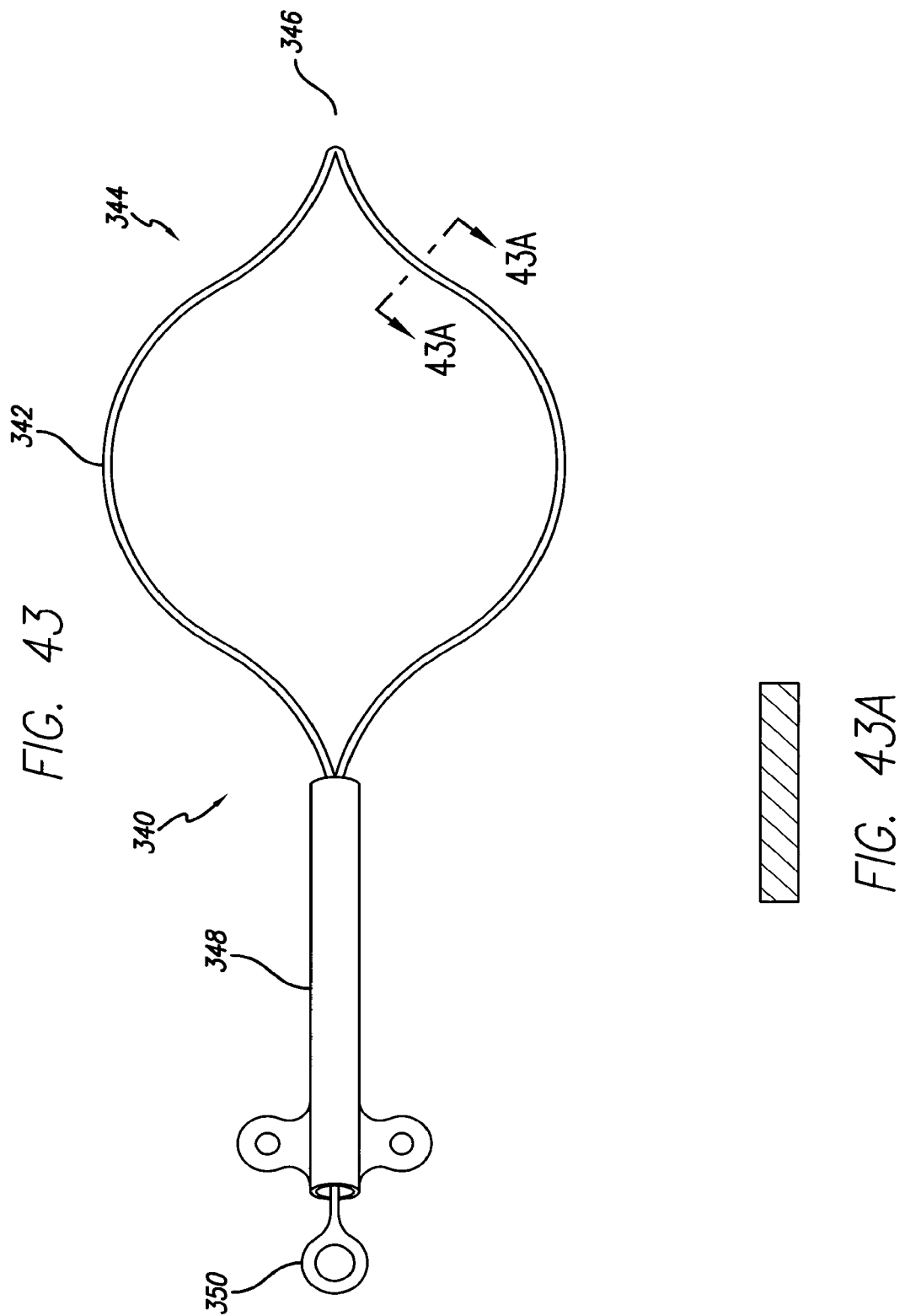

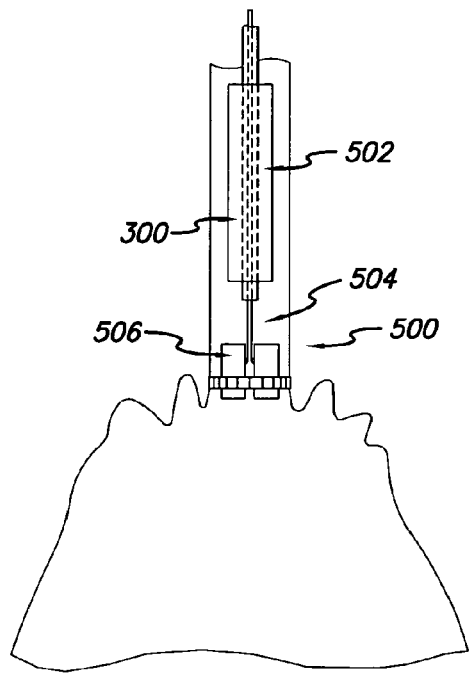
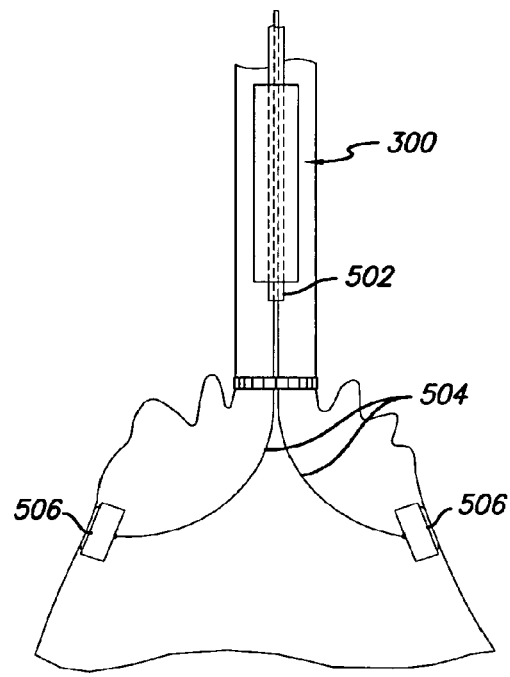
FIG. 55A
FIG. 55B
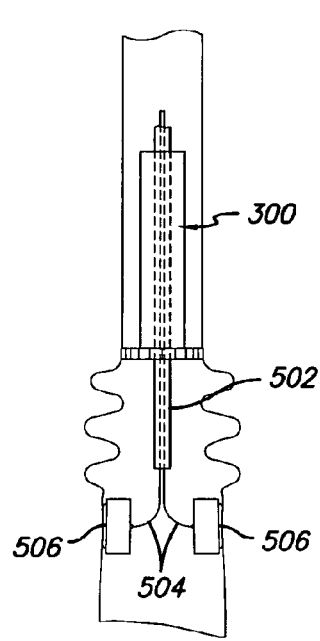
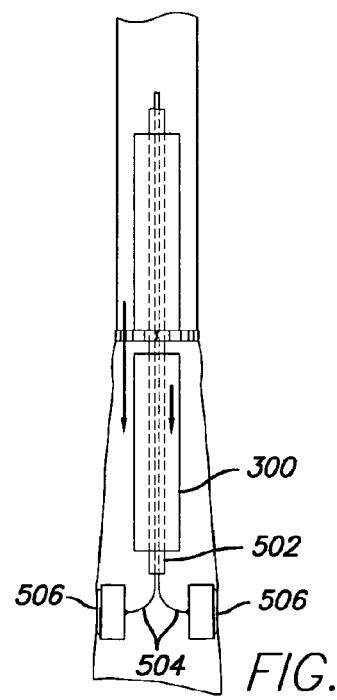
FIG. 55C
FIG. 55D

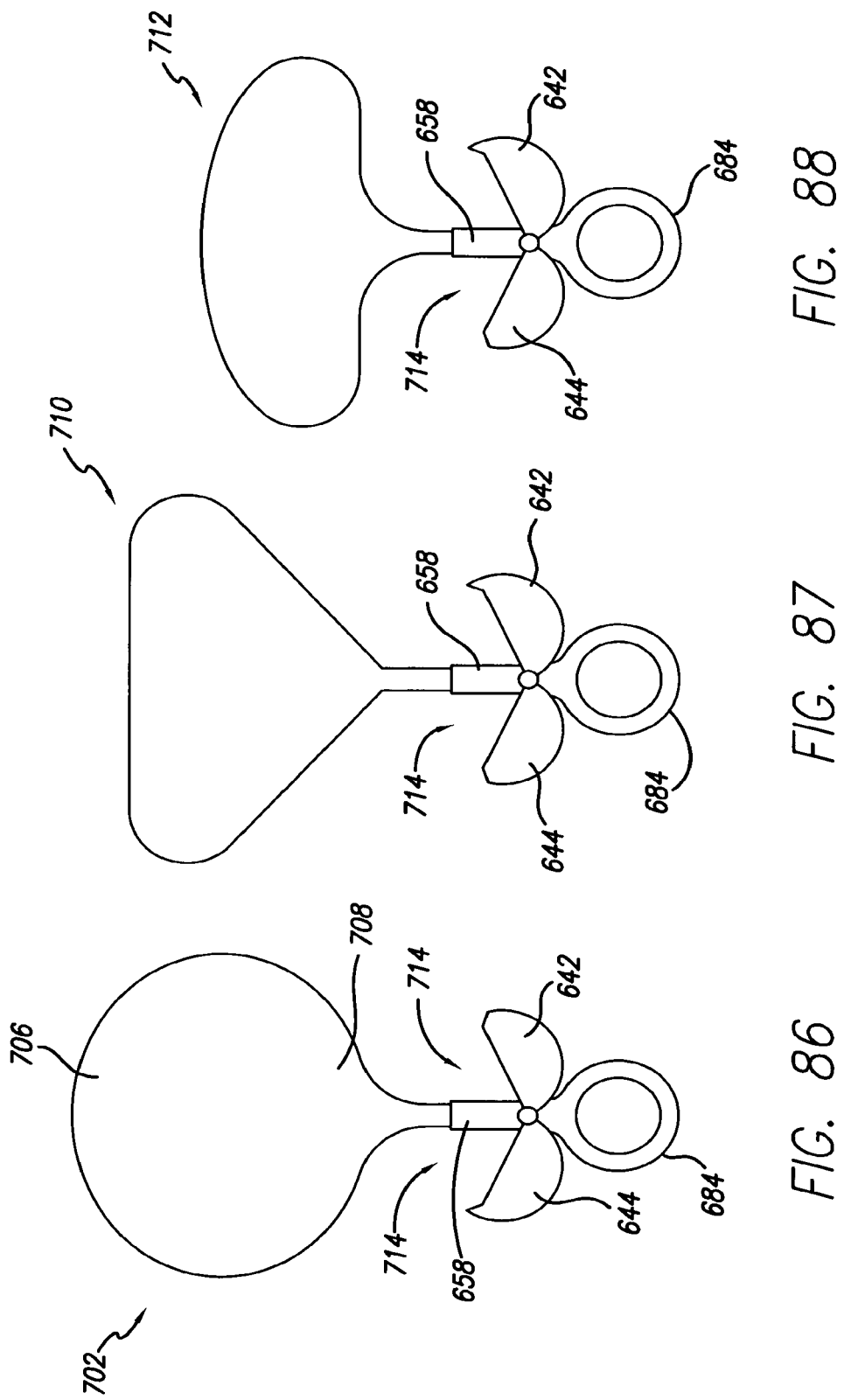

REMOTE TISSUE RETRACTION DEVICE

CROSS REFERENCES TO OTHER APPLICATIONS

This application is a continuation of application Ser. No. 11/955,079 which is a continuation of application Ser. No. 11/282,320 filed Nov. 17, 2005, now issued as U.S. Pat. No. 8,454,503, which is a continuation-in-part of application Ser. No. 10/991,140 filed Nov. 17, 2004, now abandoned, the entire contents of which are incorporated by reference herein.

FIELD OF THE INVENTION

The present invention relates generally to medical apparatuses and methods for remotely retracting or positioning tissue. More particularly, the present invention relates to tools and methods for transoral tissue manipulating and managing within the stomach for treatment of the gastrointestinal tract, including, treatment of GERD, varices, and obesity.

BACKGROUND OF THE INVENTION

At present, there are several surgical procedures for treating obesity, gastroesophageal reflux disease ("GERD"), varices, cancer, hormonal exclusion and the like. To treat these ailments, there are certain procedures that use devices for tissue acquisition and fixation, or gastroplasty, that create a partition within a hollow body organ, such as the stomach, esophageal region, antrum, pyloric region and other portions of the gastrointestinal tract. Currently, there are procedures that advance devices in a minimally invasive manner within a patient's body, e.g., transorally, endoscopically, percutaneously, etc., to create one or several divisions or plications within the hollow body organ. Such divisions or plications can form restrictive barriers within the organ, or can be placed to form a pouch, or gastric lumen, smaller than the remaining stomach volume to essentially act as the active stomach such as the pouch resulting from a surgical Roux-En-Y gastric bypass procedure. Examples of placing and/or creating divisions or plications may be seen in further detail in U.S. Pat. No. 6,558,400; U.S. patent application Ser. No. 10/188,547 filed Jul. 2, 2002; and U.S. patent application Ser. No. 10/417,790 filed Apr. 16, 2003, each of which is incorporated herein by reference in its entirety.

During these gastroplasty procedures, unwanted or non-target tissue, described as "rogue" tissue (tissue that may non-intentionally take the place of normally targeted tissue), for example excess fundus tissues or pleats or folds in the targeted tissue, can become involved with the tissue treatment device that performs a therapy to the stomach tissue. It can be problematic to have non-target tissue being acquired by the tissue treatment device for any number of reasons since the resulting geometry of the altered stomach can be critical to clinical success of the therapeutic procedure. For example, in the case of gastroplasty for purposes of creating a small pouch to mimic the pouch created by the surgical procedure (Roux En y gastric bypass), it may be critical to minimize the possibility of leaving unwanted stomas or openings in the resulting pouch geometry. If the pouch created is not within the clinically preferred range, it may not produce the desired restriction necessary for clinical efficacy. Pleats, folds or non-targeted tissue can disrupt the desired geometry leading to a break down in the pouch itself (dehiscence of fastened region) or undesired clinical results. Control and positioning of the gastric tissue can be difficult due to the stomach's mobility, thickness of the targeted tissue, the abundance and slimy (slippery) texture of the gastric mucosa and the presence of rugae (naturally occurring folds) along the interior of the organ.

Therefore, what has been needed is a device and method for retracting and/or positioning the stomach volume and related organs, to allow certain regions of the stomach to be approximated from within the stomach volume for treatment of various disorders such as obesity, GERD, varices, cancer, hormonal exclusion and the like.

SUMMARY OF THE INVENTION

The present invention provides devices and methods for transorally retracting or positioning the stomach tissue and related organs to allow certain regions of the stomach to be acquired and treated by a tissue acquisition and/or gastroplasty device. For purposes of this specification the term "retraction" or "retracting" refers to direct or indirect movement of tissue either away from or towards a therapeutic element. In some cases, the terms are used to describe holding or blocking tissue where it lays, and providing no appreciable movement of the tissue at all. The term "tissue" may encompass organs, a series of tissue layers, a single tissue layer, regions of tissue, or combinations of all of the above.

The present invention includes a device for managing tissue in an organ, such as the stomach. The device includes a retraction section that can be actuated or deployed, or naturally designed to perform within the stomach to retract, manipulate, or block non-target tissue away from a target region, a region of tissue that is targeted for a medical procedure. In one aspect, the device can be used separately along with a tissue treatment device (device used to perform a therapy to the target region) or the device can be integrated or coupled with the tissue treatment device. Integrating the retraction device with the tissue treatment device means that the two devices are combined into one device. If desired, a gastroscope or endoscope can be used along with the device to view targeted tissue and any surrounding tissue to assist a physician in the procedure. Such an endoscope may also act as the retraction device of the present invention. It is also contemplated that an endoscope or other optical system may be integrated into the treatment device as disclosed. In other aspects of the present invention, more than one retraction device and/or methods may be used in combination with one another to retract or manipulate targeted or non-target tissue. In one aspect, the present invention is performed minimally invasively. The procedure of the present invention may also be performed with laparoscopic assistance, or a combination of transoral and laparoscopic techniques.

The present invention retractor device, either separate or integrated, can perform several functions. First, the retractor device pulls away, blocks or otherwise manages rogue tissue, for example excess fundus tissues or pleats or folds in the targeted tissue, from being involved in the tissue treatment device. Also, the retraction device organizes the targeted tissue by flattening or removing wrinkles and sub-folds from the desired folds of the targeted area. The prospective tissue that will form the plication (or pouch or sleeve if the device is positioned in the organ to achieve that result) can then be suctioned into, grasped or brought to members of the tissue treatment device for therapy. Any flattening of rugae is beneficial during the surgical procedure to achieve durable and precise fastening. Further, the retraction device can support the placing of the tissue treatment device within the stomach in the desired sleeve forming location. The retractor device can help move the tissue treatment device closer to the lesser curve of the stomach or target tissue surface, or the retractor device can be used to initially move the stomach to bring the lesser curve of the stomach or target tissue surface, to the tissue treatment device. The retractor device or feature can also apply axial tension along the lesser curve of the stomach or target tissue region, to achieve both the desired placement of the device and tissue retraction. Another advantage is that the retractor device can retract or accommodate inter-abdominal pressure from the weight of internal organs and the abdominal wall. The retractor should be strong enough to lift and bear the weight of internal organs or it can orient the stomach in a direction that does not encounter such loads. Yet another advantage is that by having a flexible formed element distal to the tissue treatment device, it helps the tissue treatment device pass tortuosity more easily and reduce trauma to surrounding organs such as the upper gastrointestinal tract.

In another aspect, a tissue treatment device having a first jaw opposite a second jaw, integrated with a retractor may also include a collapsible barrier disposed between the first and second pod of the tissue treatment device. An advantage of the collapsible barrier, such as a sail or a balloon, is that it can be raised or extended between the jaws of the tissue treatment device to help manage and control tissue, by directing the tissue into the separate jaws of the tissue treatment device.

BRIEF DESCRIPTION OF THE DRAWINGS

FIG. 1 depicts an embodiment of a retractor device having a channel retractor section at a distal end.

FIG. 2 depicts a handle section of the retractor device shown in FIG. 1.

FIG. 4 depicts one embodiment of a channel retractor section having a roller disposed at a distal end.

FIG. 4A depicts the channel retractor section of FIG. 4 in a curved retraction configuration.

FIG. 4B depicts a channel retractor section having a cone-shaped polymer tip in a curved retraction configuration.

FIG. 7 depicts a split-channel retractor in a straight delivery position.

FIG. 7A depicts a channel link element of the split-channel retractor shown in FIG. 7.

FIG. 9 depicts one embodiment of a flat retractor in a delivery position.

FIG. 10 depicts the flat retractor of FIG. 9 in a curved retraction position.

FIG. 12A depicts an embodiment of a bougie retractor having a D-shaped body.

FIG. 12B depicts the bougie retractor of FIG. 12 in a retracted position.

FIG. 16 depicts one embodiment of a loop retractor positioned within a sleeve for insertion.

FIG. 17. depicts the loop retractor of FIG. 16 extended out of the sleeve into a retraction position.

FIG. 18 depicts another embodiment of a loop retractor having two loops extending out of a sleeve in a retraction position.

FIG. 19 depicts one embodiment of a linear retractor integrated with a tissue treatment device or a working element.

FIG. 20 depicts the linear retractor of FIG. 19 in a retraction position.

FIG. 28 depicts an embodiment of a tissue tensioning retractor positioned along a therapeutic device.

FIG. 29 depicts the tissue tensioning retractor of FIG. 28 with a second pod translated distally relative to a first pod.

FIG. 30 depicts one embodiment of a wire retractor attached to a tissue treatment device.

FIG. 31 depicts the wire retractor of FIG. 30 in a retractor position.

FIG. 34 depicts one embodiment of a retractor device including a primary retractor section and a secondary retractor section integrated with a tissue treatment device.

FIG. 35 depicts one embodiment of a retractor device integrated with a tissue treatment device and shown in use with an endoscope.

FIG. 36 depicts another embodiment of a retractor device integrated with a tissue treatment device, and a bore is shown disposed through the retractor section for the advancement of an endoscope.

FIG. 37 depicts an embodiment of a flat retractor integrated with a tissue treatment device.

FIG. 38 depicts the backside of a flat retractor integrated with a tissue treatment device showing a bore disposed through the proximal end of the flat retractor.

FIG. 39 depicts a bougie retractor integrated with a tissue treatment device in a retracted position in use with an endoscope.

FIG. 40 depicts another embodiment of a bougie retractor having an indentation that is integrated with a tissue treatment device.

FIG. 40A depicts a cross-sectional view taken along line 40A-40A of FIG. 40.

FIG. 41 depicts an endoscope in conjunction with a tissue treatment device.

FIG. 41A depicts an endoscope in conjunction with a tissue treatment device having a hinged septum.

FIG. 41B depicts a wire retractor integrated with a septum of a tissue treatment device.

FIG. 41C depicts the integrated wire retractor of FIG. 41B with the septum removed from the tissue treatment device.

FIG. 43 depicts an embodiment of a flat band spreader shown in a retracted position.

FIG. 43A depicts a cross-section of the flat band spreader taken along line 43A-43A of FIG. 43.

FIGS. 55A through 55D depict an embodiment of an axial retractor integrated with a tissue treatment device.

FIG. 86 depicts a cross-sectional view taken along line 86-86 of FIG. 85.

FIG. 87 depicts an alternative embodiment of a cross-sectional view taken along line 86-86 of FIG. 85.

FIG. 88 depicts another alternative embodiment of a cross-sectional view taken along line 86-86 of FIG. 85.

DETAILED DESCRIPTION OF THE PREFERRED EMBODIMENTS

Figure 3:
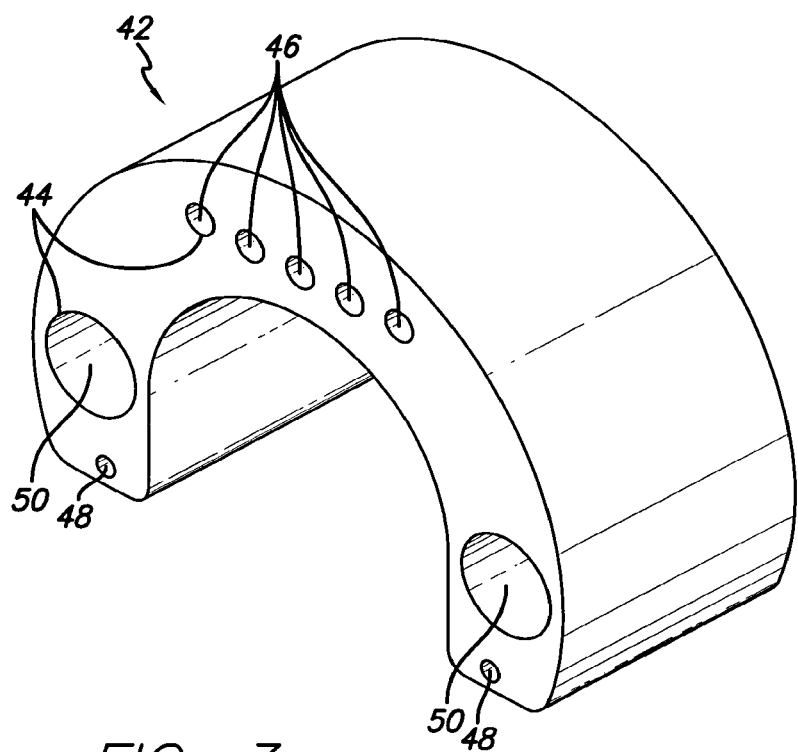
FIG. 3 depicts a perspective view of a U-shaped channel link element.

As will be discussed in detail below, retraction devices retract or stabilize tissue for transoral procedures, such as, stapling, ablation or cell necrosis, mucosal resection, biopsy, drug delivery, tattooing (marking for a later procedure), traumatic procedures such as scoring or abrading tissue to cause stricture, contraction, stimulating healing, or providing hemostasis during procedures. More specifically, the embodiments of the invention are used for transoral tissue retraction alone, or in conjunction with other tools for treatment of the GI tract, including, treatment of GERD, varices, and obesity.

The retraction devices disclosed herein can be used in conjunction with other tools or can even be integrated with other tools forming one device or system of devices. Other tools that can be used with the retraction devices include gastroplasty devices for tissue acquisition and fixation that can be used for creating a partition within a hollow body organ, such as the stomach, esophageal junction, and/or other portions of the gastrointestinal tract. The retraction devices disclosed retract or stabilize tissue so that the gastroplasty device can better perform its function. Types of devices and methods that can be utilized with the preferred embodiments are found in U.S. Pat. No. 6,558,400, which issued May 6, 2003; U.S. Published Pat. App. No. 2004/0006351, which was published Jan. 8, 2004; U.S. patent application Ser. No. 10/797,439, which was filed Mar. 9, 2004; U.S. patent application Ser. No. 10/797,303, which was filed Mar. 9, 2004; U.S. patent application Ser. No. 10/686,326, which was filed Oct. 14, 2003; U.S. patent application Ser. No. 10/417,790, which was filed Apr. 16, 2003; and U.S. patent application Ser. No. 10/279,257, which was filed Oct. 23, 2002; the entirety of each of which are incorporated by reference herein.

Although it is preferred that the retraction devices of the preferred embodiments are advanced within a body transorally, a variety of other methods may be used as well, including transanally, laparoscopically, endoscopically, percutaneously, etc. For ease of reference, the following embodiments will be described as being advanced transorally to the stomach, although the embodiments of the retraction device can be used within other body cavities as well. Throughout the specification the term "proximal" shall mean a point on a body that is nearest the operator of the device, and "distal" shall mean a point on a body that is furthest from the operator of the device.

Retraction Devices

In general, FIG. 1 shows a device 10 for managing tissue in an organ that includes an elongated body 12 having a proximal end 14, a distal end 16, and a working lumen 18 therebetween. A retractor section 20 is disposed at or near the distal end and is adapted to be moveable from a delivery or insertion position to a retraction position for moving or managing the tissue of the stomach. In some embodiments, the device is configured for use with a second therapeutic device, such as an endoscope, a secondary retractor, or a tissue treatment device. There are several different embodiments of the retractor section, and each will be discussed below. As already discussed, the retractor section of the device functions to block, move, push, or pull away unwanted tissue (non-target tissue) from the desired tissue (target area) for transoral procedures. In other words, the retraction or stabilization device is used to manipulate or stabilize targeted or non-target tissue in order to control the target area so that certain procedures, such as forming a staple line, can be performed.

Still referring to FIG. 1, the retractor section 20 is connected to a scope tube 22 forming at least a portion of the working lumen 18 which is connected to a handle portion 24 at the proximal end 14. A protective sheath 23 may also be disposed over the scope tube for protection against injuring the esophagus and related tissue while maneuvering the device down the esophagus to the stomach. The scope tube may be flexible with a bendable shaft made of resilient plastic such as polyurethane, silicone, PVC or a laminate, all optionally reinforced with a wire or braid, or made of a composite construction of more than one material. Another option is that the scope tube can be articulable, such as being formed of a slotted tube connected to a pull wire in the handle portion, to allow the operator to achieve flexion of any portion along the scope tube by operating the pull wire. The scope tube should be of sufficient length to perform a procedure transorally in the stomach of the patient. In some embodiments, the scope tube may range from about 20 cm to about 160 cm in length, and may range from about 5 mm to about 20 mm in outer diameter. A preferable length of the scope tube is generally about 60 cm, and a preferable outer diameter of the scope tube is about 18 mm. The length and diameter of the scope tube can vary depending upon the particular application. The handle portion is used for holding the device and for maneuvering the retractor section.

As best shown in FIG. 2, one embodiment of the handle portion 24 includes a frame 26, a handle grip 28, and a knob 30 for controlling a lead screw 32 and nut 33 that is connected to a slider 34 for curving the retraction section into the retraction position. Pull cables 36 are attached to cable balance adjusting screws and extend through coil pipes 37 along the scope tube and through the retraction section 20 to the distal end 16 of the device 10. As shown in FIG. 1, the scope tube may include organizer rings 38 that hold the pull cables and other wires through the scope tube.

The handle 24 is intended to remotely actuate and hold the position of a cable-actuated retractor. In use, the actuation relies on the relative translation of load between the cable 36 and the coil pipe 37 disposed around it. When the cable is drawn through the coil pipe the cable shortens at the distal end 16 causing curvature of the retractor. The handle uses the lead screw 32 and nut 33 to translate the knob 30 turning motion into axial translation of the load. The lead screw quality provides a mechanical advantage both so that the lesser input loads are needed to actuate and to provide apposition holding ability so that the handle may be released without relaxation of the retractor curvature. The knob is fixed to the lead screw so that it allows an advantage through the diameter of the knob to turn the lead screw. When the lead screw is turned it drives the nut one way or the other. In one direction the lead screw pulls the nut toward the handle and tensions the cable. In the other direction, the nut traveling away from the handle, the tension is released and the retractor is relaxed. A rotational countering of the lead screw torque is provided by slider bearings, located where the slider contacts the slide rails of the frame 26. The lead angle of the screw helix is such that friction will not allow the lead screw to back drive under load and therefore the lead screw is held in position.

The lead nut 33 is fixed to a traveler 39 which allows fixation of the pull cables 36. The pull cables may have crimps attached to their ends which fit directly in crimp seats in the traveler, or the pull cables may pass through the traveler and seat in an adjustment screw to allow length adjustment to the cable positioning. The pull cables may also be passed under a washer and a screw head which fix the cables to the traveler and allow fine tune positioning of the cable length.

The coil pipes 37 extend to the distal end of the scope tube 22 and are attached to coil balance adjusting screws 41 that allow for fine tune adjustments to the length of the coil pipes to match the assembled shaft lengths. The resolving loads from the coil pipes are passed through the adjusting screws to the handle frame 26 and to the knob 30. Thus, a load tensioning ability is provided between the cables and coil pipes.

In one embodiment, the retractor section 20 is a channel retractor 40 (best shown in FIG. 4) and includes U-shaped link elements 42 that are disposed adjacent one another between a proximal collar 43a and a distal collar 43b. A single U-shaped link element is shown in FIG. 3, and the link element includes a number of wire lumens 44. In this embodiment, there are a number of spring element lumens 46 located near the center section of the link element, a pair of cable tension lumens 48 located on opposite sides of the link element, and a pair of forceps lumens 50 located on opposite sides of the link element. It has been contemplated that any number of lumens may be disposed at any location on the link elements. The spring wire lumens may be filled with a spring element 52, such as at least one wire formed of a superelastic alloy, that biases the retractor section into the straight delivery position as shown in FIG. 1. The superelastic alloy may be nitinol or any other superlastic alloy. The spring elements can extend any length through the channel retractor section and be unattached at the distal end, or they can be attached at the distal end to the distal collar 43b. The spring elements can extend through the scope tube 22 to the handle portion 24 at the proximal end 14, or they may only be attached at the proximal collar 43a of the channel retractor section. Pull cables 36 are disposed within the cable tension lumens and are tensioned by turning the knob 30 on the handle to curve the retractor section. The pull cables may extend from the handle 24 of the device and be attached to the distal collar 43b. The forcep lumens may house forceps that can be incorporated into the device. There are many types of forceps that are known in the art, for example, biopsy forceps with alligator jaw made by Olympus, and any forceps meeting the required dimensions of the device can be used. The channel link elements may be made from a variety of materials including clear polycarbonate or any other polymer that has the necessary strength, flexion, bondibility and biocompatibility. In this embodiment, only the wires and cables that are disposed through the lumens keep the channel link elements adjacent one another.

It also has been contemplated that cables may be used in place of the spring element 52 to return the channel retractor 40 from a curved or retraction position to a straight or insertion position. Instead of using a superelastic wire that biases the retractor section into a straight configuration, the cables (or cable) disposed through the spring element lumens 46 located near the center of the U-shape, can be pulled proximally by the operator to return the link elements to the initial straight configuration. The retractor section can only be straightened by the spring elements or cable after the pull cables 36 have been loosened by the knob 30 at the handle 24.

In one embodiment, the distal end 16 of the elongated body 12 includes an atraumatic tip 54 to help prevent injury to the tissue inside an organ such as the esophagus or the stomach. It is contemplated that the atraumatic tip can be a roller 56, or a shaped polymer tip 58 (see FIG. 4B), or coiled tip similar to the construction of a guide wire as is known in the art. The polymer tip can include a taper and/or a rounded shape. The roller or polymer tip can be connected through any method known in the art to the distal collar 43b of the channel retractor 40. The tip can also terminate like that found on a commercially available endoscope, such as the endoscope manufactured by Olympus with Model No. GIF-P140.

Referring to FIG. 4, the channel retractor 40 is shown in the delivery position with a roller 56 attached at the distal end 16. In the delivery position, the channel link elements 42 are designed and positioned next to one another so that a wedge shaped gap 60 exists between adjacent channel link elements. These wedge shaped gaps allow the channel retractor to curve into a retraction position when the pull cables 36 are tensioned at the proximal end 14. FIG. 4A shows the channel retractor in a fully retracted position so that the wedged shaped gaps between the link elements are closed. In this position, the device can retract, block, push or move unwanted tissue away from a target area. As the channel retractor moves into the retracted position, the distal tip may come into contact with and press against the stomach wall. Once in the retracted position the arc of the channel retractor can be pressed against the stomach wall, thereby pushing and/or stretching the stomach wall. Also, the operator may push, pull, or rotate the device itself while the channel retractor is deployed within the stomach to further maneuver the stomach wall, or to position the channel retractor into a more desirable position within the stomach. The channel retractor is also shown in the retracted position in FIG. 4B, but in this embodiment, there is a shaped polymer tip attached to the distal end. After a surgical procedure is completed and it is desirable to return the retractor section to its straight delivery position in order to remove the device from the patient's body, the knob 30 on the handle portion 24 can be turned to loosen the pull cables, and the biasing force of the spring element 52 returns the retractor section to its delivery or insertion position. The cable tension wires can be adjusted to provide the desired curvature or arc of the retractor section. The arc formed by the retractor in the retraction position may have a diameter in the range of about one inch to about sixteen inches.

Figure 5A:
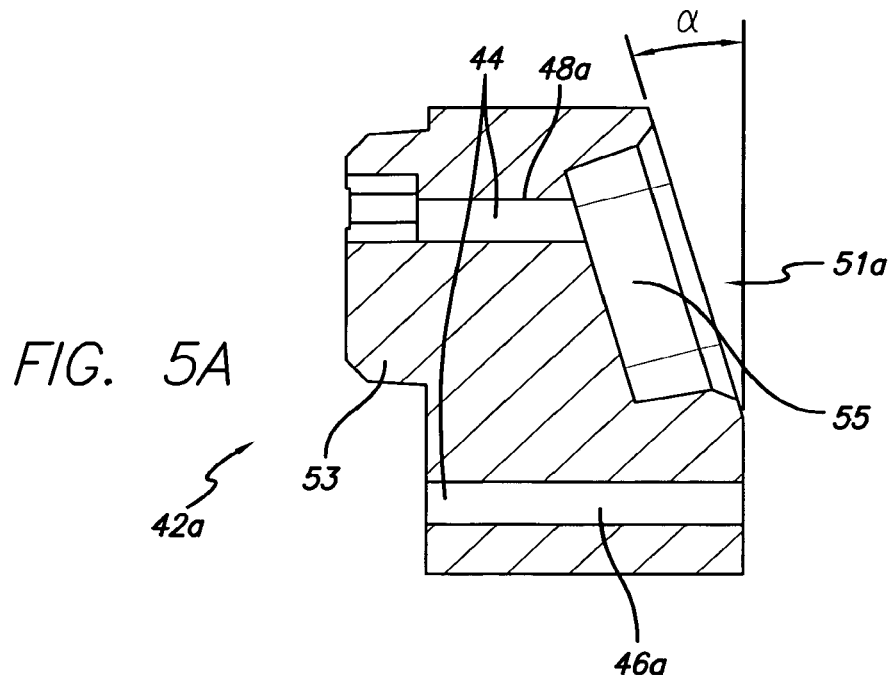
FIG. 5A depicts a cross-sectional view of one embodiment of a proximal channel link element.
Figure 5B:
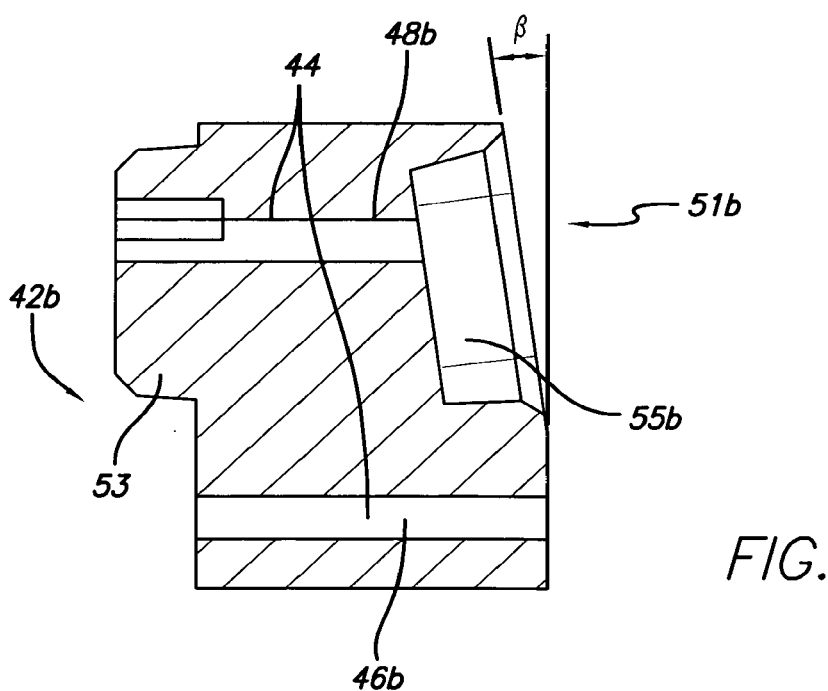
FIG. 5B depicts a cross-sectional view of one embodiment of a distal channel link element.

FIGS. 5A through 5D show another embodiment of a channel retractor 40a. As shown in FIG. 5A, a proximal channel link element 42a is shown in cross-section to include a boss 53 on one side of proximal link element and an indentation 55 on the opposite side of the proximal link element. The proximal link element also includes a beveled face 51a on the opposite end of the boss. An angle α of the bevel is shown to be approximately 15°, however, the angle may range from about 5° to about 25°. The higher the angle of the bevel, the more the retractor can curve as adjacent links bend or arc toward each other. Lumens 44, such as cable tensioning lumen 48a and spring element lumen 46a, are to be disposed within the proximal link element, and the link element may include multiple lumens disposed throughout the body of the link element. For example, there may be two lumens located through the link element on opposite sides of the boss and one lumen located through the boss (cable tensioning lumens), and one or two lumens located underneath the boss (spring element lumens). FIG. 5B shows a distal link element 42b that is similar to the proximal link element 42a except that the beveled face 51b includes an angle β. In the embodiment shown, angle β is approximately 8°, however, the angle may range from about 3° to about 24°.

Figure 5C:
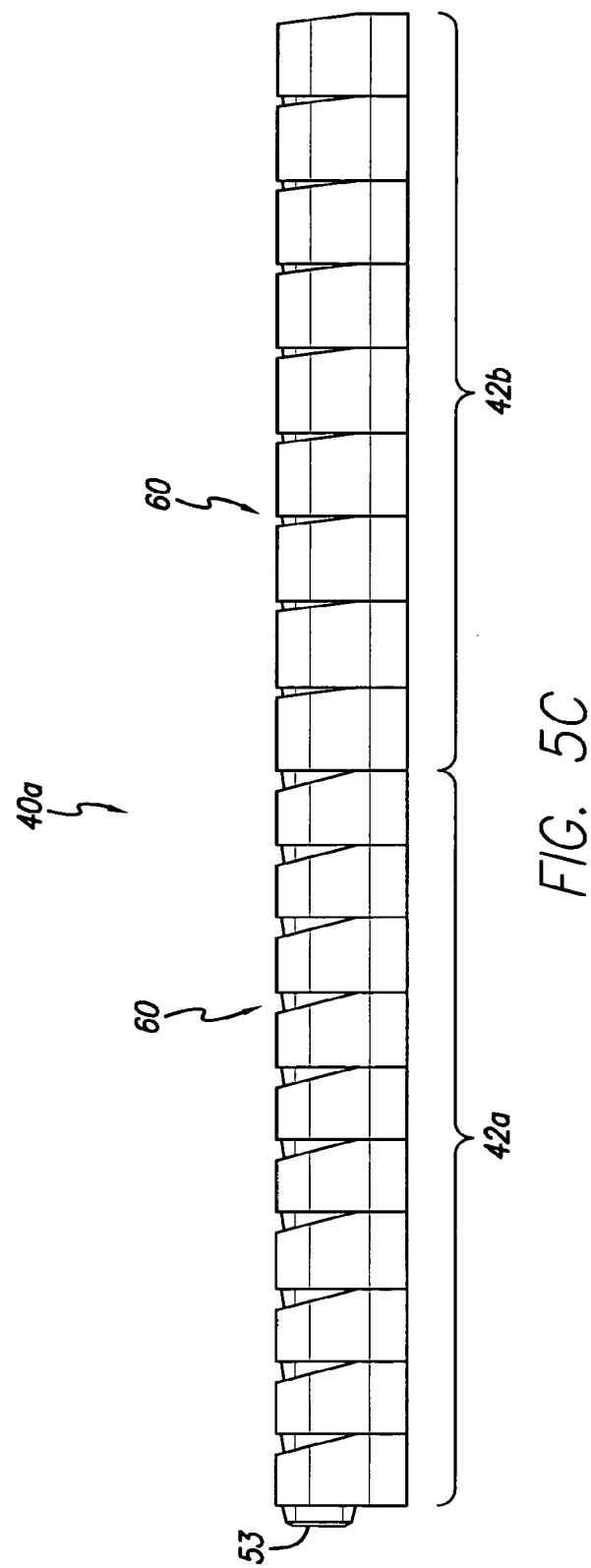
FIG. 5C depicts one embodiment of a channel retractor section formed with proximal and distal channel link elements in a straight insertion configuration.
Figure 5D:
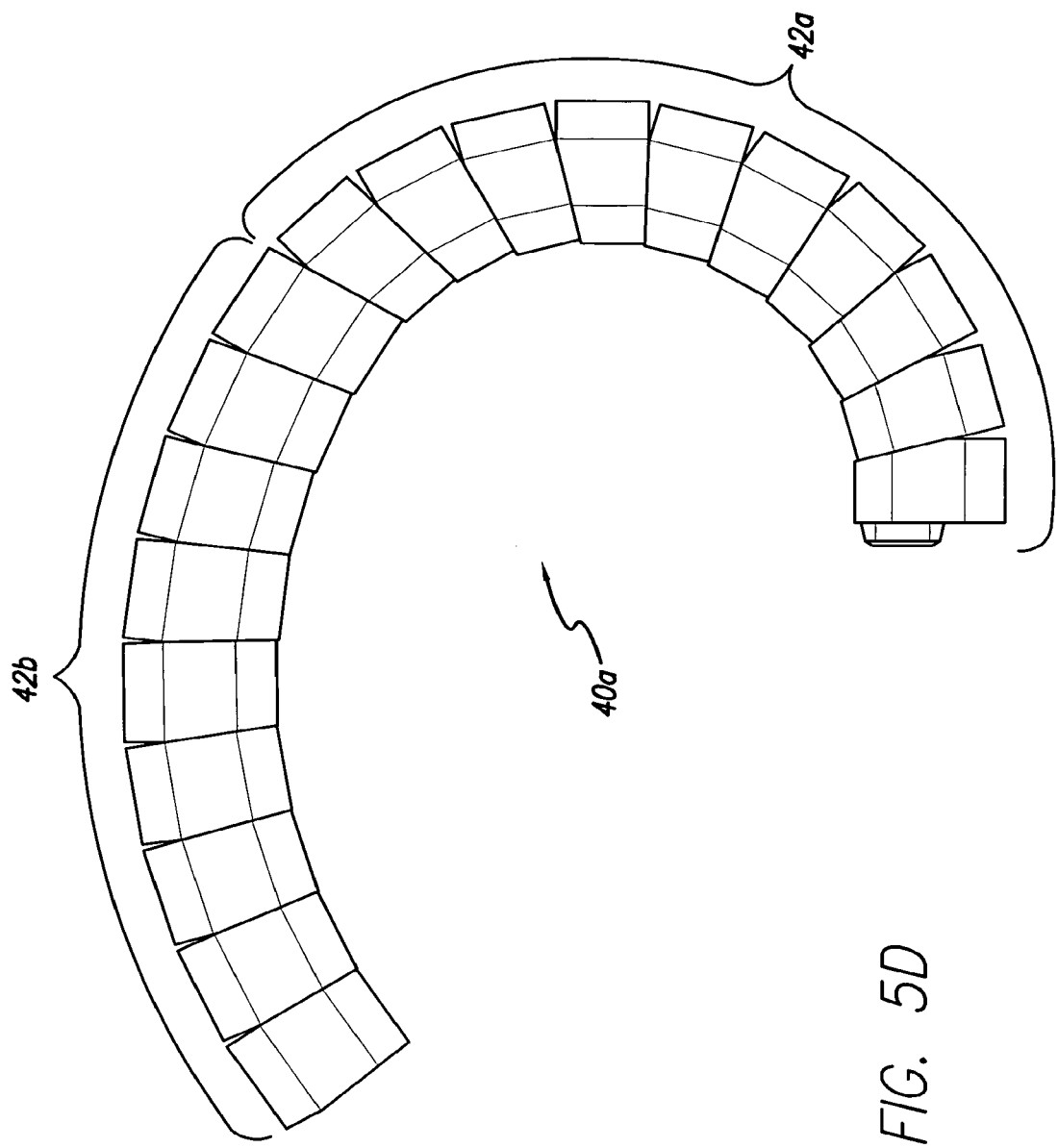
FIG. 5D depicts the channel retractor section of FIG. 5C in a curved retraction configuration.

FIG. 5C shows the channel retractor 40a including several proximal link elements 42a and several distal link elements 42b joined together. In one embodiment, there are ten proximal link elements and nine distal link elements, although the number of link elements may be varied to effect the diameter of the retractor section in the retracted state. The beveled faces 51a and 51b create gaps 60 between adjacent link elements. Because the angle of the beveled faces 51a and 51b are different, the size of the gap between distal link elements is smaller than the gap between adjacent proximal link elements. By tightening pull cables through the cable tensioning lumens 48a and 48b of the link elements 42a and 42b, the pull cables actuate the retractor section by foreshortening the gaps between adjacent link elements, forcing the retractor section to curve into the shape shown in FIG. 5D. The angle of curvature of proximal section is greater than the angle of curvature of the distal section because of the different gap sizes between adjacent link elements. Once in the retracted position, the bosses 53 of the link elements are fitted within the indentations 55 of the adjacent link element. The boss is preferably tapered or rounded so that it does not lock within the indentation of the adjacent link element, which allows the boss to slide in and out of the indentation of an adjacent link element when the retractor is actuated into and out of the retracted or curved position. The retractor section shown in FIG. 5D can be straightened by pulling on a cable located in the spring element lumens or by allowing the biasing force of a spring element to return the retractor section to its straight delivery state.

Figure 6:
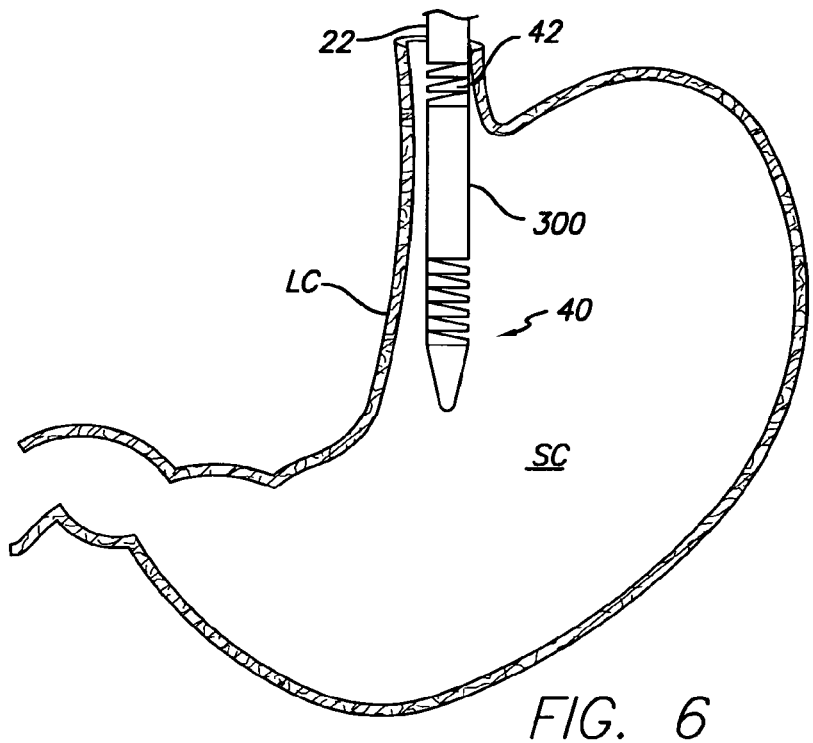
FIG. 6 depicts an embodiment of a tissue treatment device positioned within a stomach cavity having channel link elements disposed proximal to the tissue treatment device.
Figure 6A:
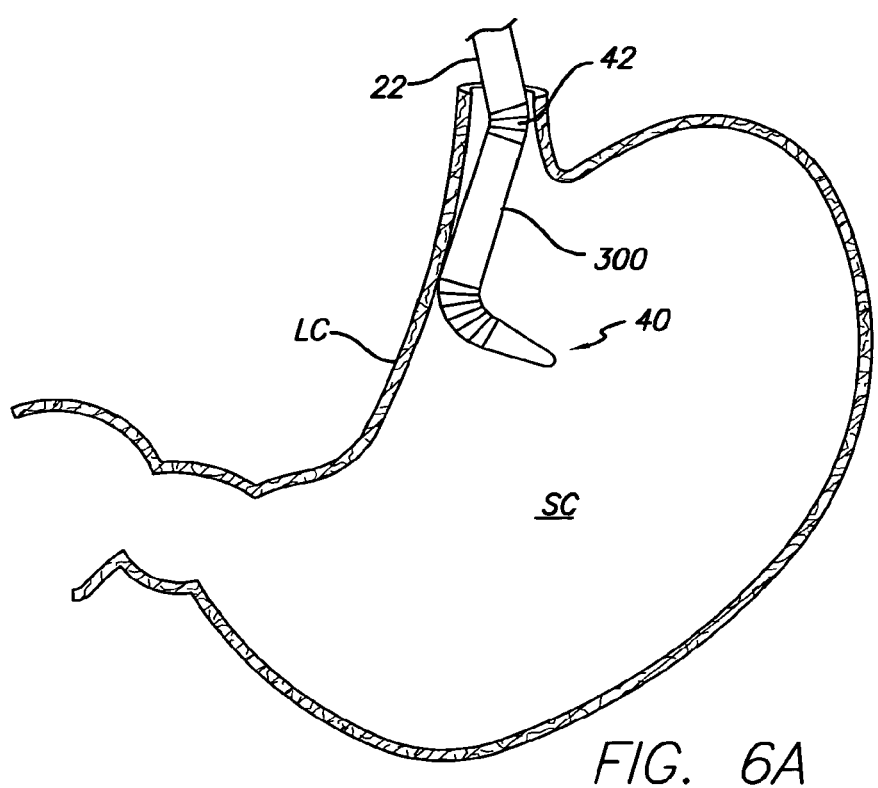
FIG. 6A depicts the tissue treatment device of FIG. 6 with the channel link elements actuated to bend the tissue treatment device toward the lesser curve of the stomach.

The channel link elements 42, 42a, and 42b can also be disposed proximal of a tissue treatment device 300 to better position the tissue treatment device inside the stomach cavity. FIG. 6 shows three channel link elements 42 positioned between the distal end of the scope tube 22 and the proximal end of the tissue acquisition device. The device is shown within the stomach cavity ("SC") near the lesser curve ("LC"). The channel link elements are positioned so that when actuated, they will bend and move the tissue acquisition device closer to or even in contact with the lesser curve as shown in FIG. 6A. Any number of channel link elements may be used for this purpose, and it is preferred that three link elements be used. The channel link elements are actuated with a pull cable as described above with respect to the channel link elements 42, 42a, and 42b. A retractor section, such as the channel retractor 40, may also be added to the distal end of the tissue treatment device as shown in FIGS. 6 and 6A, and the same pull cable may be used to actuated the proximal link elements at one end of the tissue treatment device and the channel retractor at the other end of the tissue treatment device. Alternatively, such angled sections of the device may be configured with other types of linkages or hinge points, such as the flexible breach or bridge portion referred to as element 302 in FIG. 40, and further described in U.S. patent application Ser. No. 10/686,326 for application with similar therapeutic devices, previously incorporated by reference.

Figure 8:
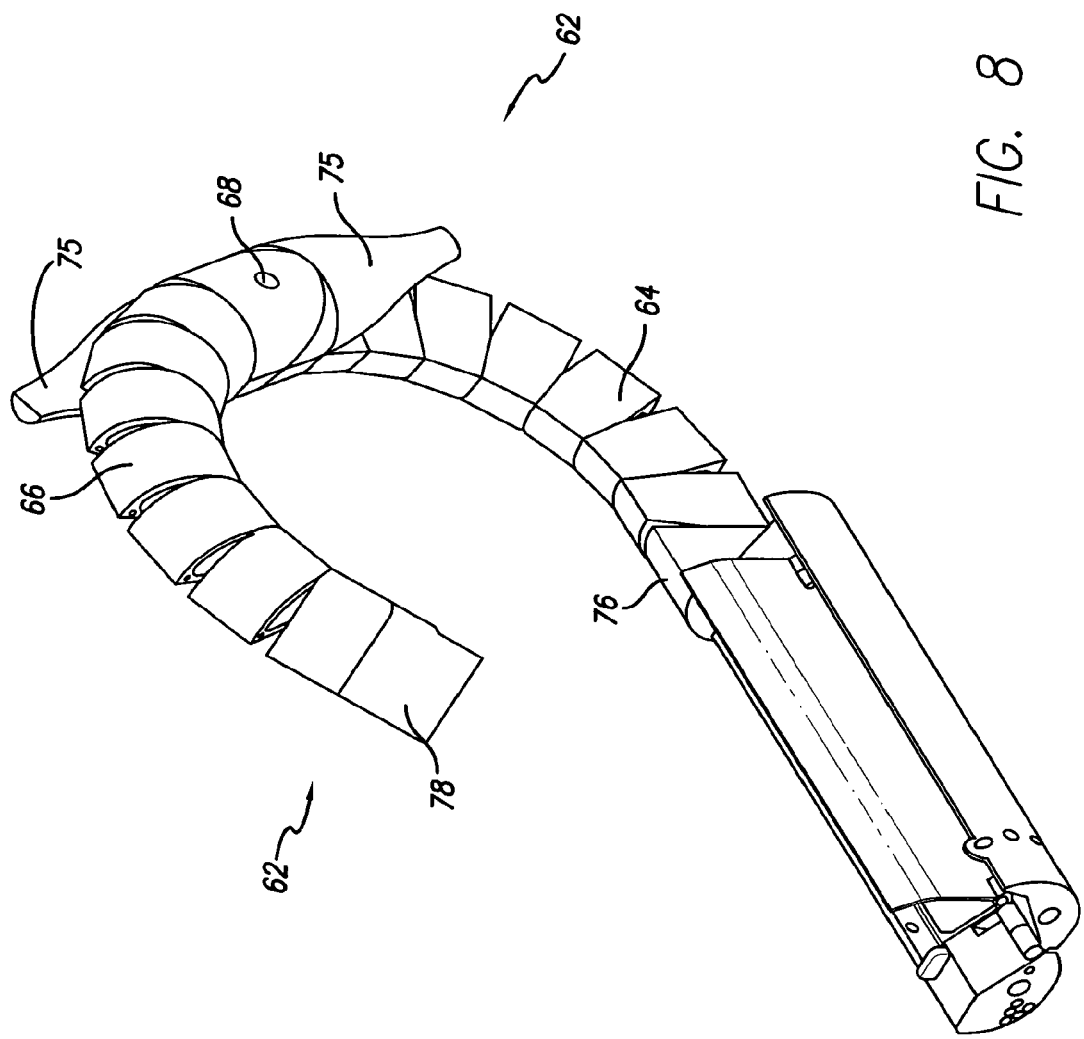
FIG. 8 depicts a perspective view the split-channel retractor in a curved retraction position.
Figure 8A:
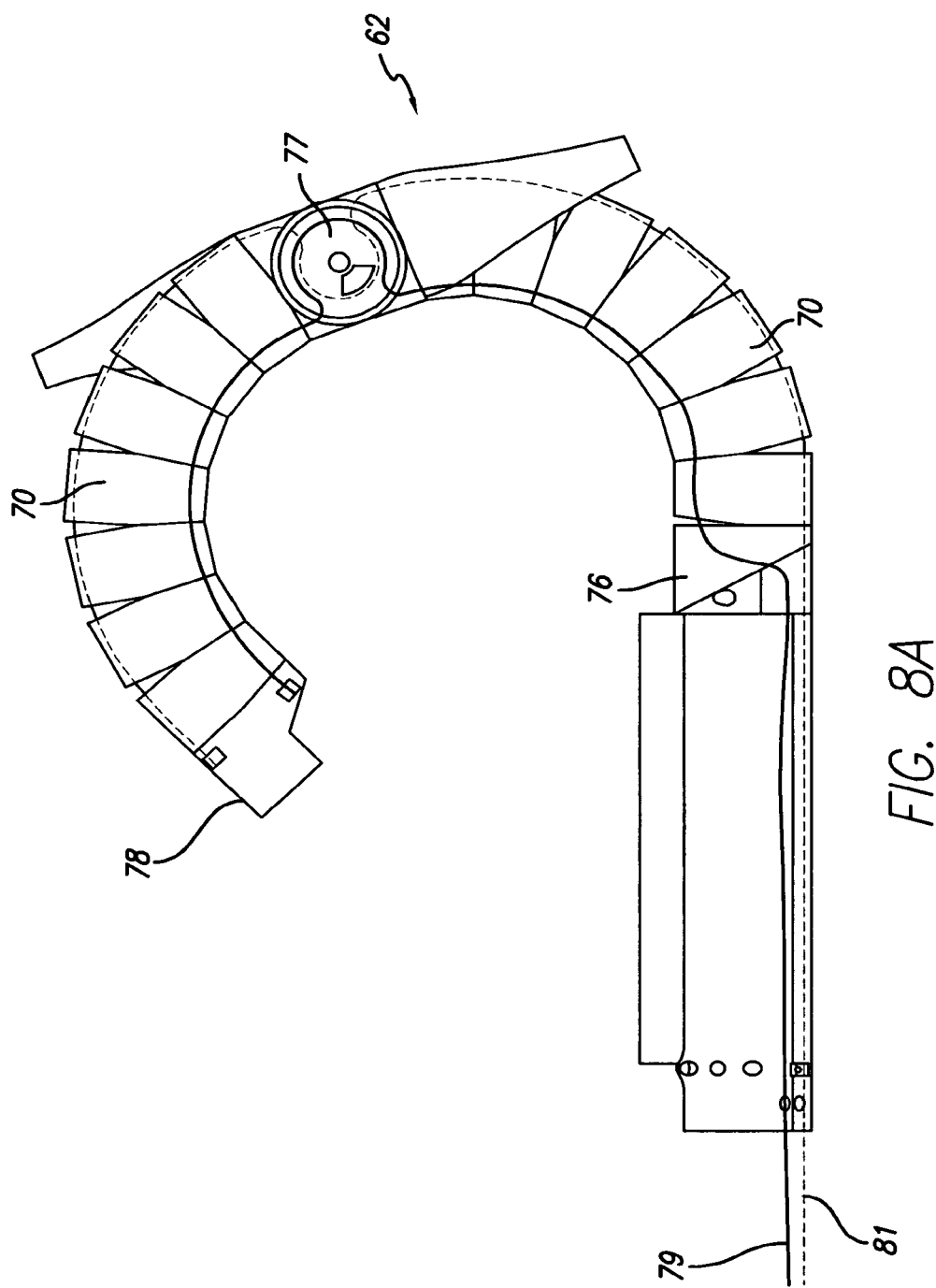
FIG. 8A depicts a side elevational view of the split-channel retractor of FIG. 8.

FIGS. 7 through 8A show another embodiment, where the retractor section 20 is a split channel retractor 62. The split channel retractor includes a first section of link elements 64 and a second section of link elements 66 that are attached together at a pivot 68. In the straight or insertion position shown in FIG. 7, the first and second sections of link elements are folded together in a side-by-side relationship. In this embodiment, the length of the retractor section during delivery may be half of the length of the channel retractor 40, which may allow for easier positioning and deployment within the stomach cavity. It is preferred that the length of the first section 64 and second section 66 be equal, wherein the pivot is in the middle of the retractor section, however, the two sections 64 and 66 may have unequal lengths as well. The channel link elements 70 of the first and second sections are best shown in FIG. 7A and include an angled surface 71 and a flat surface 72, generally forming a D-shape. Also, at least one face of the channel link elements 70 include a bevel at an angle between 2° and 25°, so that when the link elements are adjoined, a gap 60 between the link elements is formed. Several lumens are disposed through the channel link element, including an activation cable lumen 73 that carries an activation cable, a deactivation cable lumen 74 that carries a deactivation cable, and neutral axis lumens 75 that carry static cables to hold adjacent link elements together. Referring again to FIG. 7, the split retractor is also shown to have a soft tapered tip 75 to prevent injury to tissue during the insertion of the device to the stomach. Further, the retractor is connected to a tissue treatment device 300 by an adapter transition link 76 of the first section 64. In the split channel retractor's straight insertion state, the cables housed by the channel link elements are slackened so the split retractor is free to move in all directions during insertion of the device, allowing the retraction section to freely navigate through tortuous lumens.

Referring now to FIGS. 8 and 8A, the split retractor 62 is activated into its curved shape by pulling an activation cable 79 in the proximal direction. The activation cable crosses from the first section of link elements 64 to the second section of link elements 66 at a pulley 77, and is crimped at an end cap 78 adjacent the distal most link element. The activation cable actuates the retractor by foreshortening angled gaps 60 between adjacent channel link elements 70 of the first and second sections 64 and 66, and by driving the pulley at the pivot 68. To return the retractor to its straight delivery position, a deactivation cable 81, which minors the path of the activation cable within the retractor section, is tensioned proximally to act in the opposing direction.

Another embodiment of the retractor section 20 is shown in FIGS. 9 and 10. FIG. 9 shows a flat retractor 80 in the delivery position, and the flat retractor includes a first end 82 and a second end 84 with a rounded tip. The flat retractor is formed from an elastomeric material, and is generally straight in the delivery position. Guide tubes 86 may be formed into the elastomer of the flat retractor to carry spring wires 88, such as nitinol wires, and possibly a supplemental wire which will be discussed more below. The spring wires can extend any length down the flat retractor to bias the retractor into the straight delivery or insertion position as shown in FIG. 9. An activation cable 89 is disposed along the scope tube of the device and is attached to the second end of the flat retractor. The activation cable may be pulled or tensioned in the proximal direction to curve the second end of the flat retractor into an arc as shown in FIG. 10 to retract or block tissue from a target area. To return the flat retractor into its insertion position, the activation cable is loosened, allowing the spring wires to bias the flat retractor into its straight position. It has also been contemplated that the flat retractor may not need spring wires to position itself in the straight position, because after loosening the activation cable, the flexibility in the elastomer of the flat retractor would allow the device to straighten as it is removed from the stomach and through the esophagus.

Figure 11:
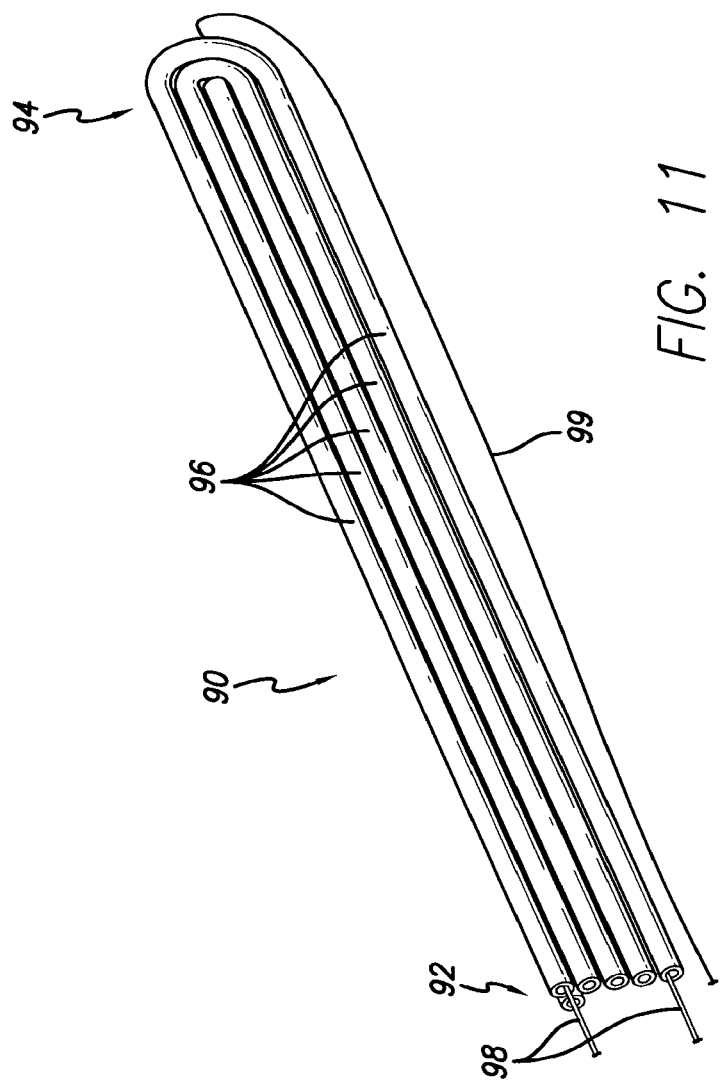
FIG. 11 depicts one embodiment of a tubular retractor in a straight delivery position.

FIG. 11 shows another embodiment of retractor section 20 that is a tubular retractor 90 having a first end 92 and a second end 94 that is rounded. The tubular retractor includes individual tubes 96 formed of a elastomeric material that can carry spring elements 98, such as nitinol wires, that bias the tubular retractor into a straight insertion position. An activation wire 99 is attached to the second end of the tubular retractor and extends to the proximal end 14 of the device 10. The activation wire may be pulled or tensioned at the proximal end of the device to curve the second end of the retractor into an arc in order to move unwanted tissue away from a target area or block unwanted tissue. To return the tubular retractor to its straight insertion position, the activation wire is loosened, allowing the spring elements to bias the retractor into its straight configuration.

Figure 12:
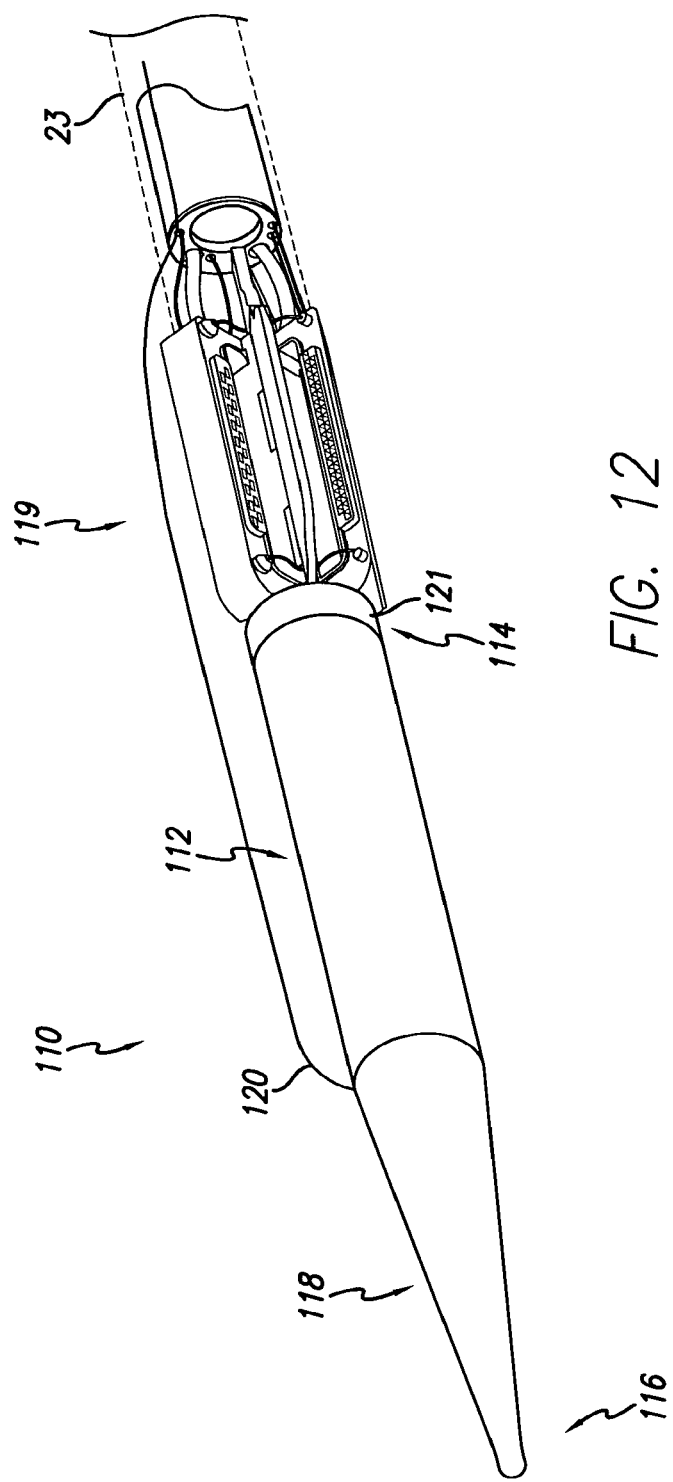
FIG. 12 depicts one embodiment of a bougie retractor attached to a distal end of a tissue treatment device in a straight delivery position.

In another embodiment, shown in FIG. 12, a bougie retractor 110 includes a cylindrical body 112 having a first end 114, a second end 116, and a taper 118. The cylindrical body is a tapered "bougie-like" body. It has also been contemplated that the bougie retractor includes a D-shaped body 112a as shown in FIG. 12A, so that one side of the body is flat. The bougie retractor is formed from a flexible elastomeric material, such as silicone rubber. In this figure, the first end is attached to a working element or therapeutic device 119, such as a tissue treatment device that is disclosed in U.S. patent application Ser. No. 10/797,303. The cylindrical body of the bougie retractor can be molded onto an adaptor 121 at its first end, so the retractor may more easily be connected to the therapeutic device. Although not shown, a post can be welded to the end of the therapeutic device that is advanced to a receiving hole in the adaptor, and a set screw can be used to lock the adaptor to the therapeutic device. In other embodiments, however, the device can be used without the working element 119 and the bougie retractor 110 may only be attached to the elongated body 12 of the device 10.

In one embodiment, an activation line 120 is attached to the cylindrical body 112 of the bougie retractor near the beginning of the taper 118 as shown in FIG. 12. In other embodiments, the activation line may be attached to the second end 116 of the cylindrical body, or at any other location along the cylindrical body. The activation line extends back along the outer surface of the cylindrical retractor and extends to the proximal end 14 of the device 10 to the handle 24. Therefore, when the activation line is tensioned or pulled in the proximal direction, the second end of the bougie retractor is curved back toward the first end to form an arc. This retraction position is shown in FIG. 12B. The activation line may also be attached to any location on the working element. In other embodiments of the bougie retractor, the cylindrical body may not include a taper. Still in other embodiments, the second end of the cylindrical body may be rounded to better slide along the lining of the stomach when the retractor is curved.

Figure 13:
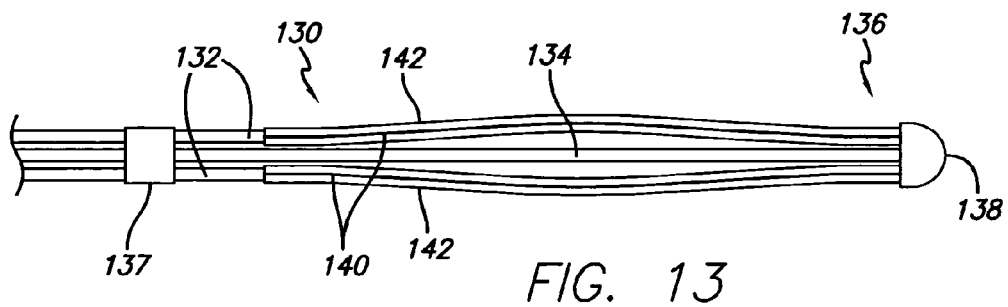
FIG. 13 depicts an embodiment of a bowed retractor in a delivery position.
Figure 14:
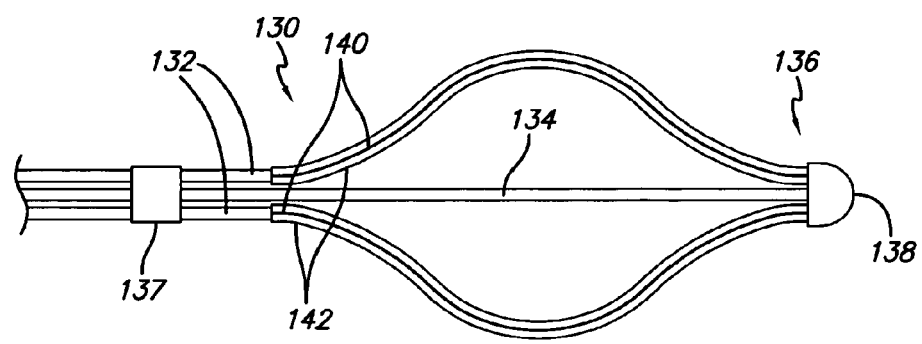
FIG. 14 depicts the bowed retractor of FIG. 13 with outer rods bowed outwardly.
Figure 15:
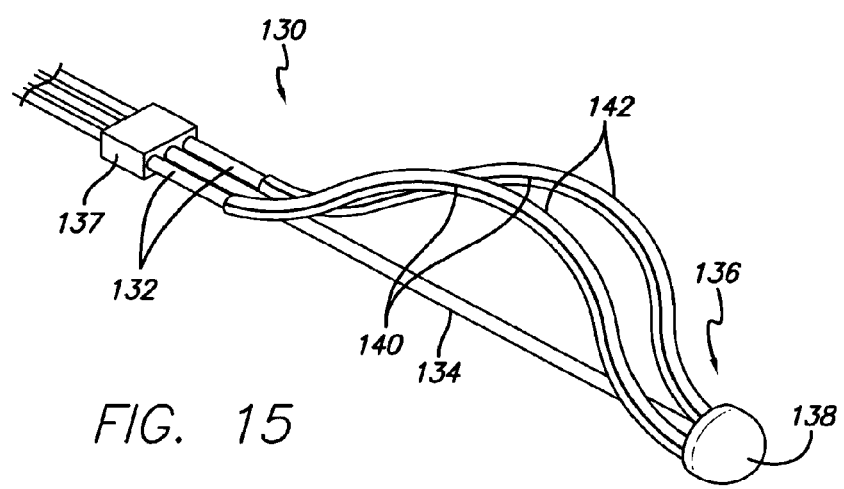
FIG. 15 depicts the retractor of FIGS. 13 and 14 with the outer rods rotated in an arched shaped.

Referring now to FIGS. 13-15, another embodiment of the retractor section 20 is shown. In this embodiment, a bowed retractor 130 includes two outer rods 132 and a central rod 134, all having a proximal end (not shown) (located outside of the patient when in use) and a distal end 136. A collar 137 positioned near the distal end holds the rods in relation to one another, and the central rod is allowed to slide proximally and distally through the collar. The distal end includes an atraumatic tip 138 that is connected to all three rods 132 and 134. In one embodiment, the outer arms each include a flexible wire 140 disposed at the distal end and the flexible wires are covered by a sleeve 142. The flexible wire can be of any flexible material such as nitinol or stainless steel. The sleeve may also include vacuum ports along its length and may be in fluid communication with a vacuum. FIG. 13 shows the bowed retractor in its insertion position.

Once positioned within the stomach, the bowed retractor 130 can be actuated by pulling the central rod 134 in the proximal direction. As the central rod moves proximally, the flexible wires 140 of the outer rods 132 bend or bow outwardly with the outer rods remaining stationary in the collar 137. This outwardly bowed shape is shown in FIG. 14. In one embodiment, a vacuum can be created within the outer rods allowing the vacuum ports located on the sleeve 142 to suction against tissue lining the stomach. The outer rods can then be rotated in one direction to each form an arc as shown in FIG. 15. In one embodiment, the bowed retractor is integrated with a therapeutic device (not shown). The therapeutic device can be positioned on the central rod so that when the outer rods are bent and rotated into an arc, the therapeutic device would be centered between the outer rods. The outer rods block unwanted tissue away from the therapeutic device, and also function to bring wanted or targeted tissue toward the jaws of the therapeutic device using the vacuum ports. The bowed retractor can be returned to its linear insertion position by rotating the outer rods in the opposite direction and then pushing the central rod distally to straighten the outer rods.

Another embodiment of the retractor section 20 is shown in FIGS. 16 and 17. A loop retractor 160 is shown in the delivery position in FIG. 16 and in the retraction position in FIG. 17. The loop retractor includes a single tube 162 that is bent over itself, having first and second ends that are located together at the proximal end 14 of the device 10, and a working portion 164 (looped end) that may include suction ports 166. During delivery, the single tube is positioned within a sleeve 167 that transports the single tube to the stomach. When the loop retractor is in the retraction position, a vacuum can be created within the single tube so that the working portion can suction onto the lining of the stomach wall in order to manipulate the tissue. The loop retractor is deployed into a retraction position from the delivery position by moving the first end and/or the second end distally so that the working portion of the device moves out of the sleeve and is able to expand into a loop within the stomach. Once deployed and a vacuum has been created, the single tube can be pushed, pulled, or rotated within the stomach to maneuver the tissue into a desired position. In use, the single tube is place against the lining of the stomach before the vacuum is created so that the suction ports attach to the stomach wall without desufflating the stomach cavity. A diameter formed by the working portion can range from about 1 inch to about 8 inch. Also, a diameter of the single tube should range between about ⅛ inch to about ¼ inch. In yet another embodiment that is shown in FIG. 18, the loop retractor may include two tubes that form two loops once in the retraction position. The retractor section shown in these figures may also retract tissue without using a vacuum.

In another embodiment, a linear retractor 170 is shown in FIGS. 19 and 20 integrated with a working element 172 such as the stapling device disclosed in U.S. patent application Ser. No. 10/797,303. The linear retractor includes at least one strut 174 and preferably two struts that, when deployed, retract tissue away or block unwanted tissue from entering the working element, allowing a target area to be treated by the working element. The working element may include a vacuum, and therefore when this vacuum is created, the linear retractor can block unwanted tissue from entering the working area of the working element. The struts include a distal end 176 with atraumatic tips 178, and a proximal end located at the proximal end 14 of the device 10. A working portion 180 of the struts is located adjacent the distal end and has a slightly curved shaped as shown in the figures. The linear retractor also includes a ramp 182 disposed proximal to the working element, and a pivot bracket 184 that is pivotally attached to the ramp. The struts are positioned between the ramp and the pivot bracket, and stops 186 are disposed on the working portion of the struts distally of the pivot bracket. FIG. 19 shows the linear retractor in the delivery position with the working portion of the struts positioned relatively close to the working element to form a low profile for advancement through the esophagus. To actuate the linear retractor into the retraction position as shown in FIG. 20, the proximal end of the struts are pulled in the proximal direction so that the stops of the struts engage and move the pivot bracket in the proximal direction. This allows the working portion of the struts to move away from the working element and into the retracted position. The position of the linear retractor is reversed by pushing the struts in the distal direction so that the stops move away from the pivot bracket, allowing the working portion to return to its delivery position close to the working element.

Figure 21:
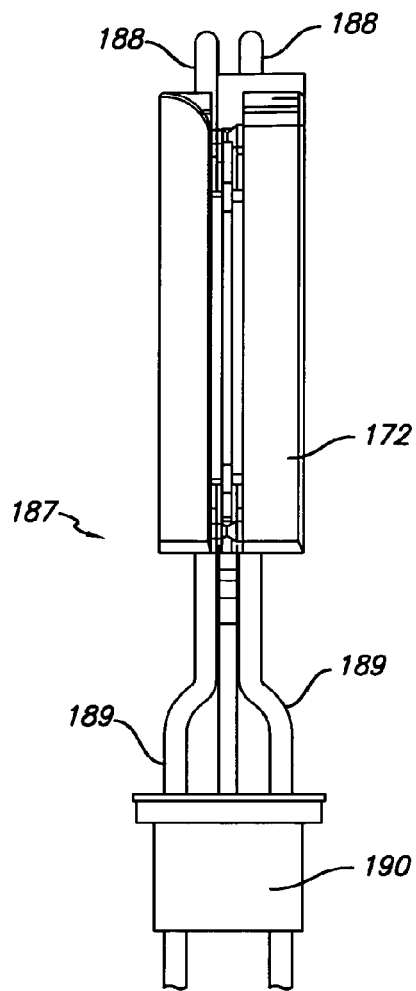
FIG. 21 depicts one embodiment of an arm retractor integrated with a tissue treatment device in a delivery position.
Figure 22:
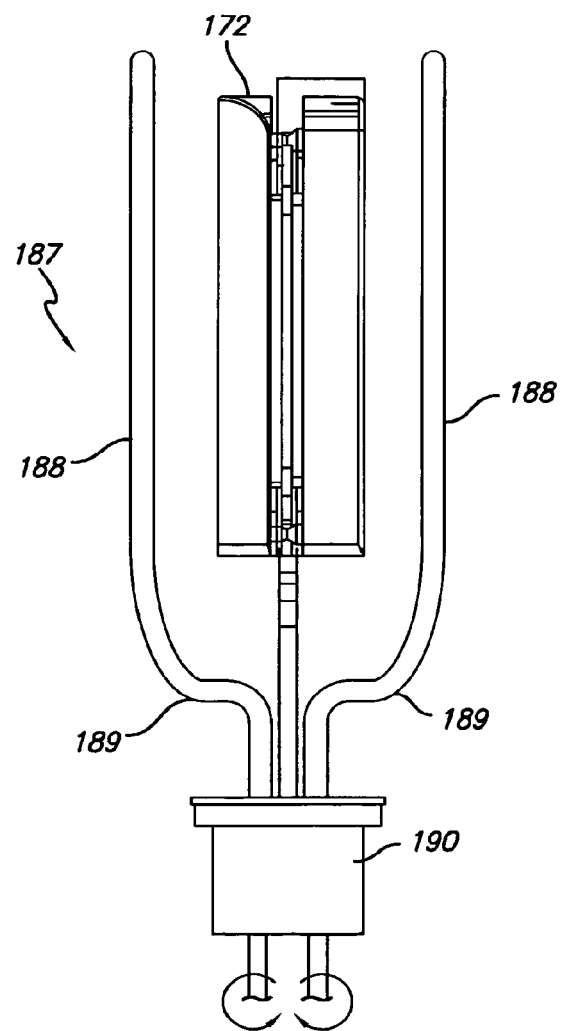
FIG. 22 depicts the arm retractor of FIG. 21 in a retraction position.

An arm retractor 187 is shown in FIGS. 21 and 22 integrated with a working element 172. The arm retractor includes two rods 188 having curved section 189 near the distal end. The rods are held relative to one another at the distal end by a collar 190. As shown in FIG. 21, the retractor is in its delivery position with the curved sections of the rods positioned underneath the working element. It is also possible that the rods can be positioned on top of the working element during delivery of this integrated device so long as the overall profile is low enough to advance the device through the esophagus. Once the device is positioned within the stomach, the rods can be rotated at their proximal ends to rotate the curved sections away from the working element as shown in FIG. 22. In this position, the rods move unwanted tissue away from the working element and also block unwanted tissue away from the working element. After the working element performs a therapy on the target tissue of the stomach, the proximal ends of the rods can be rotated in the opposite direction to return the curved sections to the working element so the entire integrated device can be removed from the stomach.

Figure 23:
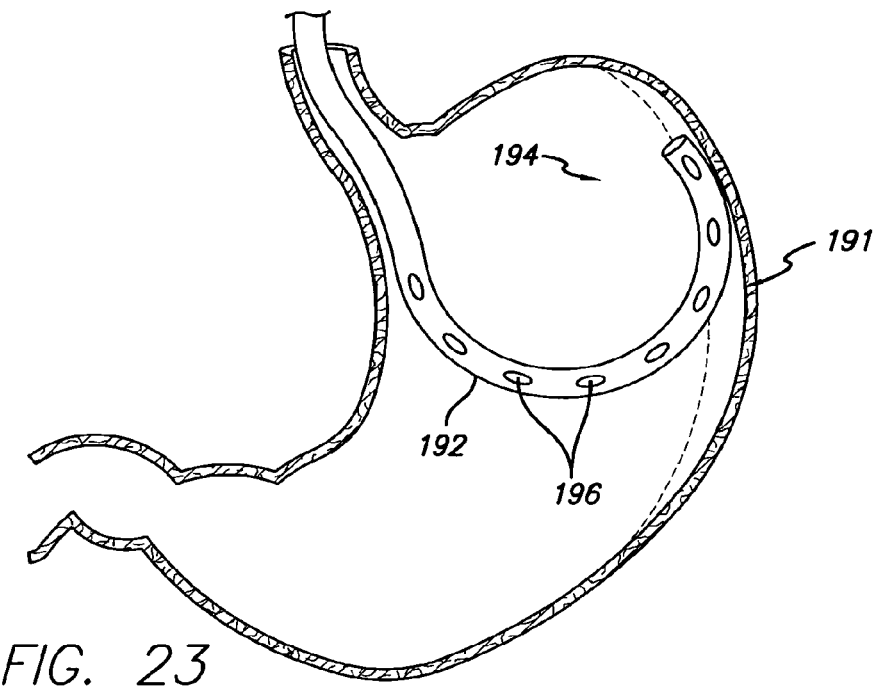
FIG. 23 depicts an embodiment of an articulating vacuum retractor in the retracted position within the stomach.

There are also several types of vacuum retractors that can be used as the retractor section 20. In one embodiment shown in FIG. 23, an articulating vacuum 191 includes a tubular body 192 with a proximal end (not shown) and a distal end 194 and also includes vacuum ports 196 near the distal end that can be used to help retract tissue within the stomach. The number of vacuum ports can vary, and may only include one port at the distal end. The articulating vacuum has the articulating capabilities of an endoscope, which is known in the art. In this embodiment, a vacuum can be created within the tubular body so that the vacuum ports at the distal end can suction onto the stomach tissue, and then the articulating vacuum can be maneuvered to reposition the stomach tissue, by pushing, pulling, folding, or twisting the stomach tissue. FIG. 23 shows the greater curve of the stomach being pushed away or stretched by the articulating vacuum. It has also been contemplated that to form another embodiment of the articulating vacuum retractor, an endoscope can be used that includes a sleeve placed over the endoscope, wherein the sleeve includes vacuum ports and the space in between the endoscope and the sleeve can be connected to a vacuum. An advantage of using an endoscope to retract tissue is that the target area being operated on can also be viewed by the operator. In another embodiment, an endoscope alone can be used to retract or block stomach tissue from the working element.

Figure 24:
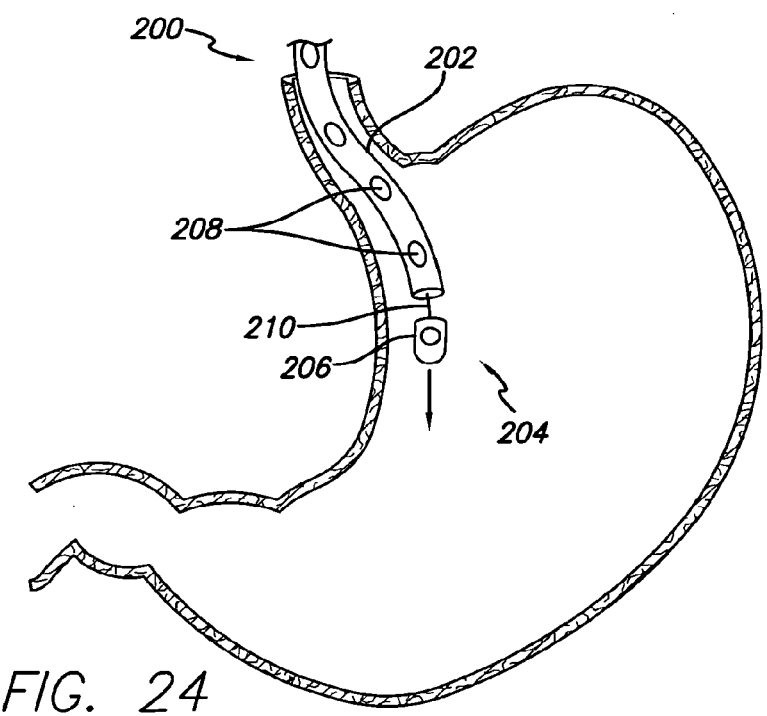
FIG. 24 depicts one embodiment of a vacuum-type retractor positioned along the lesser curve of the stomach.

FIG. 24 depicts another vacuum-type retractor. In this embodiment, a coaxial vacuum retractor 200 includes a tubular body 202 having a proximal end and a distal end 204, and a vacuum pod 206 located at the distal end that translates relative the tubular body. As shown, there are a plurality of vacuum ports 208 located at the distal end of the tubular body and at the vacuum pod, although only one vacuum port is needed at the vacuum pod. This retractor can articulate similar to an endoscope, and the vacuum pod can be moved relative to the tubular body by a rod 210 that is controlled at the proximal end 14 of the device. Once the distal end is within the stomach cavity, a vacuum can be applied to suction the stomach wall to the vacuum ports, and then the tubular body can be maneuvered to reposition the stomach tissue. This retractor also has the capability to smooth the lining of the stomach wall by removing wrinkles formed by the rugae of the stomach. The vacuum pod can be translated by pushing or pulling the rod, thereby allowing the coaxial vacuum retractor to tension or stretch desired sections of the stomach tissue. For example, the vacuum pod may be deployed to acquire tissue along the lesser curve of the stomach and then extended to apply axial tension to that region, thereby allowing a therapeutic device to be properly positioned, and also tensioning and smoothing out the target region.

Figure 25:
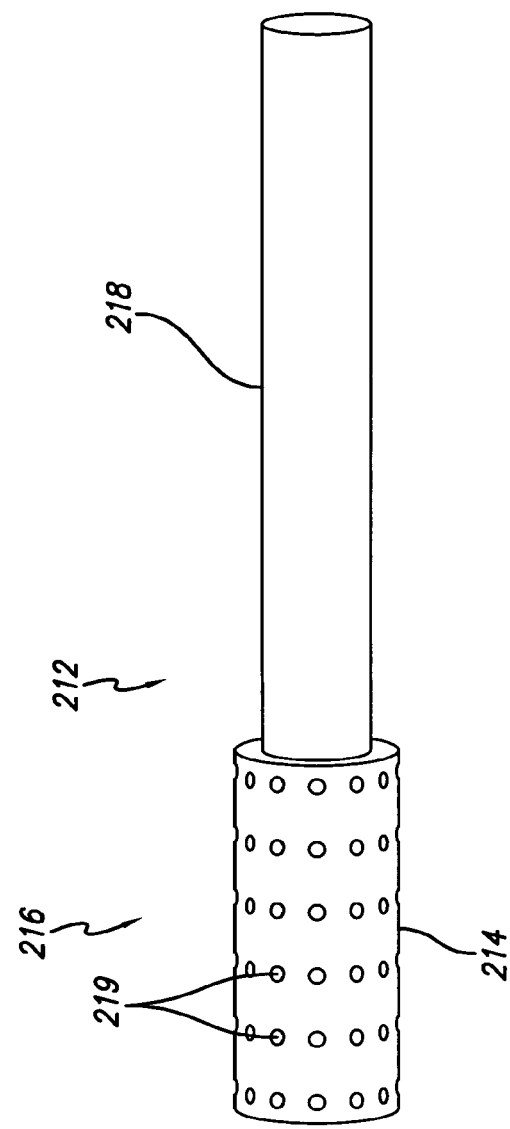
FIG. 25 depicts another embodiment of a vacuum-type retractor.

Referring now to FIG. 25, in yet another embodiment, a circular vacuum pod retractor 212 includes a vacuum pod 214 attached to the distal end 216 of an articulating tube 218. The vacuum pod includes a plurality of vacuum ports 219 disposed at least partially around the circumferential outer surface of the pod. The vacuum ports may only be disposed on one side of the pod, or they may be disposed around the entire outer surface of the pod. Further, only one vacuum port may be required on the vacuum pod. With all of the maneuvering capabilities of an articulating endoscope, the articulating tube is able to flex and curve in multiple directions. In operation, when the distal end of the articulating tube is positioned within the stomach, a vacuum in fluid connection with the vacuum ports can be created to suction stomach tissue into the vacuum ports. The circular vacuum pod retractor can then be pushed, pulled or articulated in any direction to maneuver the stomach tissue into a desired position.

Figure 26:
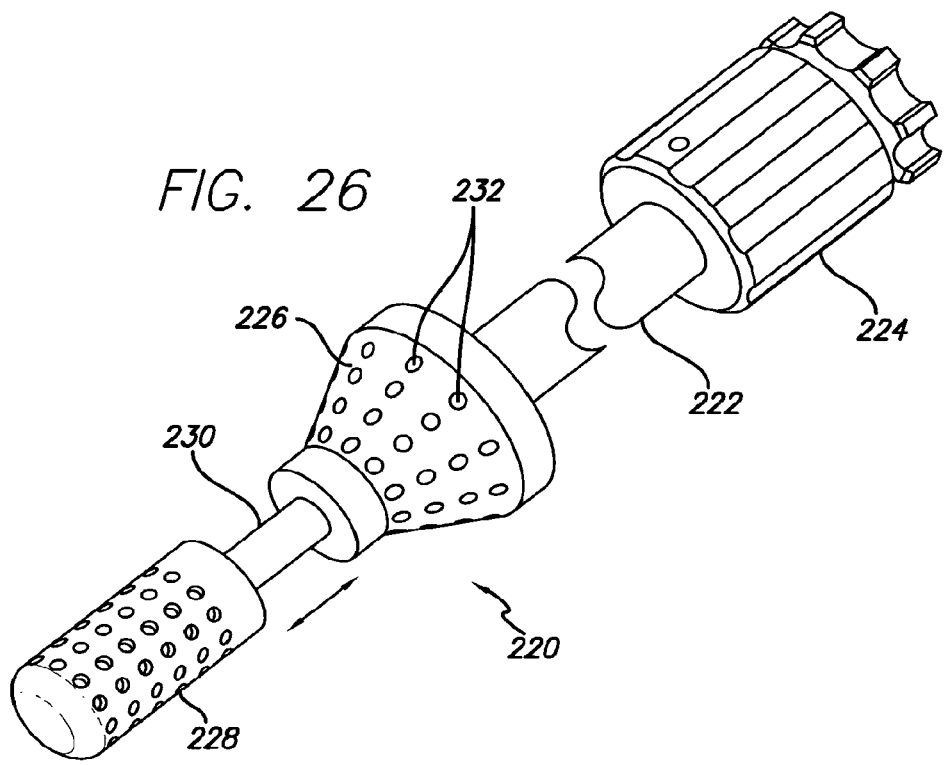
FIG. 26 depicts another embodiment of a vacuum-type retractor.
Figure 27:
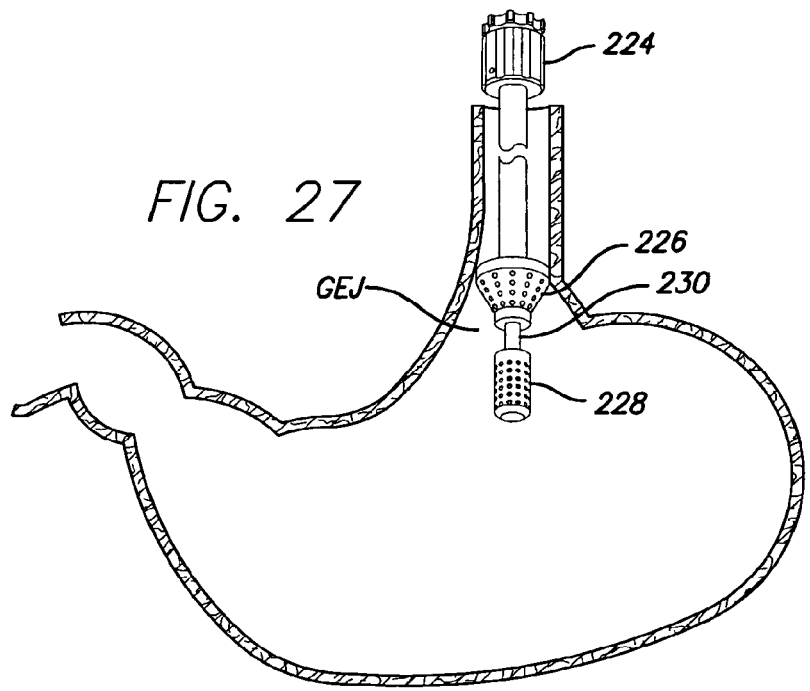
FIG. 27 depicts the vacuum-type retractor of FIG. 26 positioned near the gastroesophageal junction ("GEJ") of the stomach.

In another embodiment, a translating vacuum retractor 220 is shown in FIG. 26. The translating vacuum retractor includes a tubular body 222 along with a handle 224 at a proximal end, a cone-shaped pod 226 and a cylindrical pod 228 at a distal end. The cylindrical pod is disposed on a rod 230 that slides within the tubular body to translate the cylindrical pod relative the cone-shaped pod. In this embodiment, the cone-shaped pod includes several vacuum ports on its outer surface, and the cylindrical pod also includes vacuum ports on its outer surface. The outer shapes of the pods 226 and 228 can be altered without changing the scope of the invention, and only one vacuum port is required on each of the pods. Further, in another embodiment, the pods 224 and 226 may be reversed along the tubular body, so that the cone-shaped pod is at the distal end and translates on the rod relative to the cylindrical pod. The translating vacuum retractor can be used to push, pull or stretch the stomach tissue. In one embodiment for its use, FIG. 27 shows the translating vacuum retractor in position within a stomach, such that the cone-shaped pod is positioned near the gastroesophageal junction ("GEJ") and the cylindrical pod is positioned below the GEJ. A vacuum can be created so the stomach lining is suctioned to the vacuum pods, and the cylindrical pod can then be translated away from the cone-shaped pod to stretch the cardia of the stomach. This will better enable a therapeutic device to perform a therapy in the vicinity of the GEJ of the stomach.

In another embodiment, a tissue tensioning retractor 240 is shown in FIGS. 28 and 29, positioned along a therapeutic device 241, such as the device disclosed in U.S. patent application Ser. No. 10/797,303. The tissue tensioning retractor includes a platform 242 with a sliding surface 244 and a lip 246 at a distal end. Attached to the platform is a first pod 248 that is fixed, and a second pod 250 that translates relative to the first pod along the sliding surface of the platform. Each pod 248 and 250 includes one or a plurality of vacuum ports 252, and each is connected to its own vacuum line 254. The pods in this embodiment are rectangular in shape, however, other shapes such as circular, square, triangular or polygonal can be used as well. Further, in another embodiment, the first pod could also be movable along the sliding surface of the platform. In use, the tissue tensioning retractor is positioned within the stomach, such that the sliding surface is against the lesser curve of stomach, the first pod may be positioned above the lower esophageal sphincter ("LES"), and the second pod may be positioned below the LES. Once in position, a vacuum is applied to the first pod for grasping adjacent tissue above the LES, and a vacuum is then applied to the second pod which grasps adjacent tissue below the LES. The second pod can then be translated axially, thereby stretching the region of the stomach tissue and removing any wrinkles along the lining of the stomach. The therapeutic device can then provide therapy to a smooth target section of the stomach. In certain embodiments, the total length of translation along the sliding surface can be up to 4 inches. Preferably, the total length of translation between the first and second pods is about 1 to 3 inches. In addition, positioning the first pod can also act to stabilize the therapeutic device against the target region (lesser curve) to assist in creating a fastening line that is close to the targeted region (lesser curve) instead of flaring or angling away from the region.

A wire retractor 260 can also be used to push unwanted tissue from a target area. The wire retractor is shown in FIGS. 30 and 31 attached to a tissue treatment device or working element 262 having an optional septum 264. A first end 266 of the wire retractor is attached to the septum of the working element and the remaining wire is looped around the working element and through the scope tube 22, where a second end (not shown) is positioned at the proximal end 14 of the device. The first end may be attached anywhere along the working element including the hinge. In use, when the retractor and working element are passed into the stomach, the second end of the wire retractor is pushed distally as the first end is anchored to the working element, allowing excess wire 268 to form a loop 270 or other space occupying geometry within the stomach cavity. In this retraction position as shown in FIG. 31, the wire retractor pushes or blocks unwanted tissue away from the working element. In some embodiments, the wire retractor is a nitinol wire, although any material, including stainless steel, can be used to form the wire. The wire retractor may also be used without being integrated with a working element or the septum element. It has also been contemplated that the wire may have a circular cross-section or a rectangular cross-section, such as a flat ribbon. In addition, a plurality of wires may be used to create a structure around the working element.

Figure 32:
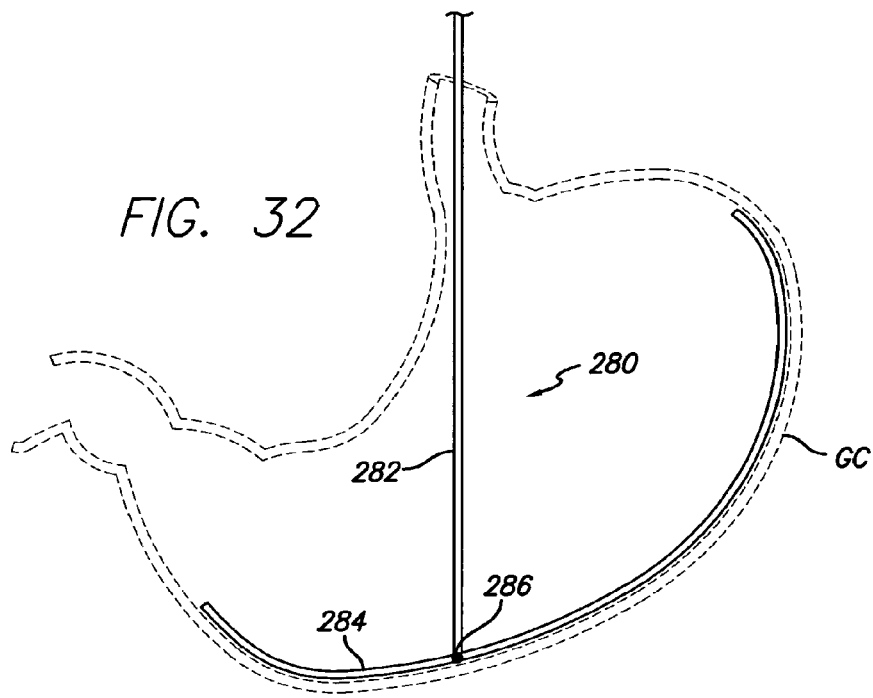
FIG. 32 depicts another embodiment of a wire retractor positioned along the greater curve of the stomach.

Other forms of wires can be used to retract tissue within a cavity. In one embodiment, as shown in FIG. 32, a T-shaped wire retractor 280 can be inserted and deployed within the stomach into a T-shape or anchor shape to present a target area of tissue for therapy. The T-shaped wire retractor includes an insertion rod 282 that is attached to a flexible rod 284 at a pivot 286 at the distal end of the insertion rod. During insertion, the flexible rod is pivoted to follow the position of the insertion rod, so that the retractor resembles a single straight rod. Once in the stomach, the flexible rod will pivot as its end comes into contact with the stomach wall, forming a T-shape with the insertion rod. The flexible rod could be deployed with cables or wires that could be retrievable or could remain within the stomach and along the esophagus to be used as a guide wire for insertion of a working element. In another embodiment, the flexible rod could deploy when its distal end comes into contact with the greater curve GC of the stomach, forcing the flexible rod to pivot on the insertion rod. As shown in FIG. 32, the T-shaped wire retractor is deployed within the stomach, and the flexible rod has pivoted away from the rod to form a T-shape or anchor shape that defines the greater curve of the stomach. Once deployed, the insertion rod may be pushed, pulled, or twisted to stretch the stomach tissue or move the stomach cavity in a more desirable position. To return the T-shaped wire retractor to its insertion configuration, a pull wire may be used to rotate the flexible rod on the pivot until the flexible rod is in-line with the insertion rod.

Figure 33:
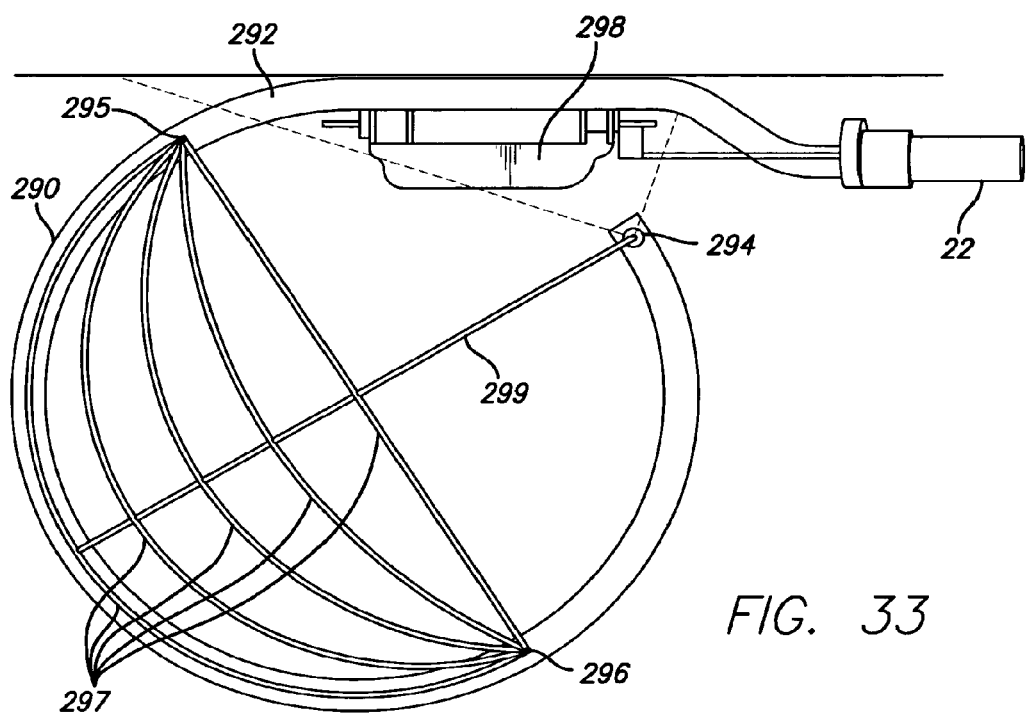
FIG. 33 depicts one embodiment of an endoscope retractor having retraction hoops that form a sphere configuration when retracted.

As previously discussed, an endoscope can be used to retract tissue, and another embodiment of an endoscope used as a retractor is shown in FIG. 33. This retractor is an endoscope 290 having a tubular body 292 with a distal end 294, and also includes retraction hoop or hoops 297 attached to the tubular body. The retraction hoops each have a first end 295 and a second end 296 that are fixed anywhere around the tubular body of the endoscope. In the retraction position shown in FIG. 33, the endoscope is advanced into a retroflex position and the retraction hoops are actuated so that each forms a hemi-spherical configuration, thereby retracting unwanted tissue away from a target area near the therapeutic device 298 shown in the figure. An actuating cable 299 is attached to the distal end of the endoscope and to each retraction hoop, so that when the endoscope actuates into the retroflex position, the actuating cable pulls the retraction hoops into a hemi-spherical configuration. Preferably, this retractor includes six retraction hoops, although there may be anywhere from two to twelve retraction hoops positioned on one side of the endoscope or on opposite sides of the endoscope. The retraction hoops may be formed of a resilient polymer, NiTi, stainless or other resilient or formable biocompatible material. These retractors may be independent of the scope or other wire structures, i.e. be adapted to be separately deployed.

Integrated Retractors

All of the retractor embodiments described above can be integrated with other devices, such as endoscopes, therapeutic devices or working elements, vacuums, suction cups, graspers, and even other secondary retractors. The working element shown in the figures is the tissue treatment device disclosed in U.S. patent application Ser. No. 10/797,303, however, any other gastroplasty device can also be integrated with the retraction devices.

Referring now to FIG. 34, the device 10 is modified by attaching or integrating a tissue treatment device 300 to the distal end of the scope tube 22 with struts 302 that may be flexible both to assist in passage of the scope, and also to assist positioning the tissue treatment device in the desired location relative to the targeted tissue. The retractor section 20 is attached to the distal end of the tissue treatment device by a transition section 304, which may be inverted U-shape channel link elements or other flexible or resilient construction to assist the retraction function. In this embodiment, the transition section is designed such that an endoscope 306 may be advanced through the scope tube, under the tissue treatment device, and through a port 308 created by the transition section to be positioned within the channel formed by the link elements 42 of the channel retractor. In this position, which is shown in FIG. 34, the endoscope is able to view the tissue treatment device during the surgical procedure. A secondary retractor 310 may also be integrated with the retractor section. This embodiment includes a supplemental wire retractor 312 or antrum retractor that can be retained within a groove 314 formed along the outer surface of the link elements. A distal end of the supplemental wire retractor is attached to the distal end of the channel retractor, and a proximal end of the supplemental wire retractor is located at the proximal end of the device. In use, the supplemental wire retractor can be pushed in a distal direction to leave the groove and expand into a retraction position in order to retract additional stomach tissue. Once the procedure has been completed, the supplemental wire retractor can be pulled proximally, returning it to the groove of the channel retractor, and the channel retractor can then be returned to its straight delivery position as described above. The endoscope can then be removed from the body of the patient, followed by removing the integrated device 10.

FIG. 35 shows another embodiment of the integrated device including the tissue treatment device 300 attached to the distal end of the scope tube 22 by a breach portion shown as struts 302 that may be able to move the tissue treatment device relative to the scope tube. It is contemplated that such a breach portion may also be formed by a molded part, casing or other housing to ensure a smooth transition of the scope or other working tool, while also preserving the atraumatic surfaces and overall flexibility of the device. In this embodiment, the channel retractor 40 is attached to the distal end of the tissue treatment device by a pin 316 that extends distally from the tissue treatment device. The channel retractor includes a connecting ring 318 that locks onto the pin. A bore 320 is disposed through the connecting ring so that the endoscope 306 can be advanced into the channel of the channel retractor. In this embodiment the bore extends through the center of the connecting ring. Similarly, any type of retractor, such as the bougie retractor, may be used instead.

An endoscope 306 also can be advanced into the channel of the channel retractor 40 when a bore 320 is disposed through the connecting ring as shown in FIG. 36. In this embodiment, the endoscope is advanced from the proximal end of the tissue treatment device and is then maneuvered through the bore into the channel. It is also within the scope of the invention to insert an endoscope or other working device alongside the retractor element in the event that the retractor does not have a channel or other cooperating feature.

Referring now to FIGS. 37 and 38, the flat retractor 80 is attached to the distal end of a tissue treatment device 300. The flat retractor can be attached to the tissue treatment device by using a set screw or a pin that latches the retractor to the tissue treatment device. This integrated device may also be used with an endoscope, a supplemental retraction wire 312, or any other secondary device. FIG. 38 shows a back view of the integrated flat retractor, and a bore 324 disposed through the proximal end of the flat retractor. This bore can allow an endoscope to be positioned on the front side of the flat retractor to view the tissue treatment device and the working area surrounding the tissue treatment device. It is also contemplated that the endoscope can be advanced through the scope tube 22 of the device and then be articulated to view the tissue treatment device from the side of the flat retractor. Also shown in FIG. 38 is the supplemental retraction wire positioned within a groove 326 along the backside of the flat retractor. As described above, the supplemental retraction wire can be deployed by simply pushing the wire in the distal direction, and the supplemental retraction wire can then be clamped or held outside the patient's body at the proximal end to hold the supplemental retraction wire in the retracted position.

Next, an integrated version of the bougie retractor 110 is shown in FIG. 39. As shown, the bougie retractor is attached to the distal end of the tissue treatment device 300. The bougie retractor operates in the manner described above, with the septum line or activation line shown as a dotted line. Similar to the integrated channel retractor, in this embodiment the tissue treatment device is attached to the distal end of the scope tube 22 by breach or bridge shown as flexible struts 302 that allow the tissue treatment device to be moved relative to the scope tube in order to provide space for an endoscope 306 to be advanced along the backside of the tissue treatment device. A sleeve 301 or other guide may be attached to the backside of the tissue treatment device to cradle or contain the endoscope or retractor device that may be inserted alongside the device. This feature may also prevent the scope from torqueing or "wowing" in a variety of directions that may impact the resulting geometry of the gastroplasty or pouch. The sleeve may be made of any flexible material and may be any length along the tissue treatment device. FIG. 40A shows a cross-sectional view taken along line 40A-40A of FIG. 40, showing the endoscope positioned within the sleeve 301. The endoscope can be used to view the tissue treatment device and the adjacent working area of the stomach by being retroflexed on the side of the bougie retractor as shown in FIG. 39. Although not shown in this figure, a supplemental wire retractor also can be integrated within a groove disposed along the bougie retractor.

Another embodiment of the integrated bougie retractor 110 is shown in FIG. 40, and at least a portion of the cylindrical body 112 is carved away to form an indentation 330 so that the endoscope 306 can more easily view the tissue treatment device. The indentation formed in the surface of the bougie retractor can be of varying depths and lengths without effecting the integrity of the bougie retractor.

Referring to FIG. 41, an endoscope 306 is shown in conjunction with a tissue treatment device 300. The endoscope is resting adjacent or alongside the tissue treatment device and is flexed to retract unwanted tissue away from the tissue treatment device and to view the tissue treatment device. FIG. 41A shows another embodiment of the tissue treatment device, in which the optional septum 332 of the tissue treatment device is hinged to the tissue treatment device at the distal end, so that after tissue within the stomach has been acquired, the septum can be moved away from the working area to allow the tissue treatment device to form a staple line along the stomach lining. The septum can be moved away from the working area by using a pushing rod or a pull wire. Further, the struts 302 connecting the tissue treatment device to the scope tube may be rotatable to axially misalign the tissue treatment device relative to the scope tube. Other embodiments of the septum and tissue acquisition device can be seen in U.S. Pat. No. 6,558,400, which issued May 6, 2003, and U.S. patent application Ser. No. 10/797,439, which was filed Mar. 9, 2004, which have already been incorporated by reference.

Another embodiment is shown in FIGS. 41B and 41C, where an optional septum 333 is integrated with a retractor, such as a wire retractor 260a. FIG. 41B shows the wire retractor having two resilient wires (e.g. nitinol wires) attached to the septum. The septum is connected to the tissue treatment device 300 by a pin (not shown) or other means. In this embodiment, the wires may be pushed distally to form a loop within the stomach cavity to push or block any unwanted tissue away from the tissue treatment device. During the tissue treatment procedure, the septum is removed to allow the tissue treatment device to acquire the tissue, by first releasing the pin connecting the septum to the tissue treatment device. Then, the resiliency of the wires flips the loose septum away from and out of the tissue treatment device as shown in FIG. 41C. It has also been contemplated that the wire retractor 260a can only be used to remove the septum from the tissue treatment device.

Figure 42:
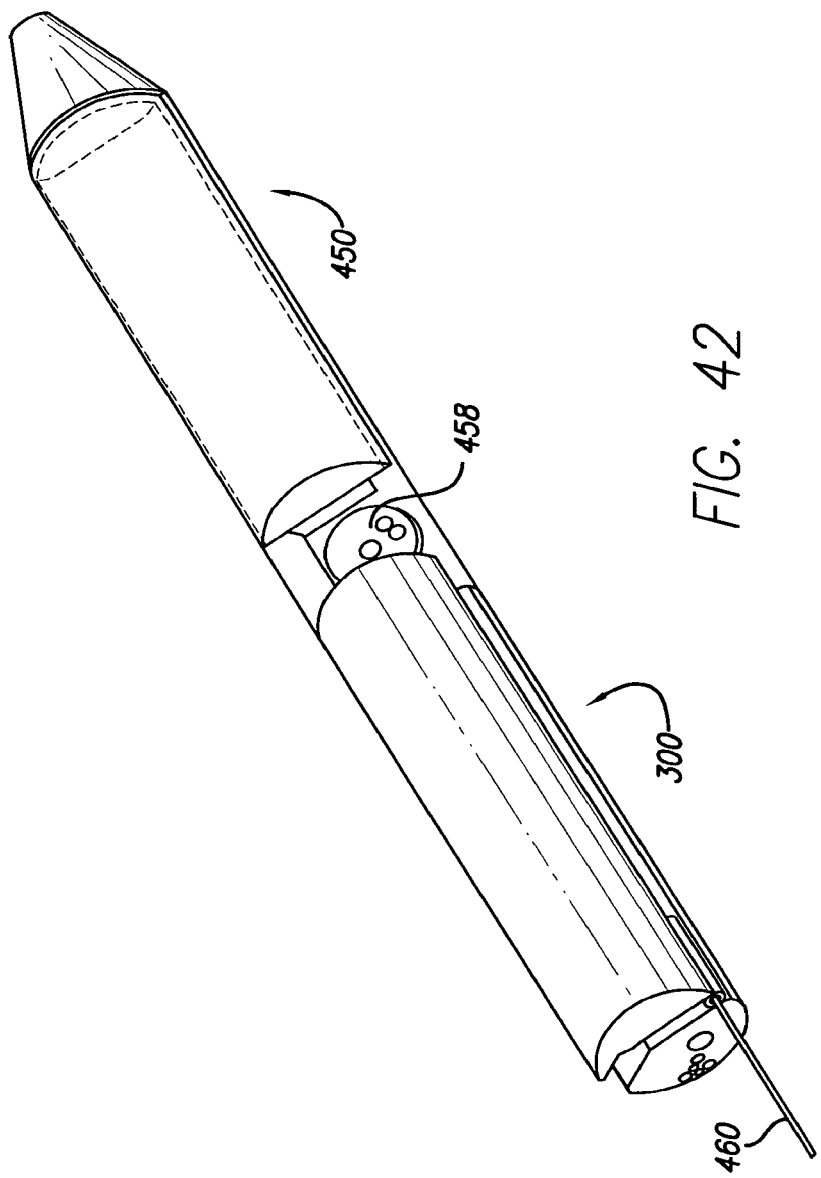
FIGS. 42 through 42B depict an embodiment of a tissue treatment device having a fan septum.
Figure 42B:
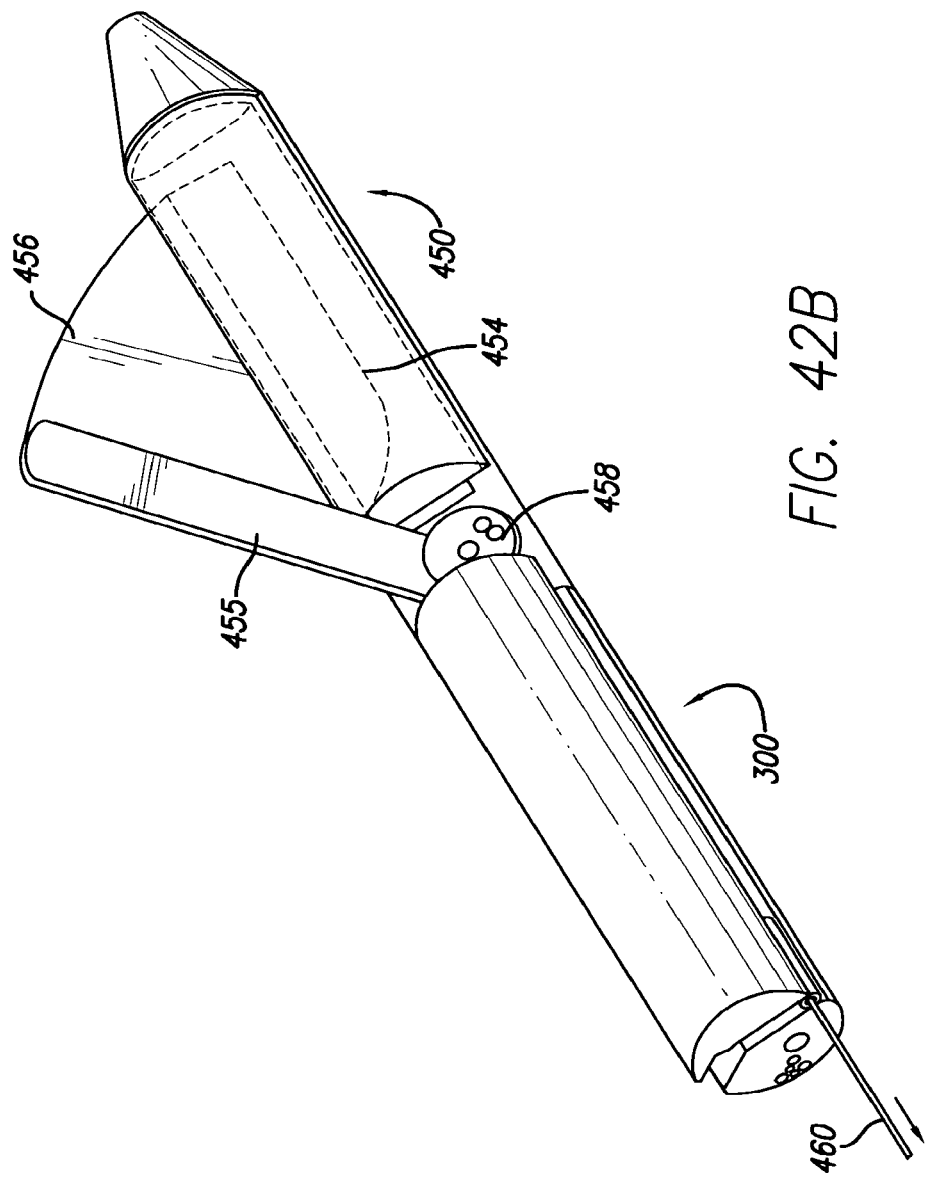

Another embodiment is shown in FIGS. 42 through 42B, with a tissue treatment device 300 integrated with a modified bougie retractor 450. In this embodiment, the tissue treatment device includes a fan septum 452 having a first blade 454, a second blade 455, and a sheet 456, such as a plastic film. The sheet is attached to an edge of the first blade and an edge of the second blade. There is a removable pin that joins the second blade to the tissue treatment device. Distal ends of the first and second blades are attached to the distal end of the tissue treatment device at a pulley 458. There is also a pull cable 460 that attaches to the pulley, and when pulled raises the septum into a retraction position. The modified bougie retractor includes a slot 462 that is disposed and sized for receiving the fan septum.

FIG. 42 shows the device in the delivery position, with the fan septum 452 positioned within the tissue treatment device. Once positioned in the stomach, the jaws of the tissue treatment device are opened, and the pull cable 460 is pulled proximally to turn the pulley and raise the first blade 454 of the fan septum as shown in FIG. 42A. In this position, the sheet 456 is stretched between the first and second blades. The first blade can be raised to an angle that is determined by the size of the sheet. Tissue can be acquired by the tissue treatment device while the first blade is in a raised position to assist in gathering tissue. After tissue has been gathered, the releasable pin can be removed to release the proximal end of the second blade, and the pull cable 460 can then be pulled to swing both the first and second blades, along with the sheet, into the slot 462 of the modified bougie retractor 450 as shown in FIG. 42B. The jaws of the tissue treatment device are then closed so the integrated device can be removed.

Figure 42C:
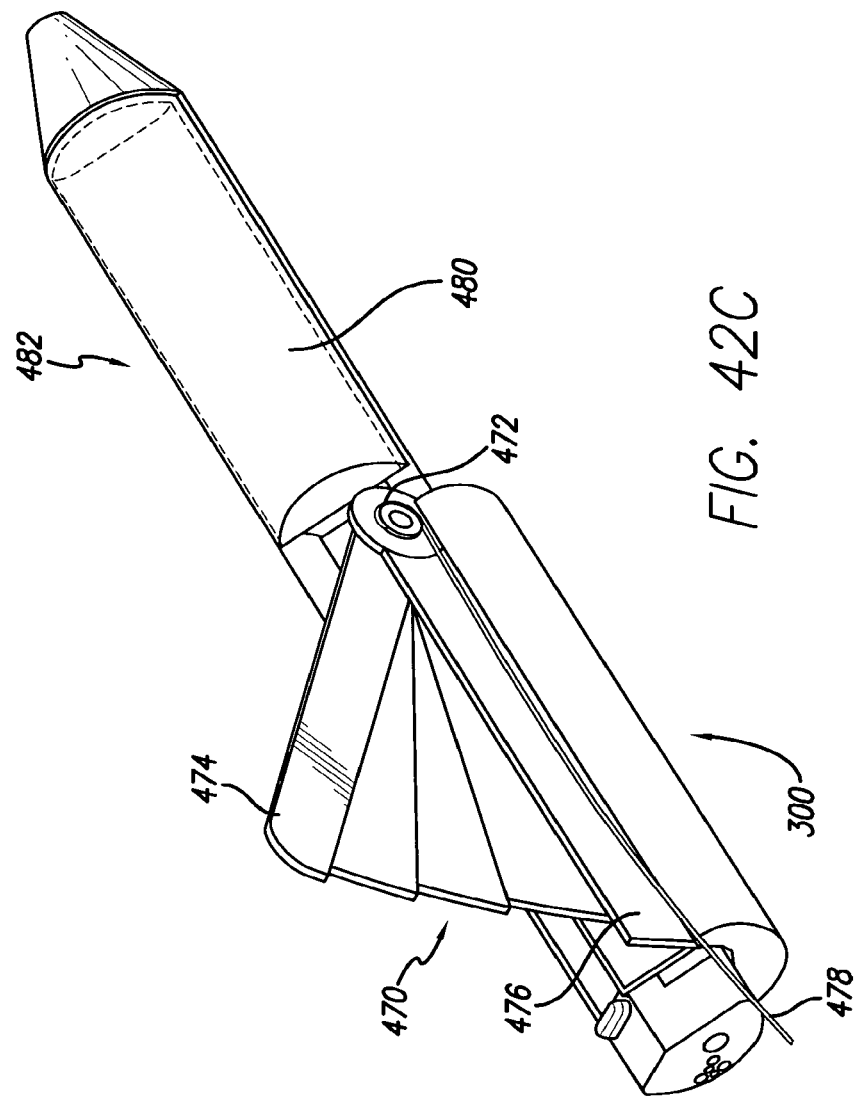
FIG. 42C depicts another embodiment of a tissue treatment device having a multi-blade fan septum.

FIG. 42C shows another embodiment of a tissue treatment device 300 having a multi-blade fan septum 470. The multi-blade fan septum includes a plurality of blades that are slidably joined together to fan out when in a raised position. The distal end of the blades are attached to a pulley 472 disposed in the tissue treatment device. There is a proximal fan blade 474, which is raised first, and a distal fan blade 476 that is attached to the tissue treatment device by a releasable pin. Any number of blades may be between the proximal and distal blades, and the preferred embodiment includes a total of five blades including the proximal and distal blades. Once the device is positioned within the stomach, the jaws of the tissue treatment device are opened, and a pull cable 478 that is attached to the pulley 472 is pulled proximally to raise the blades of the multi-blade fan septum. The proximal blade is raised only to a position allowed by the other blades which fan out. After tissue is acquired, the releasable pin can be removed to free the distal blade, and the pull cable can be pulled proximally to swing the multi-blade fan septum into a slot 480 of a modified bougie retractor 482. The slot is sized to house the multi-blade fan septum. When the blades are secured within the modified bougie retractor, the jaws of the tissue treatment device can be closed, and the integrated device is then removed from the patient.

The device 10 along with the different embodiments of the retraction section 20 can be integrated with secondary retractors, such as a supplemental wire retractor, endoscopes to view the working area, and tissue treatment device to perform a therapy to the target area. Other devices can also be incorporated with retraction device. For example, as shown in FIG. 43, a flat band spreader 340 may be used to move the stomach tissue into a position that is more useful for advancing the retractor device 10 or tissue treatment device into the stomach cavity without pushing into the stomach wall. The flat band spreader includes a flat band 342 that has a normal bent configuration resembling a loop 344 with a pointed end 346 as shown in FIG. 43. It is possible that the bent configuration of the flat band can resemble any other geometry as well. An elongated tube 348 is used to house the flat band for delivery into the stomach. The cross-section of the flat band is rectangular in shape as shown in FIG. 43A. A handle 350 is attached to the proximal end of the flat band and is used for deploying and retracting the flat band. In use, the elongated tube, sized such that it fits within the lumen of the scope tube 22, is advanced through the retractor device and into the stomach, where the handle can be pushed in a distal direction to advance the flat band out from the elongated tube, allowing the flat band to transform into its normal bent configuration. It is also possible for the elongated tube to be pulled proximally allowing the flat band to resume its bent configuration. The loop of the flat band should reposition the stomach, allowing the retractor device to further advance into the stomach. The flat band spreader can also be used to retract the stomach tissue to help a tissue treatment device acquire desired tissue.

Figure 44:
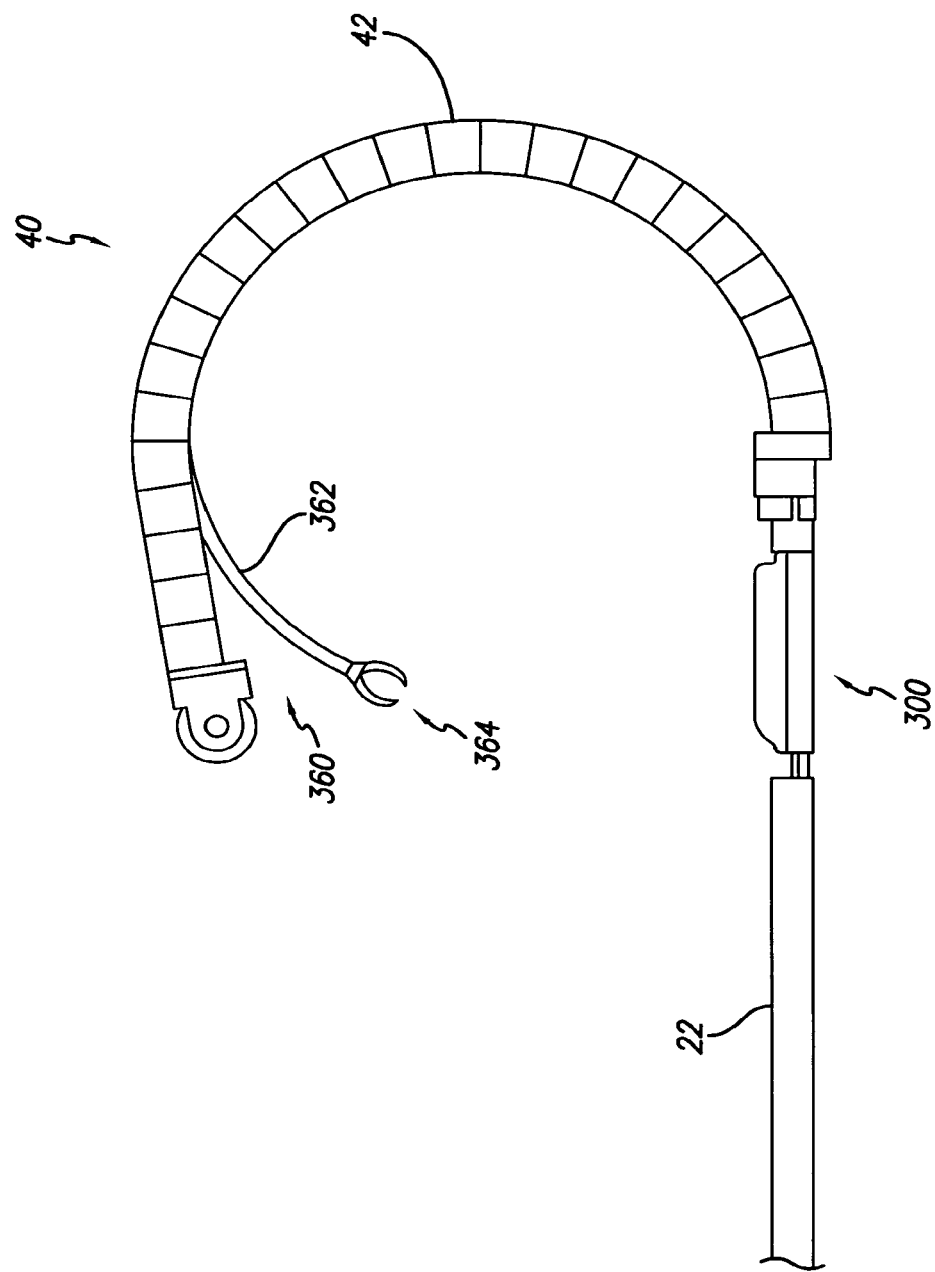
FIG. 44 depicts another embodiment of a retractor device integrated with a tissue treatment device, and this embodiment also incorporates a grasping forceps retractor.

Another type of secondary retractor that can be incorporated into any of the embodiments of the retractor devices is a grasping forceps retractor 360. Referring to FIG. 44, the channel retractor 40 is shown as an example of how the grasping forceps can be incorporated into the device. In this embodiment, the grasping forceps retractor includes an elongated tube 362 that houses a cable, and forceps 364 connected to the cable and located at the distal end of the elongated tube. In this embodiment, a pair of grasping forceps retractors extend through the scope tube and into separate forceps lumens 50 of the channel link elements 42, and each exits at an angle to the distal end of the retractor section. It is preferred that the grasping forceps retractors extend from the channel retractor so that they are aimed at the sides of the tissue treatment device 300. Once the channel retractor is in the retraction position within the stomach, the elongated tube of the grasping forceps can be moved in the distal direction to extend the forceps from the channel retractor so that the forceps come into contact with tissue located near the tissue treatment device. The cable extending through the elongated tube is used to actuate the forceps to grab onto tissue, and the elongated tube can then be pulled in the proximal direction to pull and drape surrounding tissue onto the tissue treatment device. Although this embodiment is described as being incorporated with the channel retractor, the grasping forceps retractor can be incorporated with any of the retraction devices previously described.

In another embodiment, a secondary retractor includes suction vacuum cups that extend from a retractor section and are used to grasp tissue in a similar manner described above with the grasping forceps retractor 360. The suction vacuum cups are disposed at the distal end of a vacuum tube and are maneuverable within the stomach to extend from a retractor section, such as the channel retractor, and grasp tissue that can then be pulled toward the tissue treatment device.

Using vacuum ports or suction cups along or within any of the embodiments of the retractor section has also been contemplated. The vacuum ports or suction cups allow any of the retractor sections to grasp onto the stomach tissue and move tissue from the target area to a tissue treatment device, after the retractor section has blocked or moved unwanted tissue away from the target area.

Additional Retraction Devices And Methods

Other retraction devices can be used in place of or in combination with the retractor device 10 described above to accomplish the same goal of moving or keeping unwanted tissue away from a target area or smoothing the stomach tissue. One method of retracting the stomach tissue is by use of insufflation alone. Using this technique, the stomach cavity is insufflated by blowing a gas therein to expand the stomach. Insufflating the stomach expands the stomach cavity which smoothes out any folds or wrinkles that may be found within the stomach. After insufflation, the smooth stomach wall can then be acquired by a tissue treatment device to perform a therapy without acquiring folds or wrinkles, which may be undesirable. Also, insufflating the stomach cavity allows a retractor device to more easily maneuver into the stomach and actuate into the retraction position. In some embodiments the stomach is desufflated before acquiring tissue with the tissue treatment device, and the retractor device would then block unwanted folds of tissue from reaching the tissue treatment device after desufflation.

Figure 45:
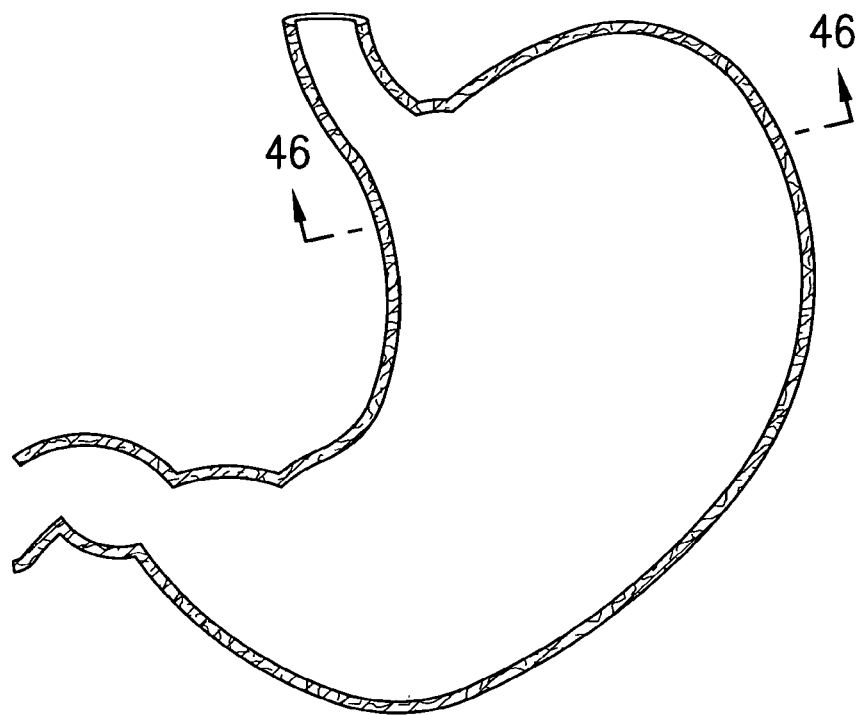
FIG. 45 depicts a cross-sectional view of a stomach.
Figure 46:
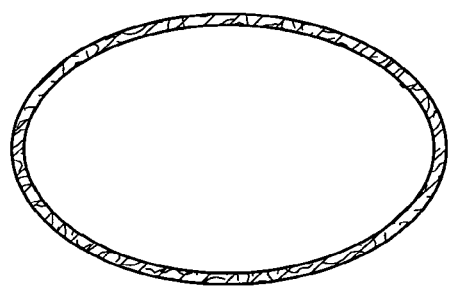
FIG. 46 depicts a cross-sectional view of the stomach taken along line 46-46 of FIG. 45.
Figure 47:
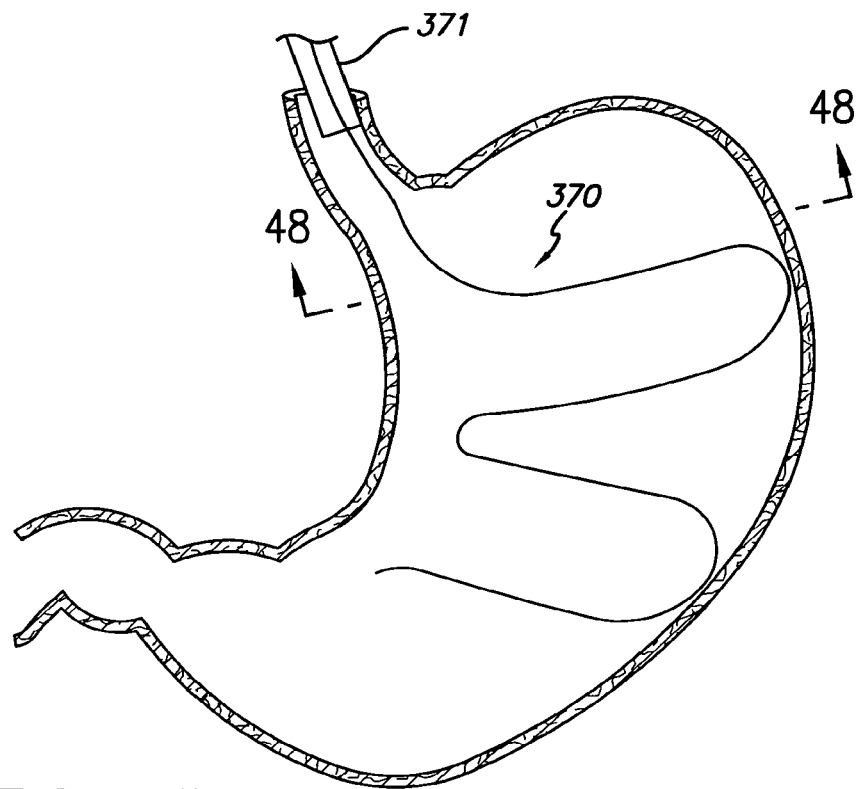
FIG. 47 depicts an embodiment of a form wire deployed within the stomach.
Figure 48:
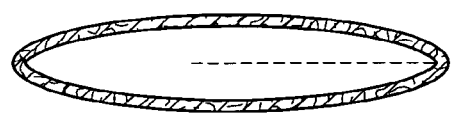
FIG. 48 depicts a cross-sectional view taken along line 48-48 of FIG. 47.

There are several other embodiments for expanding the stomach to retract or smooth the stomach wall. One embodiment is to insert a formed wire 370 into the stomach that takes on a predetermined shape once it is inserted into the stomach cavity to hold tissue away from a target area. The formed wire can be nitinol that has a predetermined shape. To advance the formed wire into the stomach, a tube 371 can be used to house the formed wire, which is then advanced to the stomach. Once the tube reaches the stomach, the formed wire can be advanced out of the tube to resume its predetermined shape. For comparison reasons, FIG. 45 shows an illustration of an empty stomach, and FIG. 46 shows the cross-section of the stomach taken along line 46-46 of FIG. 45. Referring now to FIG. 47, a form wire is shown deployed within the stomach, and FIG. 48 shows the cross-section of the stomach taken along line 48-48 of FIG. 47. When the form wire is deployed within the remnant volume, the cross-section of the stomach is forced into a lenticular, or pancake shape, bringing the anterior and posterior sides of the stomach closer together, which allows a tissue treatment device to better acquire and perform a therapy to a target area. By stretching the stomach, any wrinkles or folds found within the stomach may also be smoothed out, allowing the tissue treatment device to acquire tissue from a target area without also acquiring wrinkles or folds from the stomach wall. To remove the form wire from the stomach cavity, the wire is simply pulled back into the tube and then removed from the body of the patient.

Figure 49:
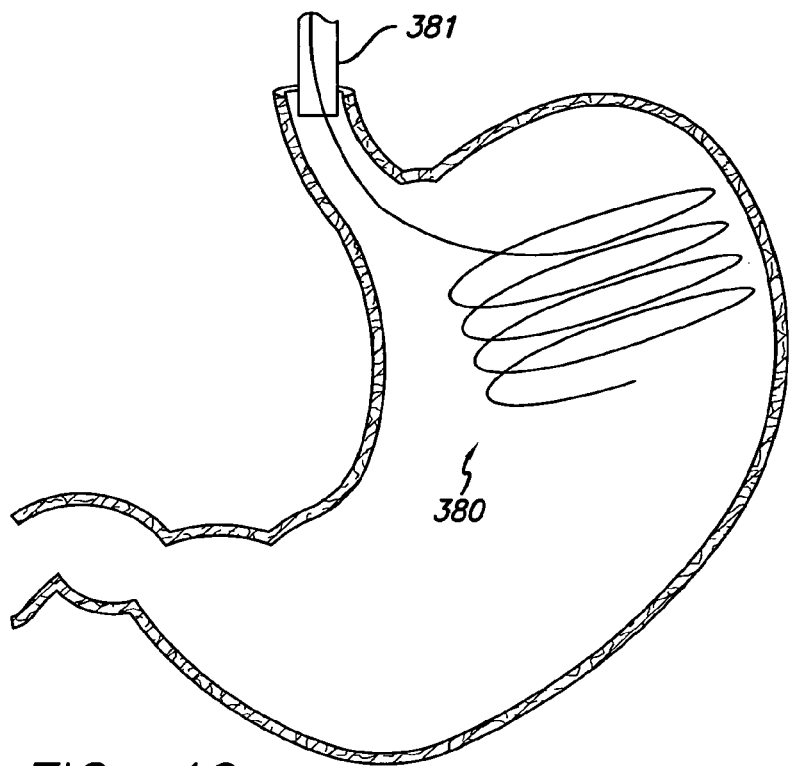
FIG. 49 depicts an embodiment of a coil wire deployed within the stomach.

Other embodiments, like the one shown in FIG. 49 include inserting a coil 380 into the stomach to block tissue away from a target area in order to allow a tissue treatment device to acquire preferential tissue. Similar to the above form wire embodiment, the coil is straightened and housed in a tube 381 for advancement into the stomach. Once at the stomach, the coil can be deployed from the tube so that the coil resumes its natural shape.

Figure 50:
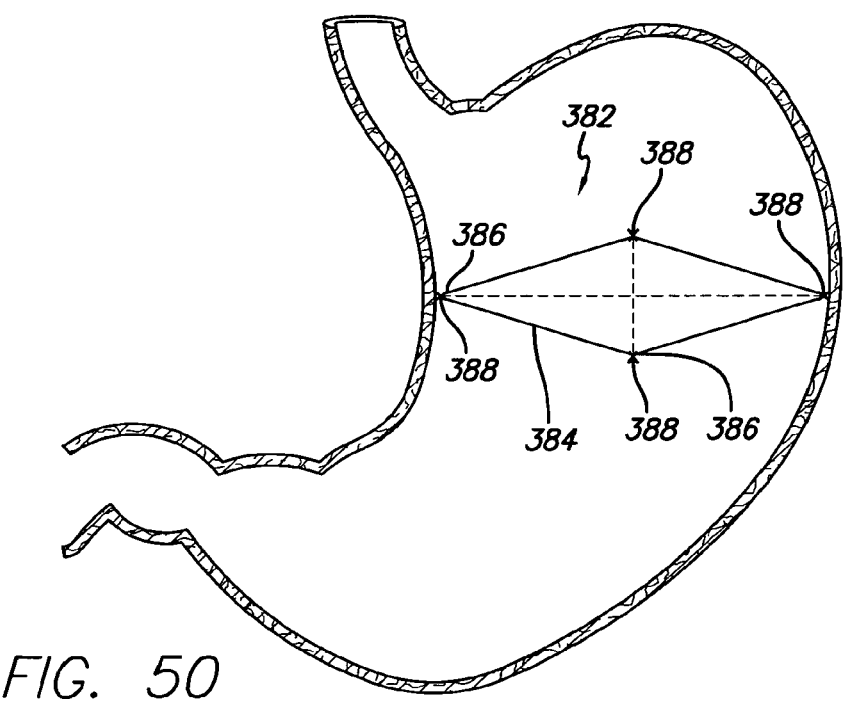
FIG. 50 depicts an embodiment of a kite retractor deployed within the stomach.

FIG. 50 shows an embodiment that includes a kite retractor 382 having a frame 384 that resembles the shape of a kite when it is in the retracted position. The frame includes four ends or points 386 that may include clips 388 to grasp onto the stomach wall. This design would block tissue and allow the tissue treatment device to acquire preferred tissue. During insertion into the stomach, the frame of the kite retractor is folded into a longitudinal body and advanced to the stomach via a tube or catheter. Once in the stomach the kite retractor is deployed using a push rod to expand the frame of the kite retractor. The same push rod or even pull cables may be used to attach the clips onto the wall of the stomach. In one embodiment, the kite retractor is expanded into the stomach after the stomach is first insufflated.

Figure 51:
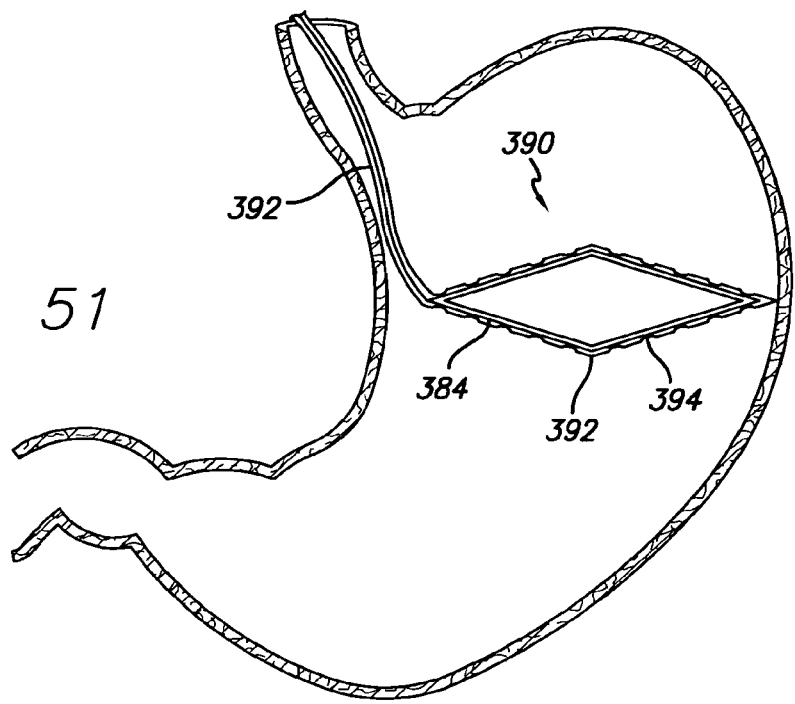
FIG. 51 depicts another embodiment of a kite retractor including a suctioning tube disposed within the stomach.

It has also been contemplated that the clips disposed on the kite retractor 382 could be replaced with suction cups or even vacuum ports. When using vacuum ports, the frame 384 of the kite retractor would include a vacuum tube having vacuum ports for suctioning onto the stomach wall. In the embodiment shown in FIG. 51, the kite retractor includes a vacuum tube 392 surrounding the frame of the kite retractor, with several vacuum ports 394 located around the vacuum tube. In this embodiment, once the kite retractor has been deployed within the stomach, a vacuum can be created within the vacuum tube, so that the vacuum ports suction onto the stomach wall. These devices can all be inserted into the stomach while it is insufflated. Then, before acquiring tissue for treatment by the tissue treatment device, the stomach can be desufflated and the retraction devices will then block unwanted tissue from the tissue treatment device.

Figure 52:
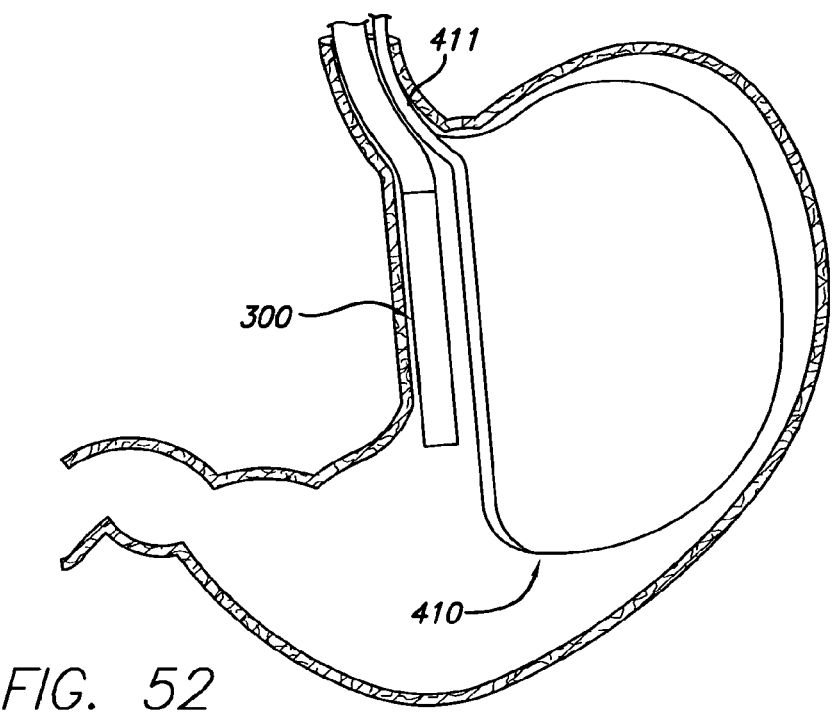
FIG. 52 depicts an embodiment of a balloon deployed within the stomach.

Yet another embodiment is the use of a balloon 410 to retract or block tissue to achieve preferential tissue acquisition for creating a target pouch. FIG. 52 shows a balloon catheter 411 with an expanded balloon that is inflated on the front side of a tissue treatment device 300. In this embodiment, the balloon catheter is inserted into the stomach separately from the tissue treatment device. In other embodiments, the balloon catheter may be attached to the backside of the retractor section. Once the tissue treatment device is placed within the stomach near a target area, the balloon can be inflated to hold tissue in place or to block unwanted tissue from the tissue treatment device. The inflated balloon expands the stomach and may even push the stomach wall along the greater curve of the stomach away from the tissue treatment device, thereby smoothing out any wrinkles or folds along the stomach wall. This allows the tissue treatment device to acquire tissue without acquiring wrinkles or folds.

Figure 53:
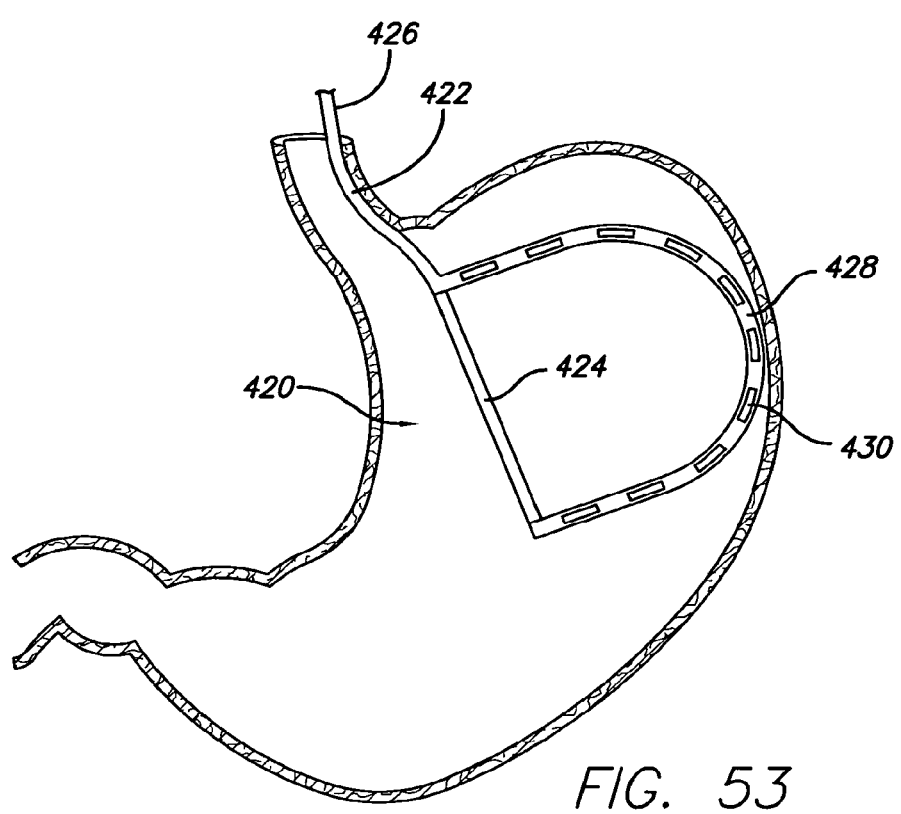
FIG. 53 depicts an embodiment of a bow retractor deployed within the stomach.

In another embodiment, a bow retractor 420 can also be used to retract tissue within the stomach. Referring to FIG. 53, the bow retractor includes a bowing tube 422 that is connected to an insertion rod 424. The bowing tube includes a proximal portion 426 that is disposed around the insertion tube, and a bowing portion 428 found at the distal end. The bowing portion does not surround the insertion rod and is only attached to the insertion rod at the distal end. It is noted that the bowing portion and proximal portion are in fluid communication with one another. The bowing portion forms a semicircle when deployed, and the bowing portion may include suction ports 430 so that a vacuum can be applied. To deploy the bowing portion, the rod is pulled proximally, shortening the distance between the distal end of the bowing portion and the proximal end of the bowing portion. In this position, the bowing portion is able to retract tissue and block any unwanted tissue from a tissue treatment device.

Placing these above-described devices into the remnant volume of the stomach blocks or retracts tissue within the stomach, and even thins or smoothes out any wrinkles or folds found in the tissue. By retracting the stomach tissue in such a way, a tissue treatment device is assisted in forming a pouch within the stomach as taught by the above incorporated references. The retraction helps achieve preferential tissue acquisition by the tissue treatment device. It should be understood that these devices can also be incorporated within or attached to the tissue treatment device, and can be used in combination with the retraction devices described earlier.

Figure 54:
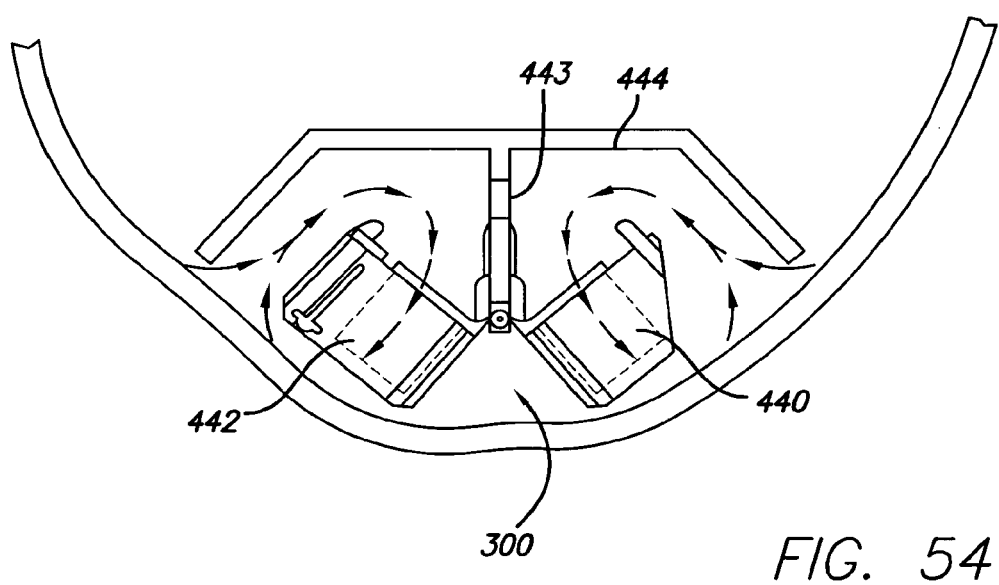
FIG. 54 depicts a distal end view of a tissue treatment device including a septum having a hood that extends over the opening of the tissue treatment device.

The gastroplasty device or tissue treatment device could also be altered to retract or block tissue from the opening of the tissue treatment device. As shown in FIGS. 11A through 11D of U.S. patent application Ser. No. 10/797,303, which already has been incorporated by reference, the septum of the gastroplasty device can include a septum member and a perpendicularly positioned transverse septum member, which may extend partially over the openings when the cartridge member and anvil member are in an open configuration. As shown in FIG. 54, the tissue treatment device 300 includes a cartridge member 440 and an anvil member 442, and a septum 443 that includes a transverse septum member or hood 444 that extends over the opening between the cartridge member and the anvil member. The hood attaches to the gastroplasty device in the same manner the septum does. When a vacuum is created within openings found in the cartridge and anvil members to suction tissue of the stomach wall, the hood acts to block unwanted tissue, such as folds or wrinkles, from entering the vacuum openings of the cartridge and anvil members. The shape and size of the hood may be varied to block more or less tissue from the gastroplasty device. For example, the hood may be formed more like a "T" by eliminating the curved end sections of hood 444.

Yet another embodiment of a retractor section integrated with a tissue treatment device is shown in FIGS. 55A through 55D. This embodiment includes an axial retractor 500 having an actuation sleeve 502 that houses two pre-shaped nitinol wire struts 504. Retractable anchors 506 are attached to the distal end of the nitinol wire struts and may include snares, graspers, or have suction capabilities to grab onto stomach tissue for manipulation. The nitinol struts are pre-shaped so that they bend outwards when removed from the actuation sleeve as shown in FIG. 55B. In use the actuation sleeve is positioned along the side of tissue treatment device 300 during delivery. FIG. 55A shows the integrated device being delivered to the stomach near the LES. Once at the LES, the pre-shaped nitinol struts are pushed distally out of the actuation sleeve and they bend outward until the anchors come into contact with the prolapsed tissue of the stomach. The anchors grasp onto the tissue and can be used to further push or retract the stomach tissue. The nitinol struts can also be pulled proximally within the actuation sleeve, so that the tissue is brought closer to the tissue treatment device as shown in FIG. 55C. After the tissue is brought toward the tissue treatment device, the actuation sleeve can be pushed distally to move the tissue acquired by the anchors distally, removing any wrinkles in the prolapsed tissue of the stomach. FIG. 55D shows the wrinkles of the stomach tissue removed and the tissue treatment device advanced into position to perform a therapy.

The retractor devices described above, either separate or integrated, can perform several functions. First, the retractor devices pull away, block or otherwise manage rogue tissue, mainly excess fundus tissues, from being involved in the tissue treatment device. Also, the retraction devices organize the targeted tissue by flattening or removing wrinkles and sub-folds from the desired lip folds. Then the targeted tissue can be suctioned into or brought to members of the tissue treatment device for therapy. Any flattening of rugae is beneficial during the surgical procedure. Further, the retraction devices support the placing of the tissue treatment device within the stomach in the desired sleeve forming location. The retractor device can help move the tissue treatment device closer to the lesser curve of the stomach, or the retractor device can be used to initially move the stomach to bring the lesser curve of the stomach to the tissue treatment device. Another advantage is that the retractor devices can retract or accommodate inter-abdominal pressure from weight of internal organs and abdominal wall. The retractor should be strong enough to lift and bear the weight of internal organs or it can orient the stomach in a direction that does not encounter such loads. Yet another advantage is that by having a flexible element distal to the tissue treatment device, such as the bougie retractor described above, it helps the tissue treatment device pass tortuosity more easily.

Methods

Figure 56:
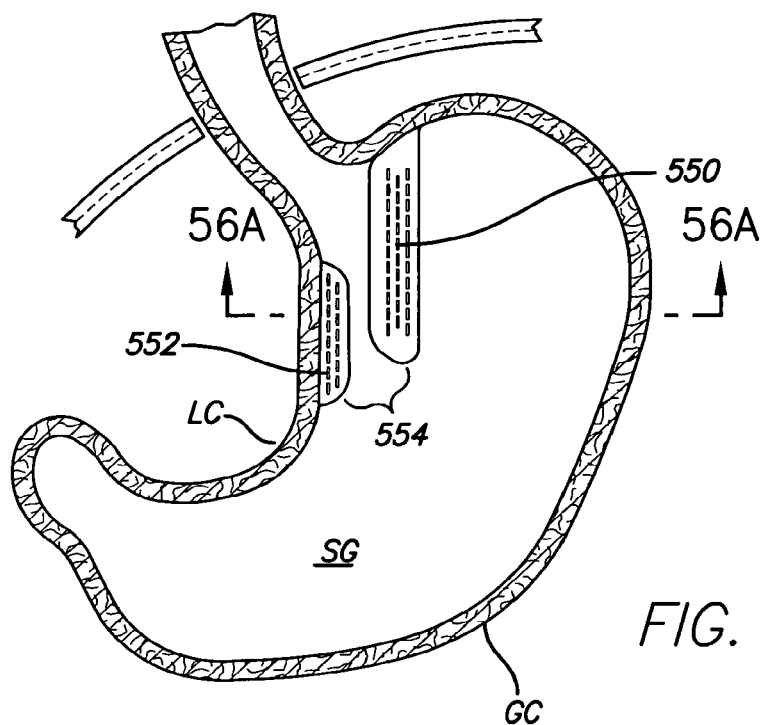
FIG. 56 depicts a cross-sectional view of a stomach cavity that has been reconfigured with a tissue treatment device.
Figure 56A:
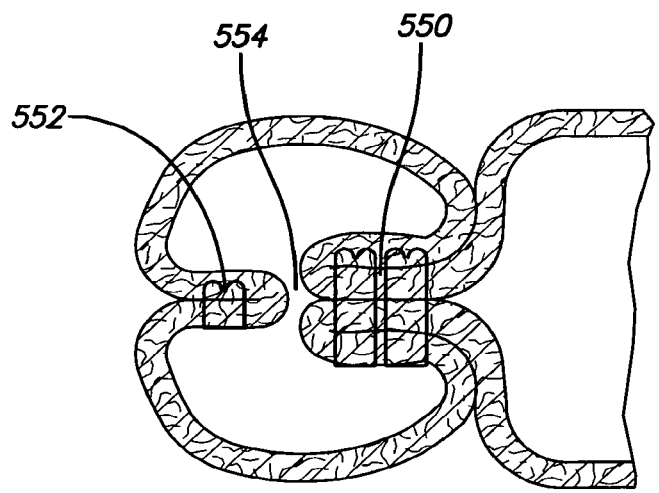
FIG. 56A depicts a partial cross-section taken along line 56A-56A in FIG. 56.

The retraction devices described above can be used in combination with a tissue treatment device to provide therapy to the stomach of a patient. In general terms, a retraction device along with a tissue treatment device can be inserted transorally to the stomach. Some embodiments include an integrated device where the retraction device and the tissue treatment device are integrated together into a single unit to simplify the surgical procedure. In embodiments where an endoscope is being used to view the stomach cavity, the endoscope can be initially loaded within the scope tube of the device, or may be placed separately alongside the device, or initially loaded within the tube and then directed outside the device body to maximize visualization/retroflexing of the scope. Although not required, it is preferred that the stomach be insufflated before advancing the device into the stomach. Once in the stomach cavity, the endoscope can be retroflexed to about 180°-270° so that its distal end is directed back towards the scope tube to view the tissue treatment device. When the devices or the integrated device is correctly positioned within the stomach, the retraction device can be deployed or retracted to move, push or pull portions of the stomach tissue away from a target area near the tissue treatment device to allow a surgical region of the stomach to be approximated for treatment. The retractor section is actuated using the handle at the proximal end of the device. With unwanted wrinkles or folds retracted away from the tissue treatment device by the retraction device and the area being viewed by the endoscope to assist the physician with the surgery, the stomach tissue from the target area can be acquired for treatment. In embodiments where the stomach is insufflated at the beginning of the procedure, the stomach is desufflated, usually by the suction force of the tissue treatment device, as the tissue treatment device acquires the appropriate tissue. After the tissue is acquired, the jaws of the tissue treatment device clamp together to form multiple tissue folds (a dual fold), and then staple the dual fold of tissue to form a sleeve staple line 550 that is generally about 45 mm in length. The retraction section is then returned to a straight position so the integrated device can be removed from the stomach cavity. Once the integrated device is removed, a single fold treatment device may then be inserted into the stomach to form a single fold plication 552 along the lesser curve of the stomach. The single fold plication is about 25 mm in length and is positioned along the lesser curve of the stomach so that a distal stoma 554 is formed between the single fold plication and the dual fold staple line, that is about 10 mm in diameter. After stapling tissue along the lesser curve the single fold treatment device is removed and the stomach is left reconfigured as shown in FIG. 56. The distal stoma can more easily be seen in FIG. 56A, which is a cross-section taken along line 56A-56A of FIG. 56. Depending on the desired tissue geometry and accuracy of the placement of the single fold plication, the method can be repeated allowing additional single fold plications to be placed within newly created tissue geometry.

Figure 57:
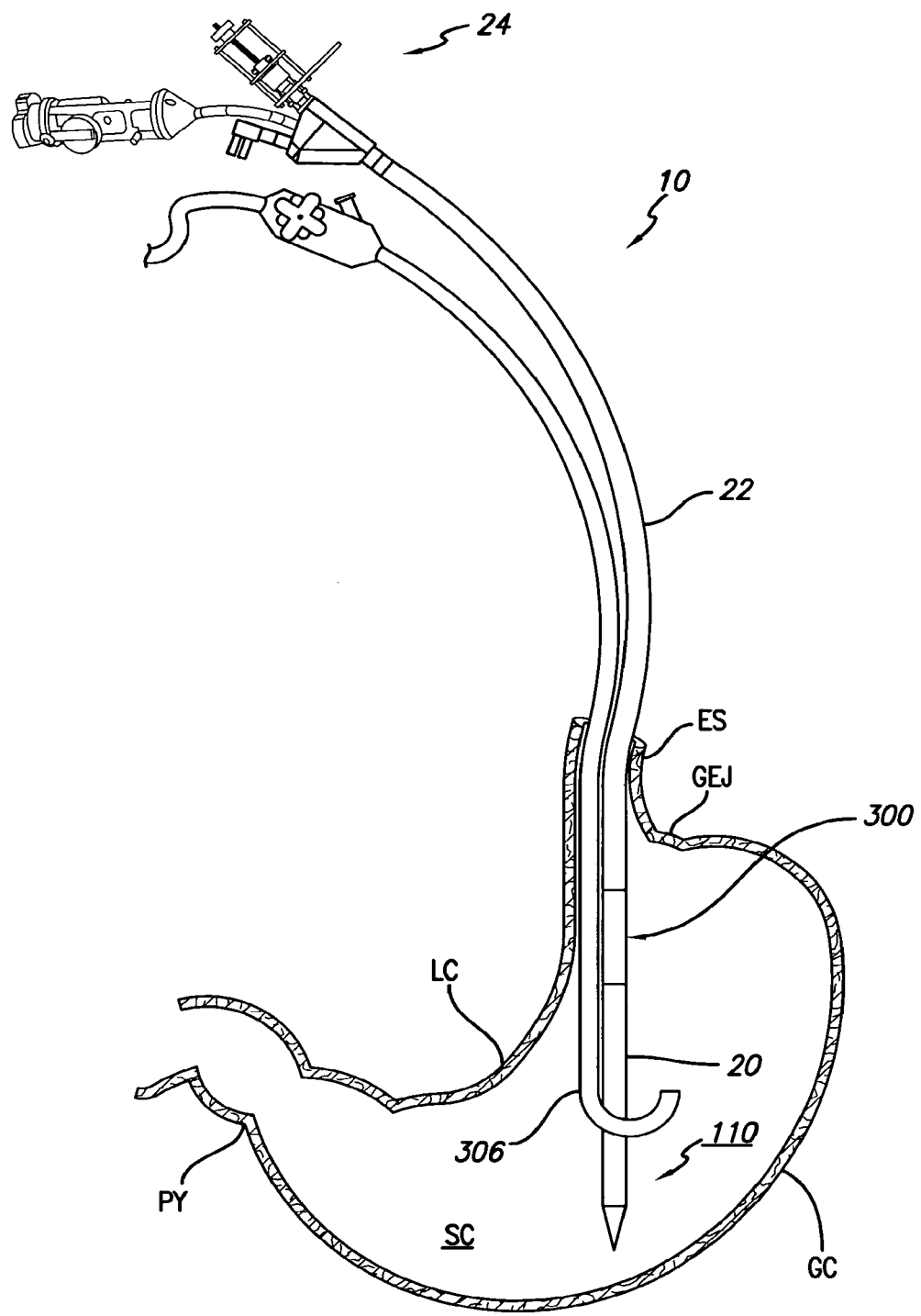
FIG. 57 depicts one embodiment of a retractor device integrated with a tissue treatment device positioned within the stomach and an endoscope retroflexed in the stomach.

A representative illustration of how the retractor device 10 and the tissue treatment device 300 are used together to treat a target area will now be described. Referring to FIG. 57, the integrated retractor device 10, including a retractor section 20 and a tissue treatment device 300, is shown being advanced transorally through the esophagus ("ES") of a patient and positioned within the stomach cavity ("SC"). As described in the incorporated references, the tissue treatment device may be articulated outside of the patient via a handle so that the distal portion (portion farthest from the handle) of the tissue treatment device may be positioned such that the spine of the device is placed against a portion of lesser curvature ("LC") and opposite greater curvature ("GC"). In this way, the tissue treatment device extends between the gastroesophageal junction ("GEJ") towards pylorus ("PY"). The retractor section may also be articulated outside of the patient via the handle 24 either before or after the tissue treatment device is correctly positioned.

Figure 58:
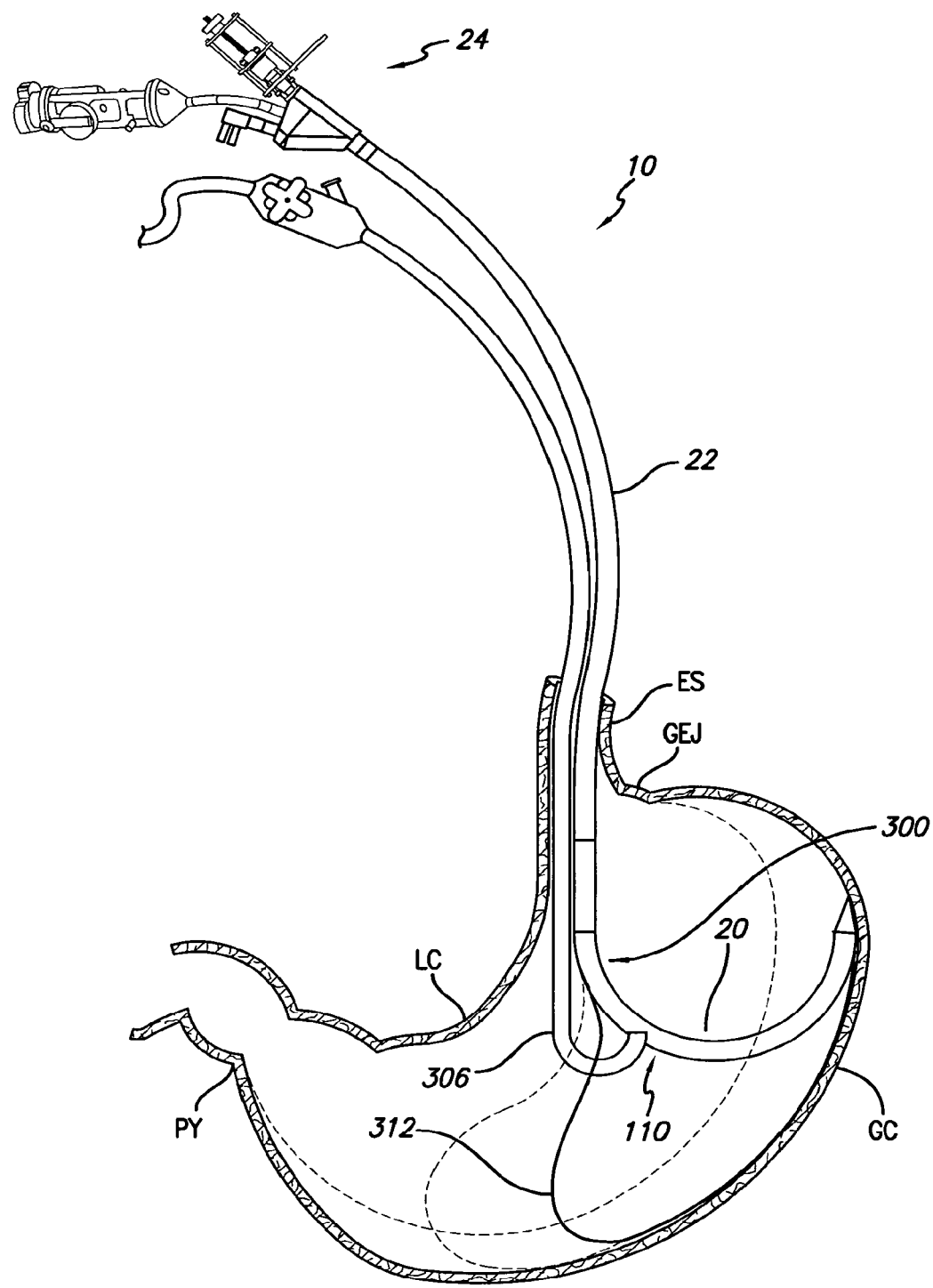
FIG. 58 depicts the integrated retractor device of FIG. 57 in the retracted position and a secondary wire retractor is also deployed.
Figure 59:
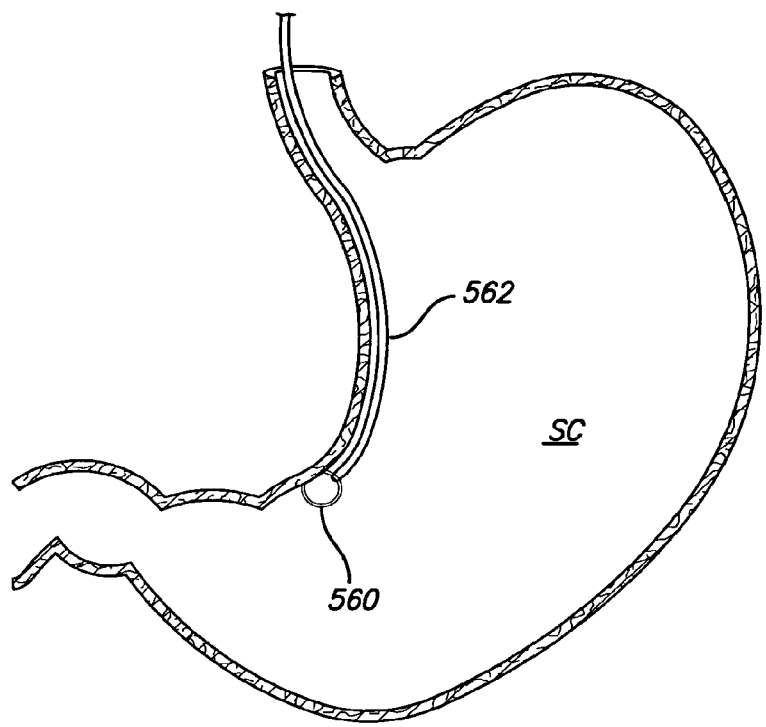
FIGS. 59 through 63 depict one embodiment of advancing a tissue treatment device to the stomach using a loop attached to the lesser curve of the stomach and a wire passed through the loop.

FIG. 58 shows the retractor section, in this embodiment the bougie retractor 110, in a retracted configuration forming an arc within the stomach cavity. In this position the retractor section 20 blocks unwanted tissue or retracts unwanted tissue away from a target area so the acquisition device 300 can acquire the desired tissue for stapling without gathering unwanted folds. An antrum wire 312 also is shown to be deployed in FIG. 58. The antrum wire retracts additional stomach tissue away from the tissue treatment device. The retractor can also be maneuvered with the handle at the proximal end in any direction to adjust or move the tissue of the stomach. For example, the retractor handle can be moved proximally, distally, or rotated, thereby causing the retractor section to move and manipulate stomach tissue. Flexible endoscope 306 is shown in FIG. 58, and may be placed alongside the tissue treatment device or can be advanced through the scope tube 22 of the retraction device, underneath the tissue treatment device and then around the side of the bougie retractor 110 to view the working area. In an embodiment where the tissue treatment device includes vacuum capabilities to suction desired stomach tissue into the members of the tissue treatment device, the retractors deployed within the stomach cavity will also block unwanted additional tissue from being suctioned to the tissue treatment device. Once the tissue treatment device has performed its therapy to the stomach wall (for example forming a staple line), the endoscope can be removed to allow additional space to remove the tissue treatment device along with the retraction device. The procedure of performing a therapy to the stomach wall with a tissue treatment device can be found in the previously incorporated references, such as U.S. patent application Ser. No. 10/188,547. Before removing the retraction device from the stomach cavity, the antrum retractor is returned to its insertion position within a groove disposed on the body of the bougie retractor, and the bougie retractor is returned to its straight delivery position so that it can be withdrawn proximally through the esophagus.

The method described above can incorporate any of the retraction devices and methods disclosed above. For instance, the stomach may also be insufflated to provide a better viewing area with the endoscope and to assist in retracting any unwanted tissue. Further, a balloon may also be inflated on the back side of the retractor section to move additional tissue away from the tissue treatment device. All of the embodiments disclosed are advantageous because they retract stomach tissue by moving, pushing, pulling, or twisting unwanted tissue away from the tissue treatment device, allowing the tissue treatment device to more easily acquire target tissue and perform a therapy thereon.

Figure 60:
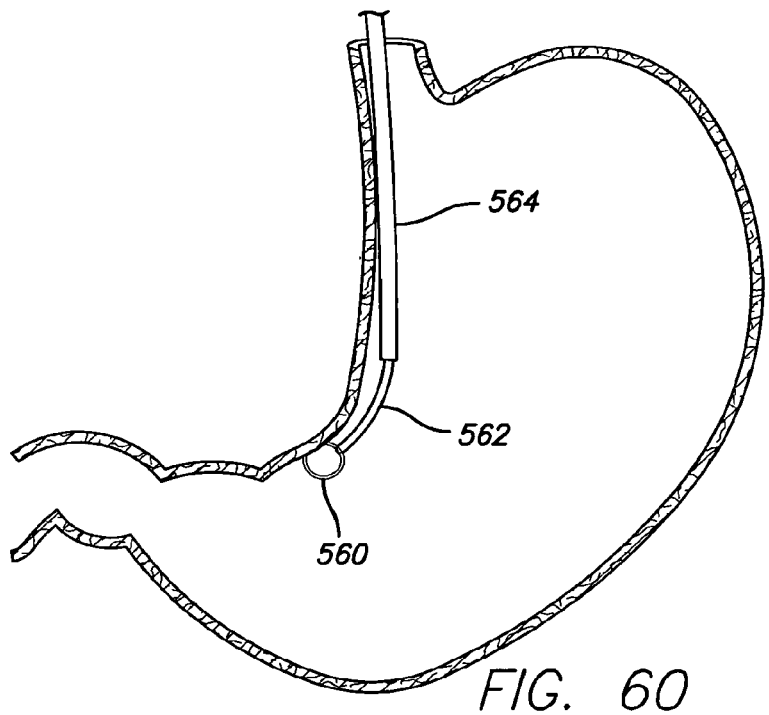
Figure 61:
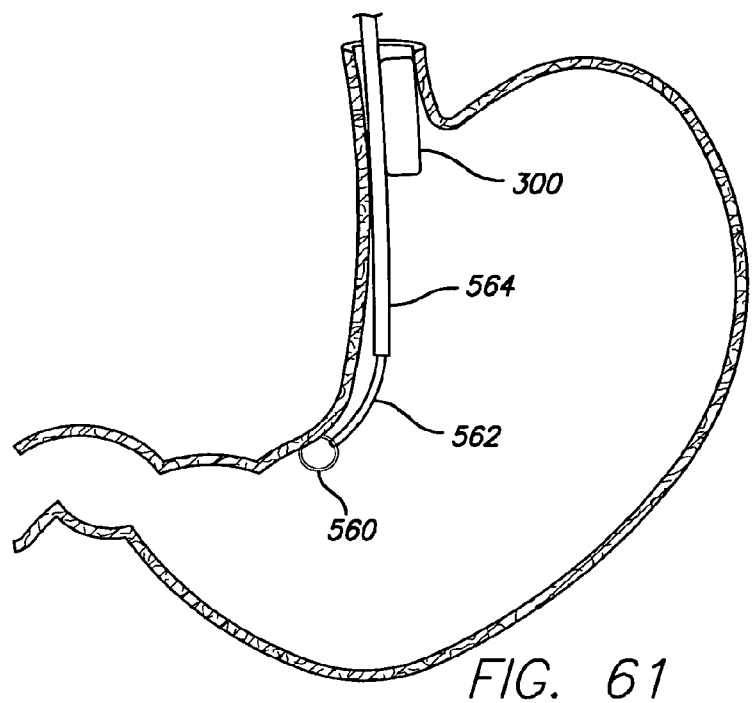
Figure 62:
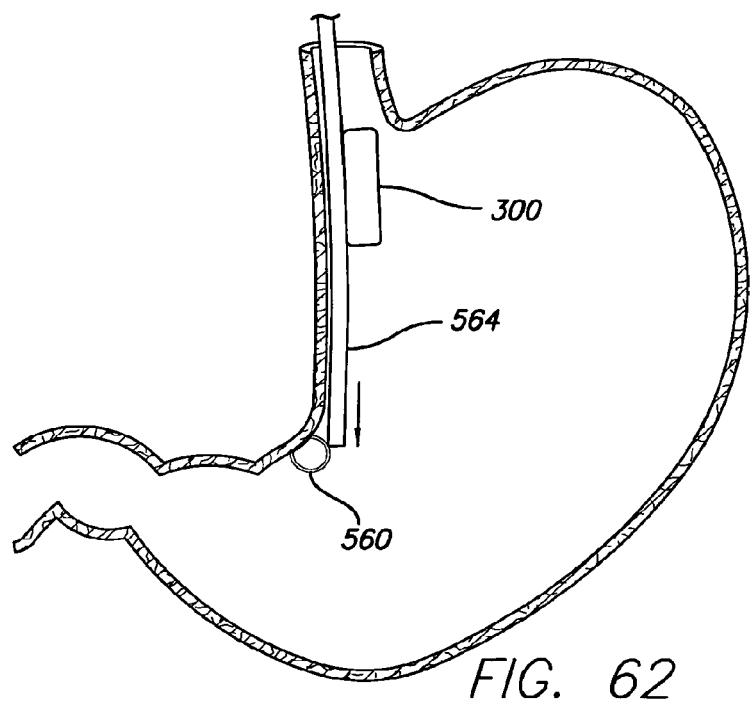
Figure 63:
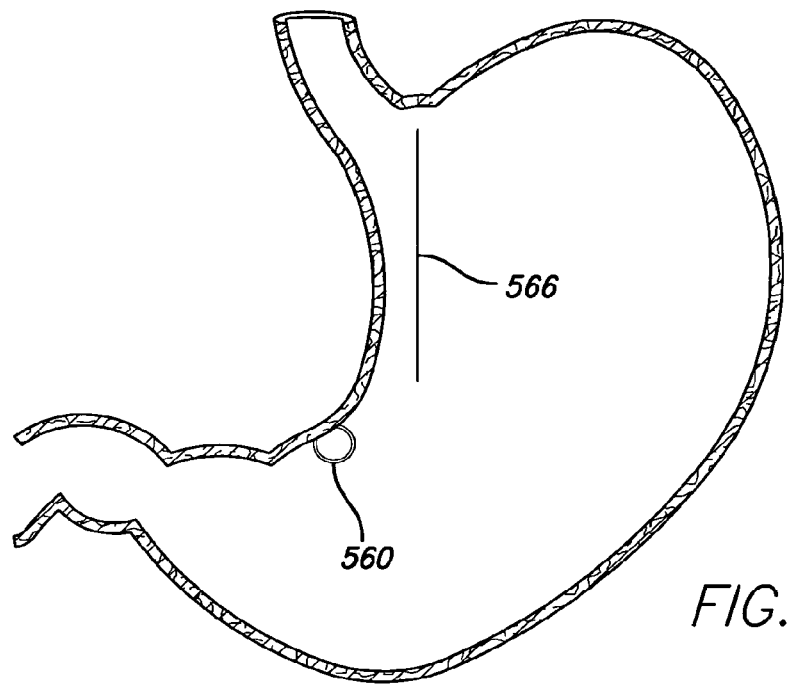

FIGS. 59-63 show an embodiment of advancing the tissue treatment device to the stomach. In this embodiment, at the beginning of the tissue treatment procedure, a loop 560, such as a suture or a ring, is attached to the lesser curve of the stomach near the incisura. This loop can be attached directly to the stomach tissue, or a single fold may be formed by a tissue treatment device and the loop may then be attached to the single fold. A wire or thread 562 (suture) is passed through the loop 560 with both ends of the wire 562 extending outside of the patient's mouth. With the wire acting like a guide wire similar to the function of a guide wire in an "over the wire" cardiac catheter procedure as is known in the art, a guide tube 564 is advanced over the wire, as shown in FIG. 60, until its distal end abuts the loop. The guide tube should be flexible enough to maneuver through the esophagus to the stomach, but still having enough stiffness to apply an axial force to the loop. With the guide tube in place, the tissue treatment device 300 is advanced along the guide tube to the stomach cavity, as shown in FIG. 61. Although not shown in the figures, the tissue treatment device may be integrated with a retraction device as well. Referring now to FIG. 62, once the tissue treatment device is in position within the stomach, an axial force may be applied over the guide tube by pushing the guide tube and pulling or holding steady the ends of the wire outside of the body. This action axially retracts the lesser curve of the stomach to remove any wrinkles along the lesser curve and assists in ensuring proper placement of the treatment device 300 against the lesser curve of the stomach. Tissue is then acquired by the tissue treatment device and a staple line 566 is formed within the stomach. After the procedure is completed, the tissue treatment device, guide tube, and wire are removed, leaving the loop and the staple line in the stomach as shown in FIG. 63. The advantages of this embodiment are that the loop provides an anchor point for retracting the stomach tissue and helps align the tissue treatment device along the lesser curve.

In another embodiment, at the beginning of the tissue treatment procedure, a loop is attached to the lesser curve of the stomach near the incisura as described above. A retraction device or tube can then be passed down into the stomach and a distal end of the retraction device or tube can be attached to the loop by a hook, grasper or similar device. Once attached to the loop, the retraction device or tube can be pushed distally to axially retract the stomach tissue. A tissue treatment device may then be passed along the retraction device or tube in order to help align the tissue treatment device with the lesser curve. This embodiment also provides an anchor point for retracting the stomach tissue and helps align the tissue treatment device along the lesser curve. Alternatively, instead of placing a ring or staple, the wire may employ small graspers at the distal end and may simply grasp tissue and be used in the method described above. Following the procedure, the graspers are released, and the entire wire assembly is removed from the patient.

Figure 64:
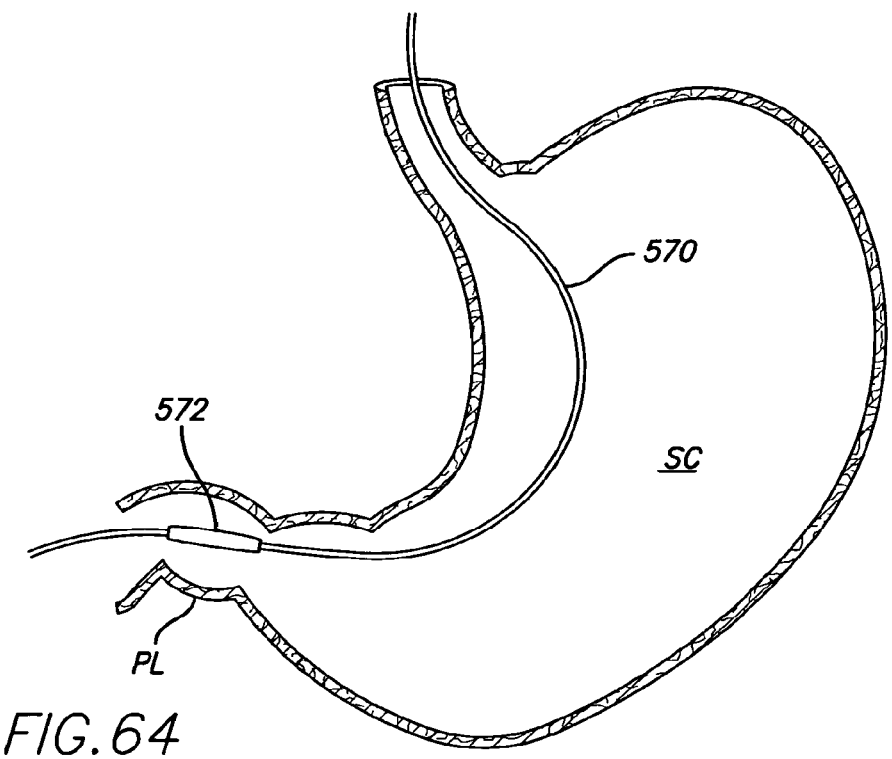
FIGS. 64 through 66 depict another embodiment of advancing a tissue treatment device to the stomach using a balloon catheter.
Figure 65:
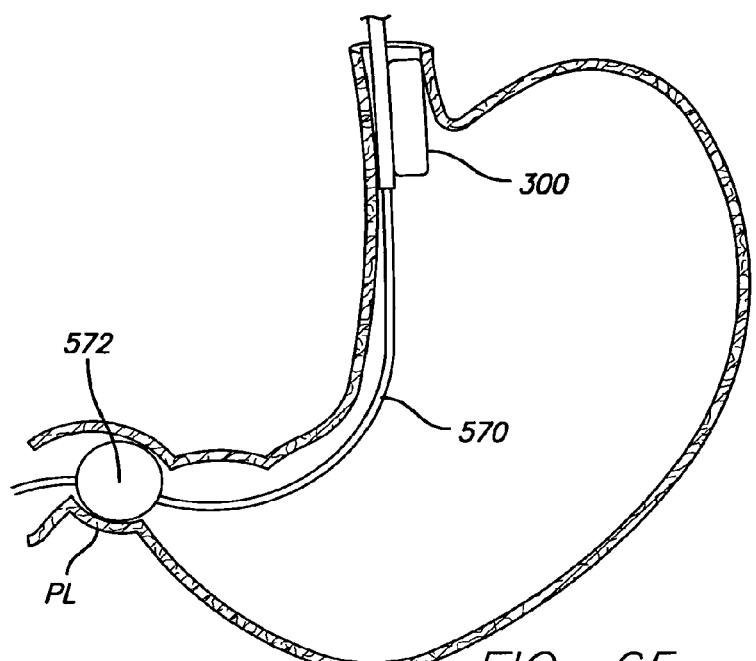
Figure 66:
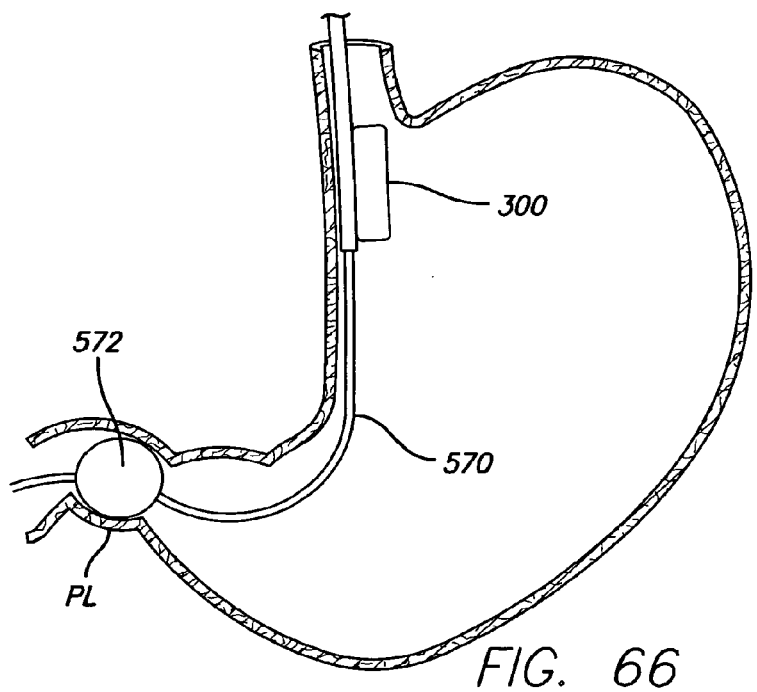

In yet another embodiment shown in FIG. 64, a catheter or wire 570 having a balloon 572 disposed at the distal end thereof can be advanced into the stomach until the balloon is oriented in the region of the pylorus ("PL"). The balloon is then temporarily inflated, thereby anchoring itself within the pylorus and holding the wire in the stomach as shown in FIG. 65. The tissue treatment device 300 is then advanced over the wire to the appropriate location as shown in FIG. 66. Upon completion of the procedure, the balloon is deflated and the wire/balloon assembly is removed.

Figure 67:
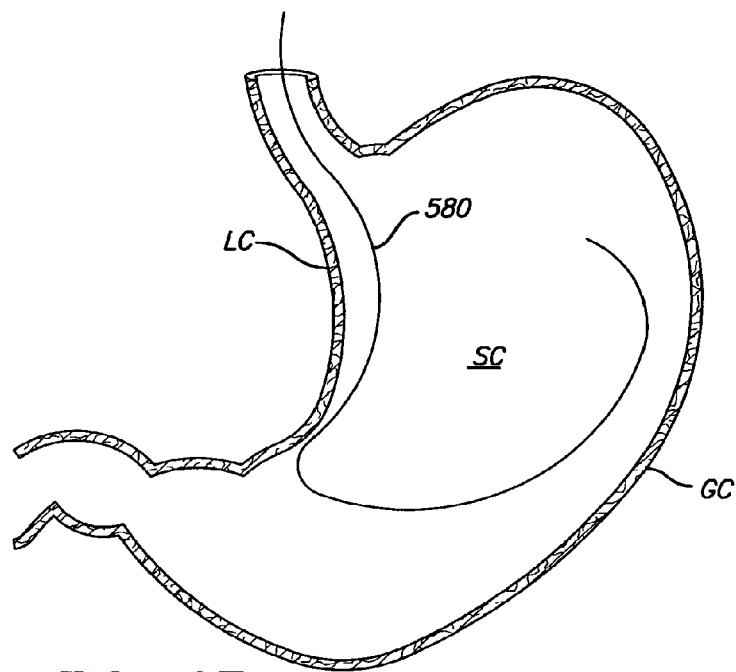
FIGS. 67 through 72 depict yet another embodiment of advancing a tissue treatment device to the stomach using a stiffening wire.
Figure 68:
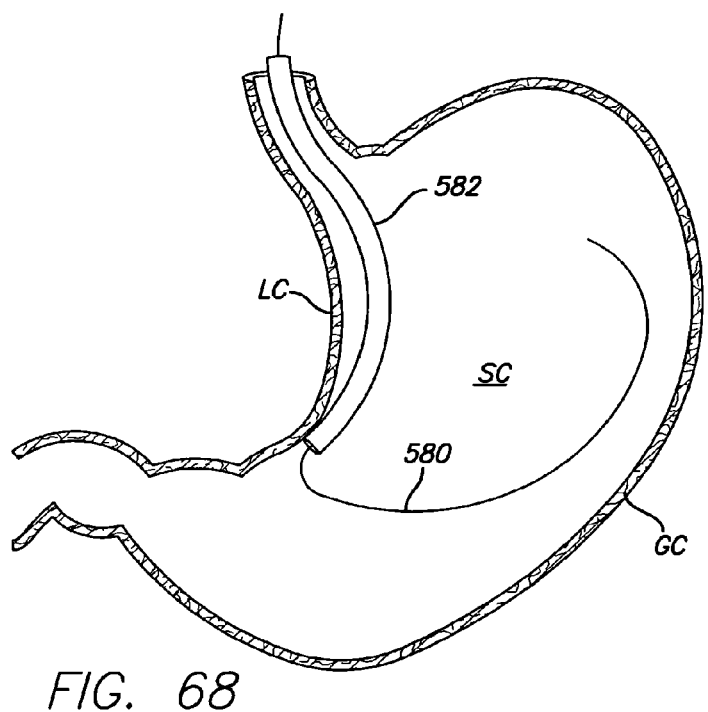
Figure 69:
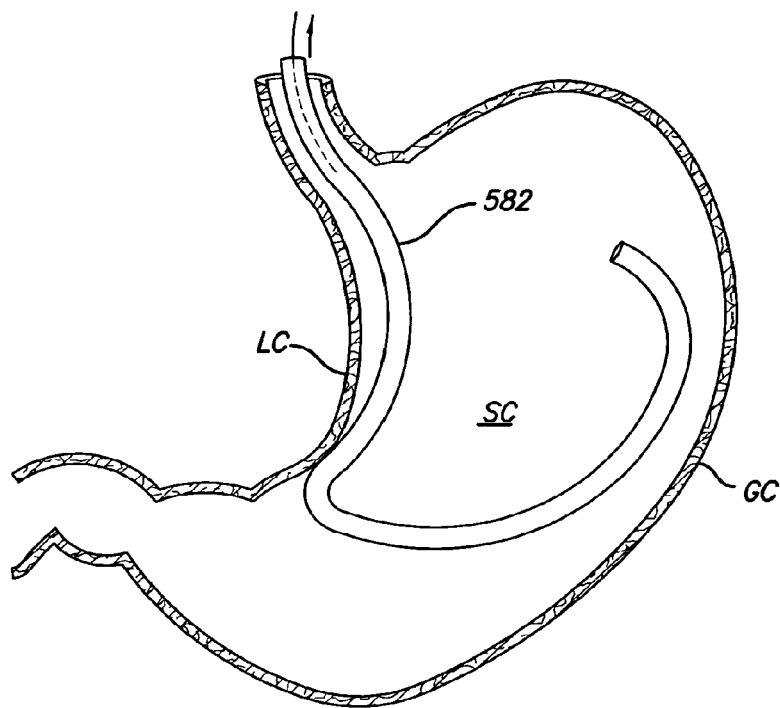

Another embodiment of advancing the tissue treatment device to the stomach is shown in FIGS. 67 through 72. As shown in FIG. 67, a guide wire 580 is positioned into the stomach cavity transorally so that it follows the curvature of the greater curve of the stomach. Any standard gastric guide wire may be used, such as a guide wire from Savory Gillard having a diameter of 0.035 inch. Once the guide wire is in place, a guide catheter tube 582 having a central lumen is placed over the guide wire and routed into the stomach cavity as shown in FIG. 68. Next, the guide wire is removed from the body of the patient, leaving behind the guide catheter tube as shown in FIG. 69. In one embodiment, the guide catheter tube is configured to be resilient and once positioned in the stomach cavity acts like a retractor by moving unwanted stomach tissue away from a target area. Further, the tissue treatment device could then be placed over the resilient guide catheter tube and advanced into the stomach cavity. This embodiment is advantageous because the resilient guide catheter tube acts like a retractor of tissue in the body of the stomach and also would position the treatment device optimally along the lesser curve.

Figure 70:
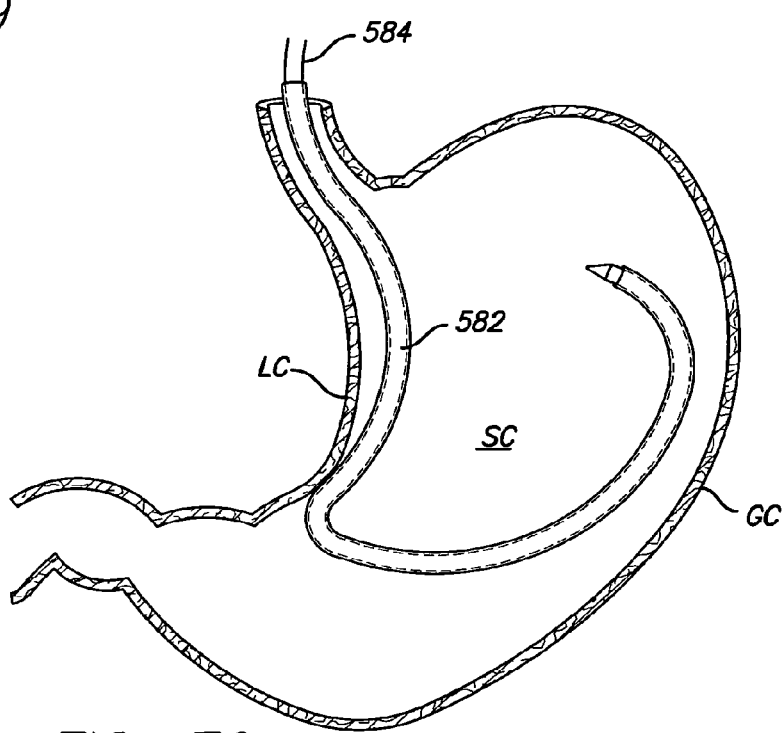
Figure 71:
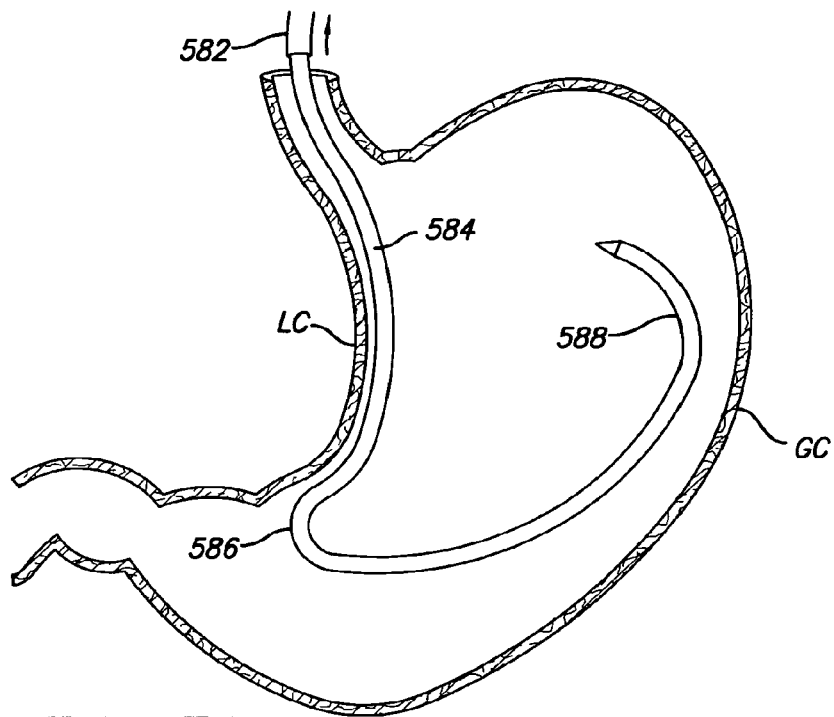
Figure 72:
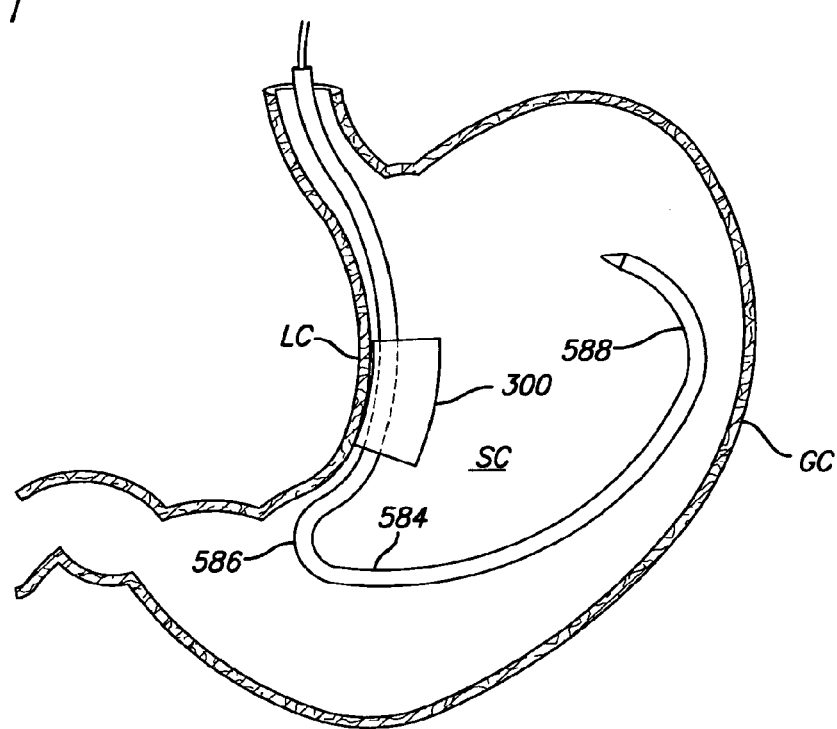

However, in another embodiment, a stiffening wire 584 or mandrel is placed down the lumen of the guide catheter tube 582 to the stomach cavity as shown in FIG. 70. The stiffening wire has a preformed retraction shape, and may be made from any shapeable material, such as a resilient plastic, nitinol, or spring steel. In this embodiment, the guide catheter tube would need to be robust enough to contain the preformed stiffening wire as it is placed down the esophagus. Following the insertion of the stiffening wire, the guide catheter tube is removed from the patient's body leaving the pre-shaped stiffening wire in place within the stomach cavity as shown in FIG. 71. As shown in this figure, the stiffening wire includes a bend 586 toward the lesser curve of the stomach. This allows the tissue treatment device to be directed closer to the lesser curve of the stomach when it is placed within the stomach. Also, the stiffening wire includes a hook shape 588 at its distal end that helps to retract tissue in the stomach cavity. It has also been contemplated that the distal end of the stiffening wire could form a full loop to retract unwanted tissue from the tissue treatment device. Referring next to FIG. 72, the tissue treatment device is then inserted into the stomach cavity over the stiffening wire, where the bend of the stiffening wire directs the tissue treatment device toward the lesser curve of the stomach. After the procedure is completed, the tissue treatment device is removed from the patient's body followed by the stiffening wire. To remove the stiffening wire, a retrieval catheter may be positioned over the stiffening wire and then both the retrieval catheter and stiffening wire may be removed from the patient.

Extra-Gastric Retractors

Figure 73:
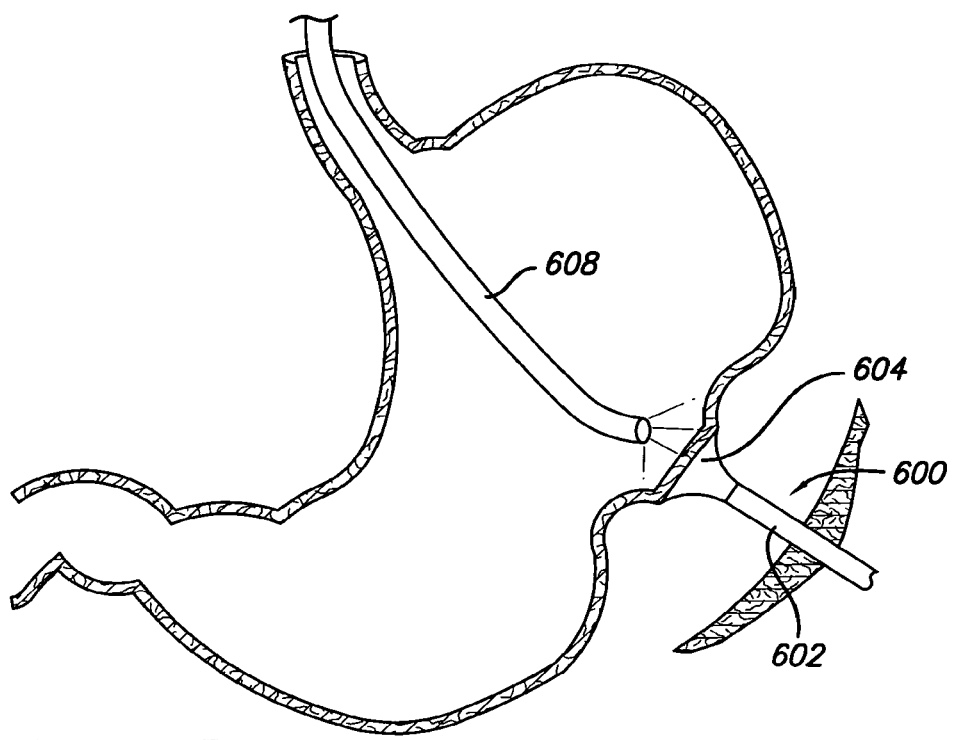
FIG. 73 depicts an embodiment of an extra-gastric retractor including a laparoscopic tube that attaches to the outer surface of the stomach.

Laparoscopically placed retractors may also be used in conjunction with a therapeutic device, such as a tissue treatment device 300, and may even be used with a tissue treatment device integrated with a retractor device that is placed transorally within the stomach. These extra-gastric retractors are able to manipulate the stomach from outside of the stomach cavity to better position the stomach for tissue acquisition from within the stomach. Referring now to FIG. 73, a laparoscopic tube 600 is shown having a tube body 602 and an anchoring end 604 at the distal end of the tube body. The anchoring end may be in communication with a vacuum to suction onto the outer stomach wall, or it may any number of devices, such as a suction cup, graspers, or snare. Once the anchoring end is attached to the stomach, the laparoscopic tube can be moved in any direction to manipulate the position of the stomach. In one embodiment as shown in FIG. 73, an endoscope 608 placed within the stomach transorally may also be used to view the inner stomach wall to provide the physician with assistance in maneuvering the stomach. Once the stomach has been moved to a desired position, the laparoscopic tube may be secured in place outside of the patient.

Figure 74:
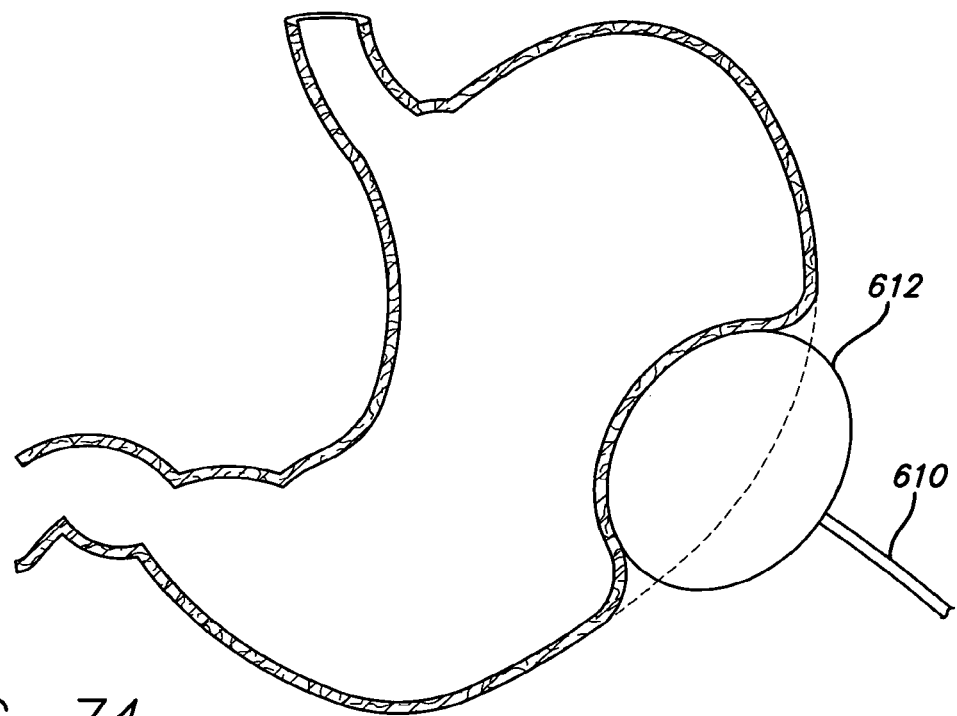
FIG. 74 depicts a balloon catheter maneuvering the stomach by pressing against the outer surface of the stomach.

Another embodiment of an extra-gastric retractor is shown in FIG. 74, and includes a catheter 610 or balloon introducer with a balloon 612 attached to the distal end. In this embodiment the catheter is advanced through the abdominal wall with the balloon deflated at the distal end. Once the distal end of the catheter is positioned near the stomach, the balloon is inflated to maneuver the stomach into a desired position.

Figure 75:
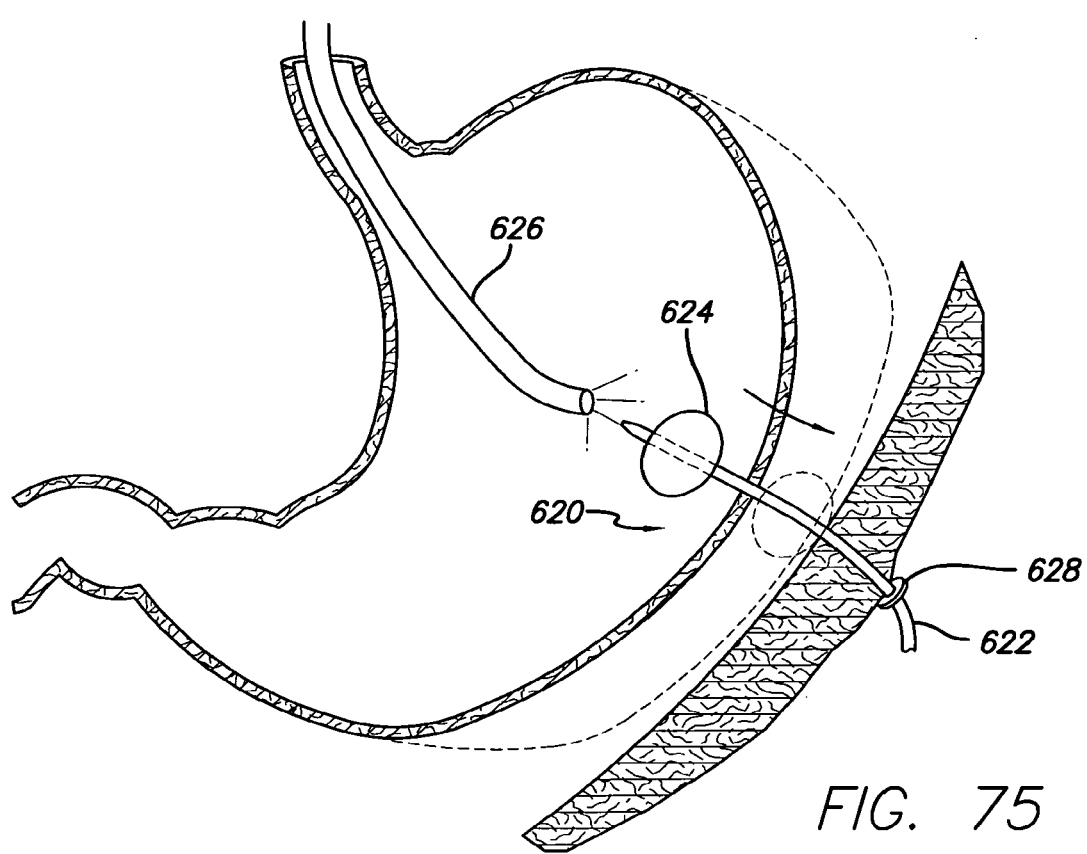
FIG. 75 depicts another embodiment of an extra-gastric retractor including a percutaneous endoscopic gastrostomy ("PEG") tube.

Referring to FIG. 75, yet another embodiment of an extra-gastric retractor shown. In this embodiment, a percutaneous endoscopic gastrostomy ("PEG") tube 620 is shown having a flexible tube 622 and a balloon 624 disposed at the distal end of the flexible tube. This procedure can also be used with an endoscope 626 that is positioned within the stomach transorally, so the physician can see the stomach wall through which the PEG tube will pass. In operation, the PEG tube passes through skin of the abdomen, through a very small incision, and into the stomach. Once the distal end of the flexible tube is within the stomach cavity, the balloon is inflated at the distal end of the tube within the stomach. The stomach may then be maneuvered by pulling the flexible tube in the proximal direction to stretch or move the stomach wall. In one embodiment, a locking or tensioning mechanism 628 can be used outside of the body to hold the flexible tube and the stomach in a new position. By repositioning the stomach, tissue may more easily be acquired by a tissue treatment device positioned within the stomach transorally. In a similar placement method, the "PEG" tube incision and tube may be used to pass an endoscope up to or into the stomach to assist the user with transoral placement of the treatment devices, or just to have general visualization of the treatment region.

Additional Integrated Retractor

When performing a therapy with a tissue treatment device as described above to form a staple line within the stomach cavity, the jaws (cartridge member and anvil member) of the tissue treatment device are opened and a vacuum is created to gather target tissue into separate vacuum pods included in each jaw of the tissue treatment device. An optional septum located between the pods acts to separate the targeted tissue into the separate vacuum pods so that a single region of tissue is in one pod and another single region of tissue is in the other pod. The optional septum is then removed and the jaws are closed to staple these two regions of tissue together. However, tissue that is supposed to be gathered by one vacuum pod may jump or cross over the septum and enter into the vacuum pod of the other jaw, which prevents the tissue treatment device from forming a continuous staple line without gaps or holes. To prevent the tissue from crossing over from one vacuum pod to the other, a barrier may be placed between the pods that is separate from the optional septum. In one embodiment, an extension or attachment can be connected to the septum so that when the tissue treatment device is in a closed configuration, the extension will be contained within the tissue treatment device, and in an opened configuration, the extension can be extended above the septum to prevent tissue cross over.

Figure 77:
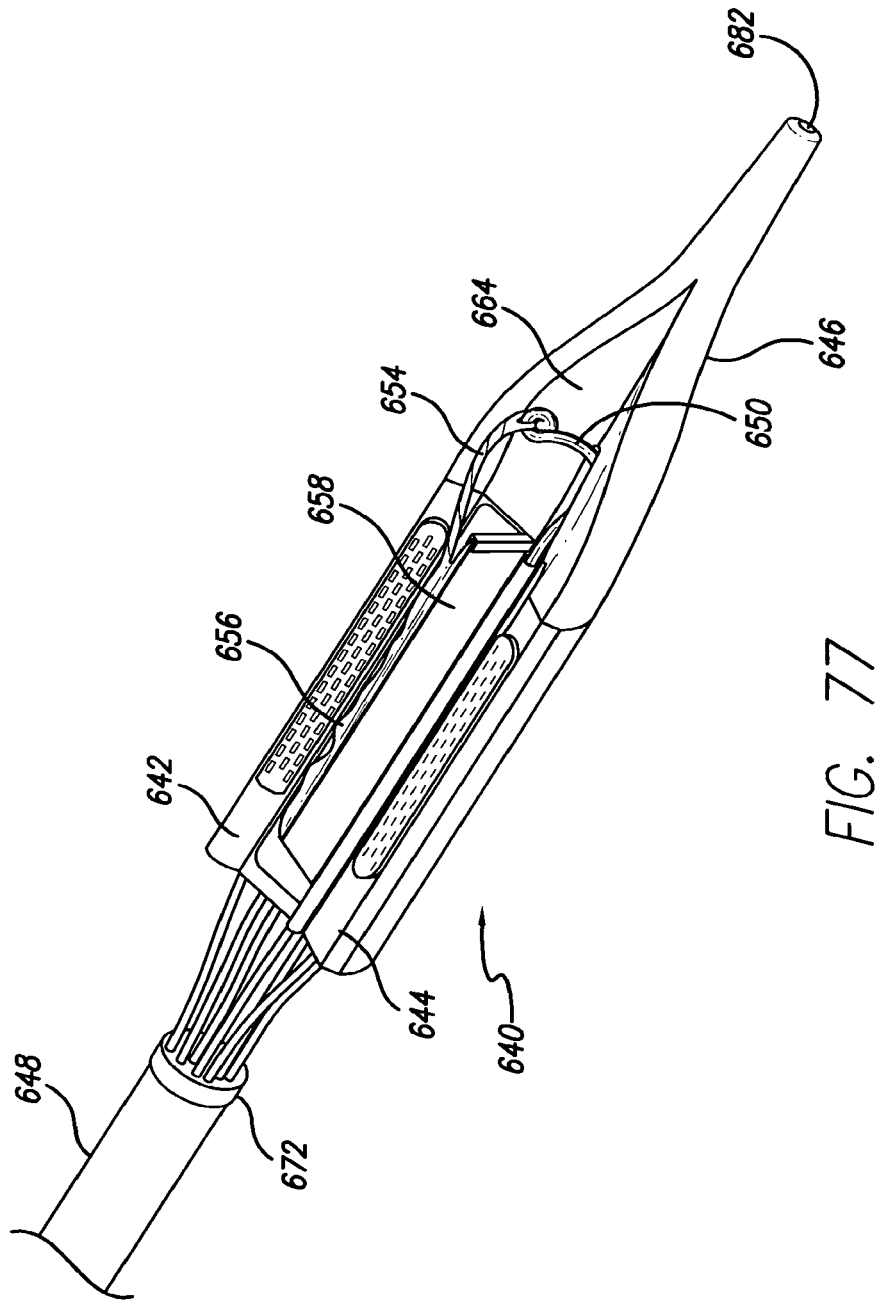
FIG. 77 depicts the tissue treatment device of FIG. 76 with jaws opened.
Figure 78:
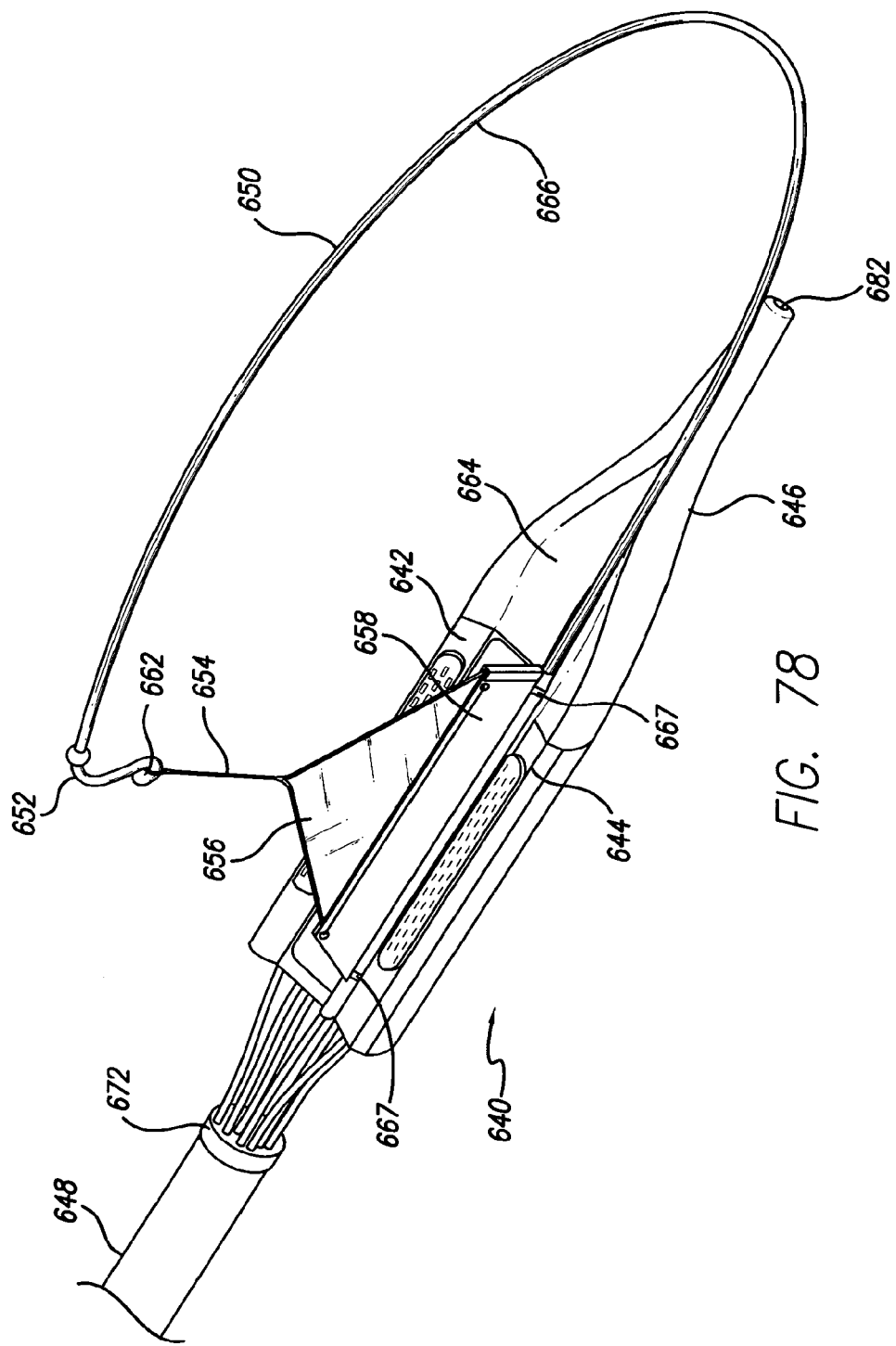
FIG. 78 depicts the tissue treatment device of FIG. 77 with the jaws opened and a retractor wire and sail in an extended configuration.
Figure 79:
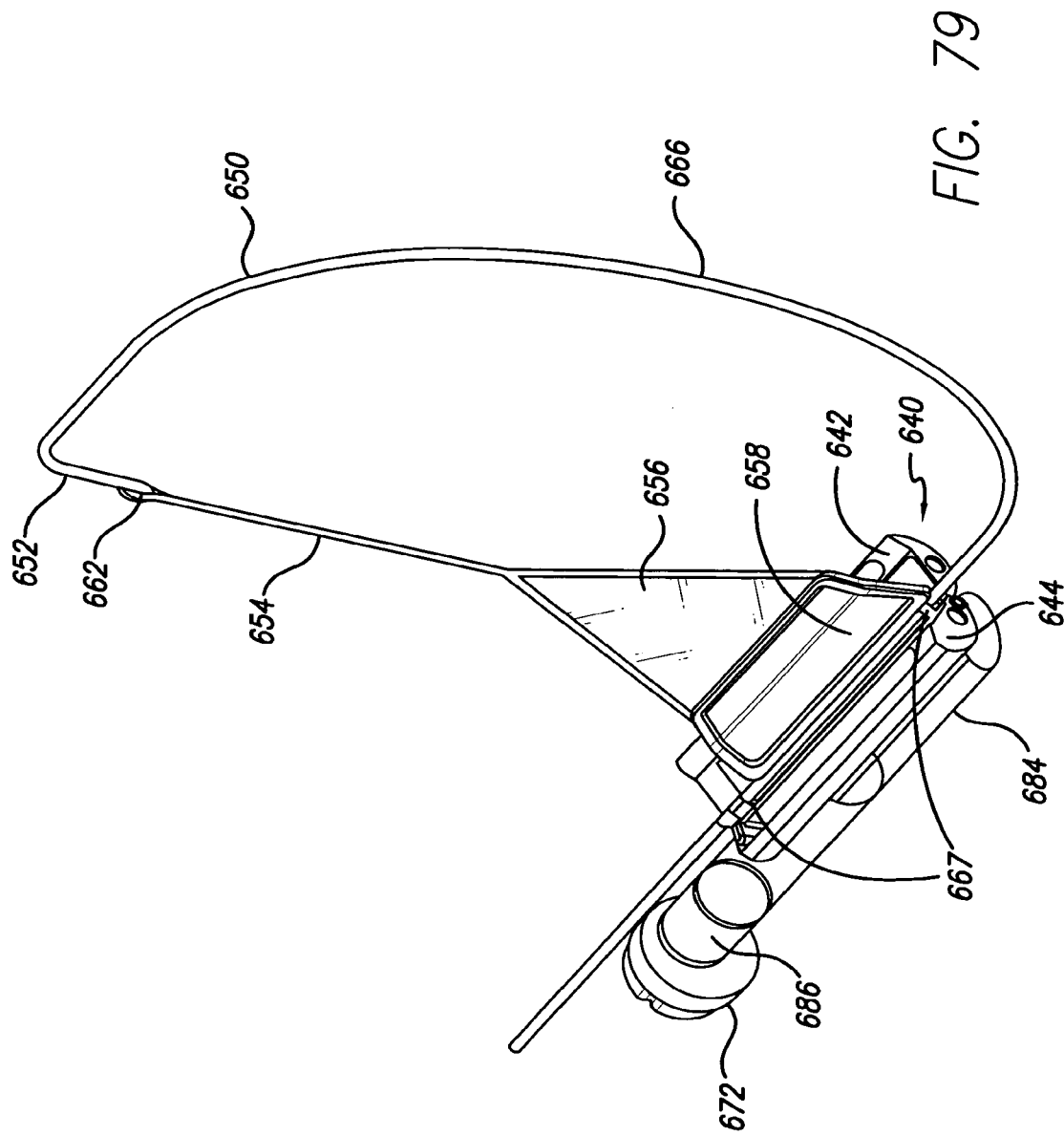
FIG. 79 depicts the tissue treatment device of FIG. 78 with the distal tip removed to better show a shroud which is connected to the backside of the tissue treatment device to provide a passageway for the endoscope.

Referring now to FIGS. 76 through 80, another embodiment of a tissue treatment device 640 is shown that has been modified to include a retractor and a barrier that is extendible between the separate pods of the tissue treatment device. The barrier may be flexible so that it can move between and an extended configuration and a collapsible configuration. The tissue treatment device is similar to the device disclosed in U.S. patent application Ser. No. 10/707,303, which already has been incorporated by reference, and includes a cartridge member 642 and an anvil member 644. An atraumatic tip attached to the distal end of the tissue treatment device in this embodiment is a split flexible tip 646. The tissue treatment device is attached to the distal end of a scope tube or flexible shaft 648 for placement within the stomach cavity. In this embodiment, the retractor is a retractor wire 650. In this embodiment, a first end 652 of the retractor wire is attached to a tether wire 654, which is attached to a sail 656 and an optional septum 658 located between the cartridge member and anvil member. In an alternative embodiment, the sail element may serve the function of the septum in its extended form. With the first end of the retractor wire secured to the tissue treatment device, the remaining portion of the retractor wire loops around the tissue treatment device and through the flexible shaft 648, where the second end (not shown) is positioned at the proximal end of the device. In the extended configuration as shown in FIG. 79, the sail acts as a barrier and ensures that the target tissue enters the appropriate vacuum pod without crossing over into the other vacuum pod. It has also been contemplated that that the tissue treatment device does not include a septum, and the sail 656 is attached between the jaws of the tissue treatment device. In this embodiment, the sail may be attached to the tissue treatment device with a pin or wire through hinges between the jaws.

Figure 76:
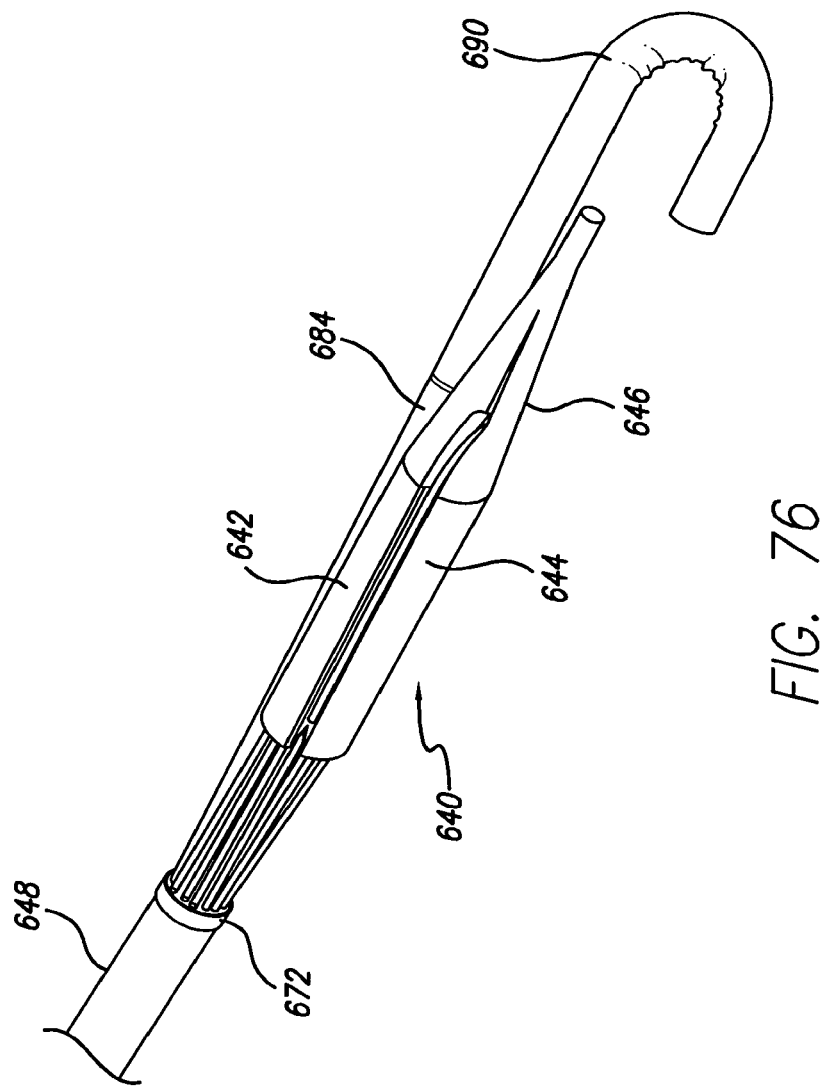
FIG. 76 depicts another embodiment of an integrated tissue treatment device in a delivery configuration with an endoscope alongside.

In one embodiment, the first end 652 of the retractor wire 650 is curved and includes an eyelet 662. An end of the tether 654 is attached to the eyelet of the retractor wire, and the tether may be secured to the septum 658. When the tissue treatment device 640 is in the delivery position with the jaws closed as shown in FIG. 76, the first end of the wire retractor rests inside a gap or slit 664 formed in the split flexible tip 646, as best shown in FIG. 77. In use, when the tissue treatment device is positioned within the stomach, the wire retractor is extended by pushing the wire distally, and since the first end of the wire is anchored to the tissue treatment device via the tether, excess wire forms a loop 666 or other space occupying geometry within the stomach cavity. In this retraction position as shown in FIG. 79, the loop formed with the wire retractor pushes or blocks unwanted tissue away from the tissue treatment device. In some embodiments, the wire retractor is a nitinol wire, although any material, including stainless steel or a comparatively stiff polymer, can be used to form the wire structure.

Figure 80:
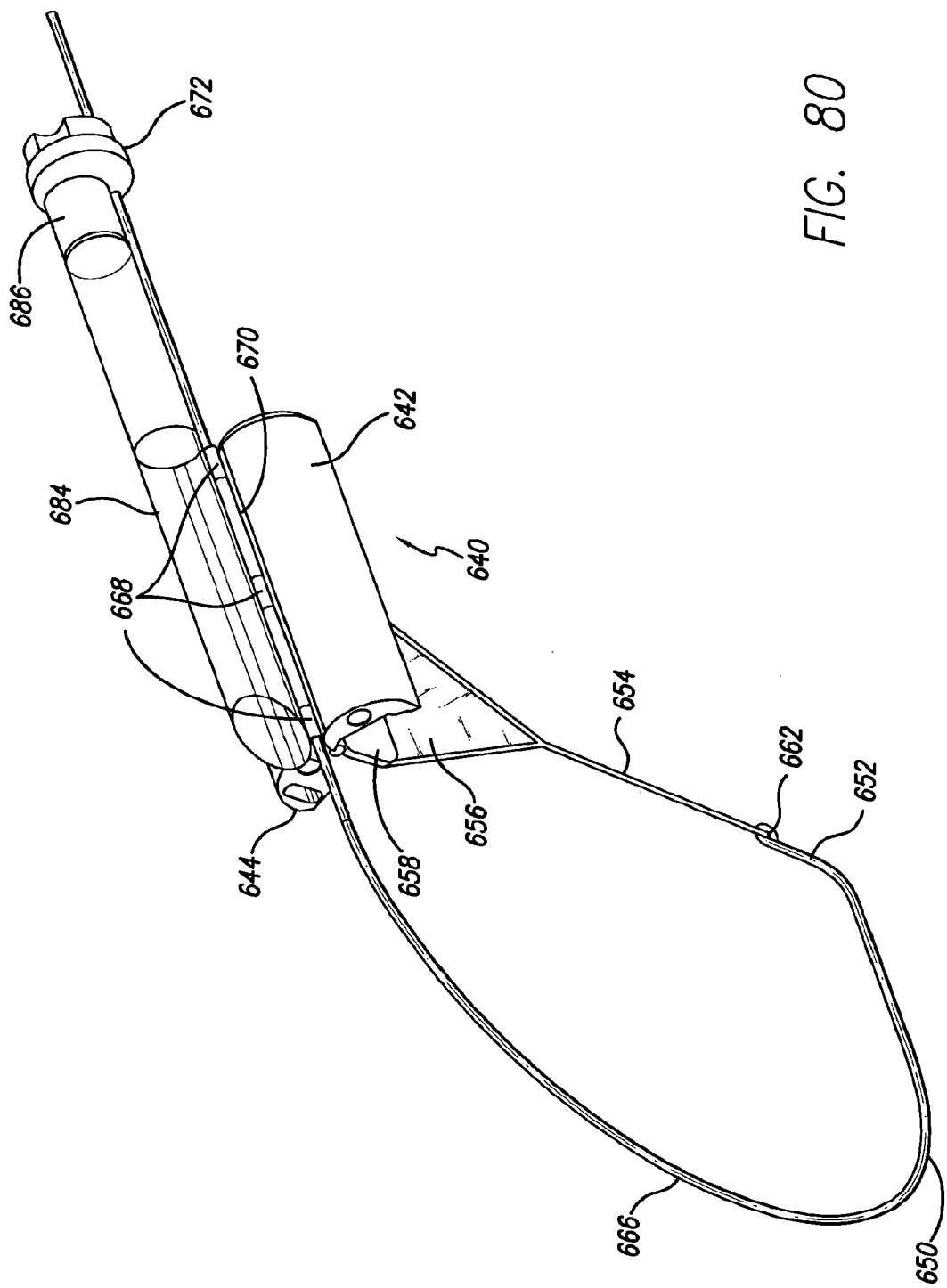
FIG. 80 depicts a backside perspective view of the tissue treatment device of FIG. 79.

The retractor wire 650 extends through the flexible shaft 648 to the tissue treatment device 640, where the retractor wire passes through hinges or tabs attached to the tissue treatment device. In one embodiment, the retractor wire passes through the hollow hinge pins 667 located between the jaws of the tissue treatment device and underneath the septum 658 as shown in FIG. 79. The split flexible tip has been removed from FIG. 79 to better show the position of the retractor wire. In another embodiment, the retractor wire passes through tabs 668 of a strap 670 that is attached to the backside of the tissue treatment device as shown in FIG. 80. Instead of tabs, the strap may form a continuous lumen that the retractor wire may pass through. FIG. 80 also shows the wire retractor passing through an end ring 672 that is attached to the distal end of the flexible shaft. In the delivery configuration for this embodiment, the first end 652 of the retractor wire is positioned within the gap 664 of the split flexible tip 646 by entering the split flexible tip through the gap 664 which extends through the tip at its proximal end. Also, in the extended configuration, the retractor wire will extend through the gap of the flexible tip.

In one embodiment, the shape of the sail 656 is defined by the tether wire 654, which as shown in FIG. 79 is a triangle, although other shapes may be used such as circular, oval, or any polygonal shape. The sail may be formed of a polyimide tape that is wrapped around and secured to the tether. Other materials that can be used to form the sail include any plastic or flexible material, for example the sail element may be cut from a sheet of material, or molded to a particular shape. Such other materials may include polyester (e.g., DACRON® from E. I. du Pont de Nemours and Company, Wilmington, DE), polypropylene, polytetrafluoroethylene (PTFE), expanded PTFE (ePTFE), nylon, or silicone. In one embodiment, the tether is also secured through holes of the septum 658, however, the sail may be attached directly to the septum. It has also been contemplated that the first end 652 of the retractor wire 650 is directly attached to the sail without the use of a tether wire. In the delivery or closed configuration, the sail folds up and is positioned within the jaws of the tissue treatment device as shown in FIG. 76. Once the tissue treatment device opens and the retractor wire is extended, the sail is raised above the septum as is shown in FIG. 79. As stated previously, the tissue treatment device may not include the septum, and the sail is then connected between the jaws of the tissue treatment, where it provides the function of the septum element.

As shown in FIGS. 76-78, the split flexible tip 646 includes a cylindrical body 674 with a proximal end 676 and a distal end 678. There is also a split or gap 664 formed at the proximal end of the cylindrical body that is wide enough to house the first end 652 of the retractor wire 650 when the device is in its delivery configuration. The cylindrical body includes a progressive taper towards the distal end for insertion through the esophagus. Also, the cylindrical body may include a guide wire lumen 682 so the device can track along a guide wire that has been positioned within the stomach cavity. The proximal end 676 of the split flexible tip can be attached to the distal end of the tissue treatment device with an adhesive and/or mechanically with pins or a post extending from the tissue treatment device. If adhesive is used, the surface area at the cross section of the proximal end of the cylindrical body 674 should be nearly as large as the surface area of the ends of the jaws (cartridge member 642 and anvil member 644). The split or gap 664 allows the split flexible tip to open (see FIG. 77) and close (see FIG. 76) along with the tissue treatment device, and provides a space for the retractor wire to extend through. In order for the split flexible tip to open and close and be atraumatic to the tissue of the patient, it is formed of a flexible elastomeric material, such as silicone rubber.

As best shown in FIG. 80, an endoscope shroud or sleeve 684 is attached to the backside of the tissue treatment device 640. The shroud provides a passageway for the endoscope, and the passageway starts from the distal end of the flexible shaft and ends along the backside of the tissue treatment device. It is possible for the shroud to extend any length along the tissue treatment device, and it may even extend past the distal end of the tissue treatment device. In one embodiment, the tubular structure of the shroud is formed by layers of tape, such as polyimide tape, although any flexible material may be used to form the shroud. In some embodiments the shroud may be molded or formed over a mandrel and then attached to the tissue treatment device. It is preferable that the shroud surface be smooth and flexible to be atraumatic to the esophagus when passed to the treatment area. A collar 686 is attached to an end ring 672 located at the distal end of the flexible shaft 648, and the proximal end of the shroud is attached to or wrapped around the collar as shown in FIG. 80. The shroud is then attached to the tissue treatment device by being wrapped around the same strap 670 that provides guidance for the retractor wire in some embodiments. In other embodiments that do not include the strap 670, the shroud can be adhesively attached to the tissue treatment device. In use, the shroud tube lumen directs the endoscope around the jaws of the tissue treatment device for viewing the procedure. Also, the shroud 684 cradles or contains the endoscope to prevent the scope from torqueing or "wowing" in a variety of directions that may impact the resulting geometry of the gastroplasty or pouch.

In operation, the tissue treatment device 640 is positioned within the stomach cavity in its delivery position as shown in FIG. 76. Once in position within the stomach cavity, the jaws of the tissue treatment device are opened as shown in FIG. 77. During the procedure, a flexible endoscope 690 can be inserted along the flexible shaft 648 and through the shroud 684 to view the tissue treatment device and target area of the tissue. The retractor wire 650 is pushed distally through the tissue treatment device, and because the first end 652 is attached to the sail tether 654, a loop of excess wire 666 is formed as shown in FIG. 78. This action also raises the sail as the retractor wire pulls the tether away from the tissue treatment device. In this position the retractor wire blocks or retracts unwanted tissue away from a target area so the tissue treatment device can acquire the desired tissue for stapling without gathering unwanted folds. Targeted tissue is drawn into vacuum pods located in the cartridge member 642 and the anvil member 644 when a vacuum is created, and the extended sail acts as a barrier to prevent tissue from crossing over from one pod to the other. This helps to ensure that the staple line formed in the stomach cavity is continuous without any gaps or holes.

Figure 81:
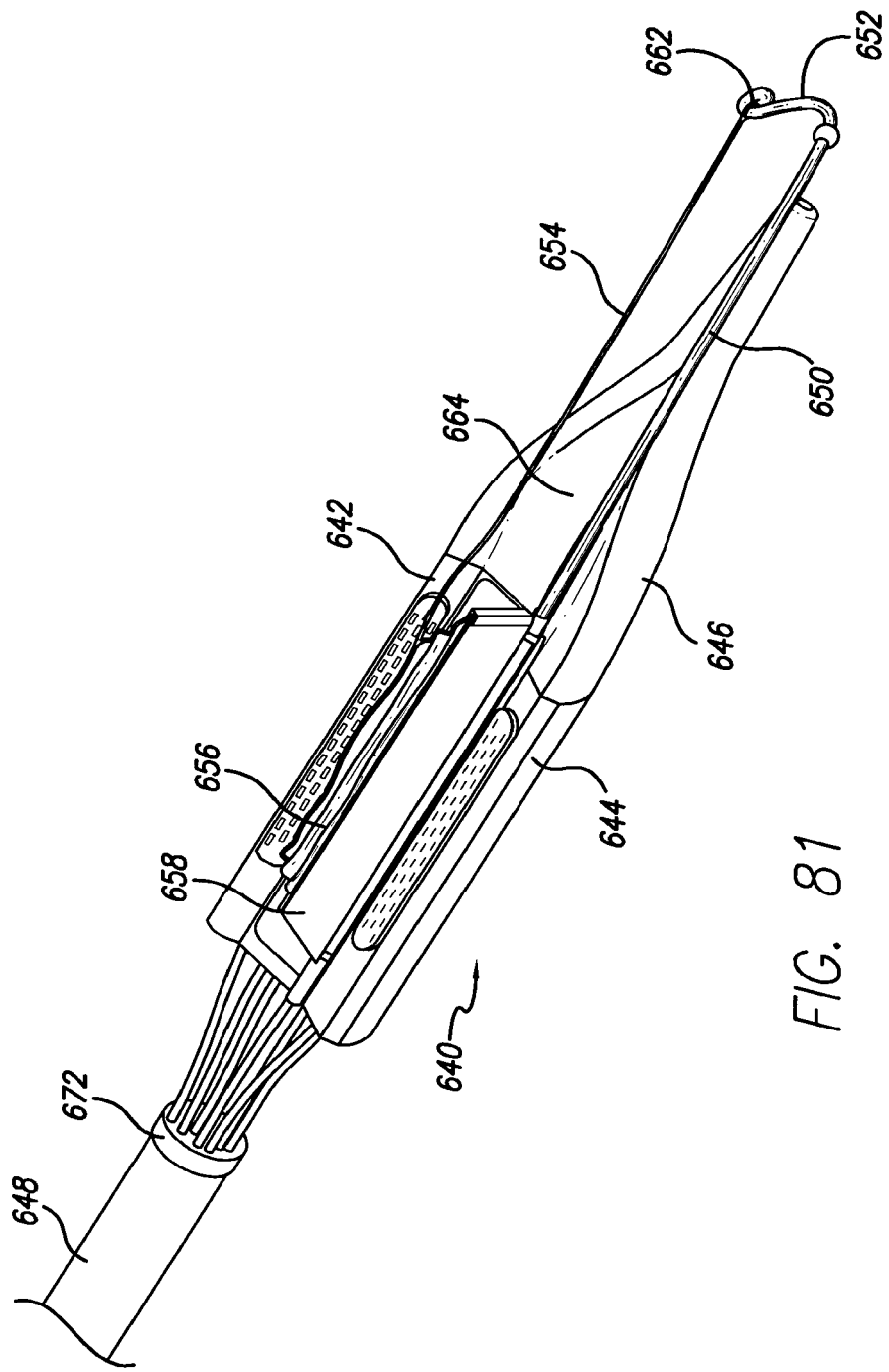
FIG. 81 depicts the tissue treatment device of FIG. 78 with the retractor wire and sail lowered before removal of a septum between the jaws of the tissue treatment device.
Figure 82:
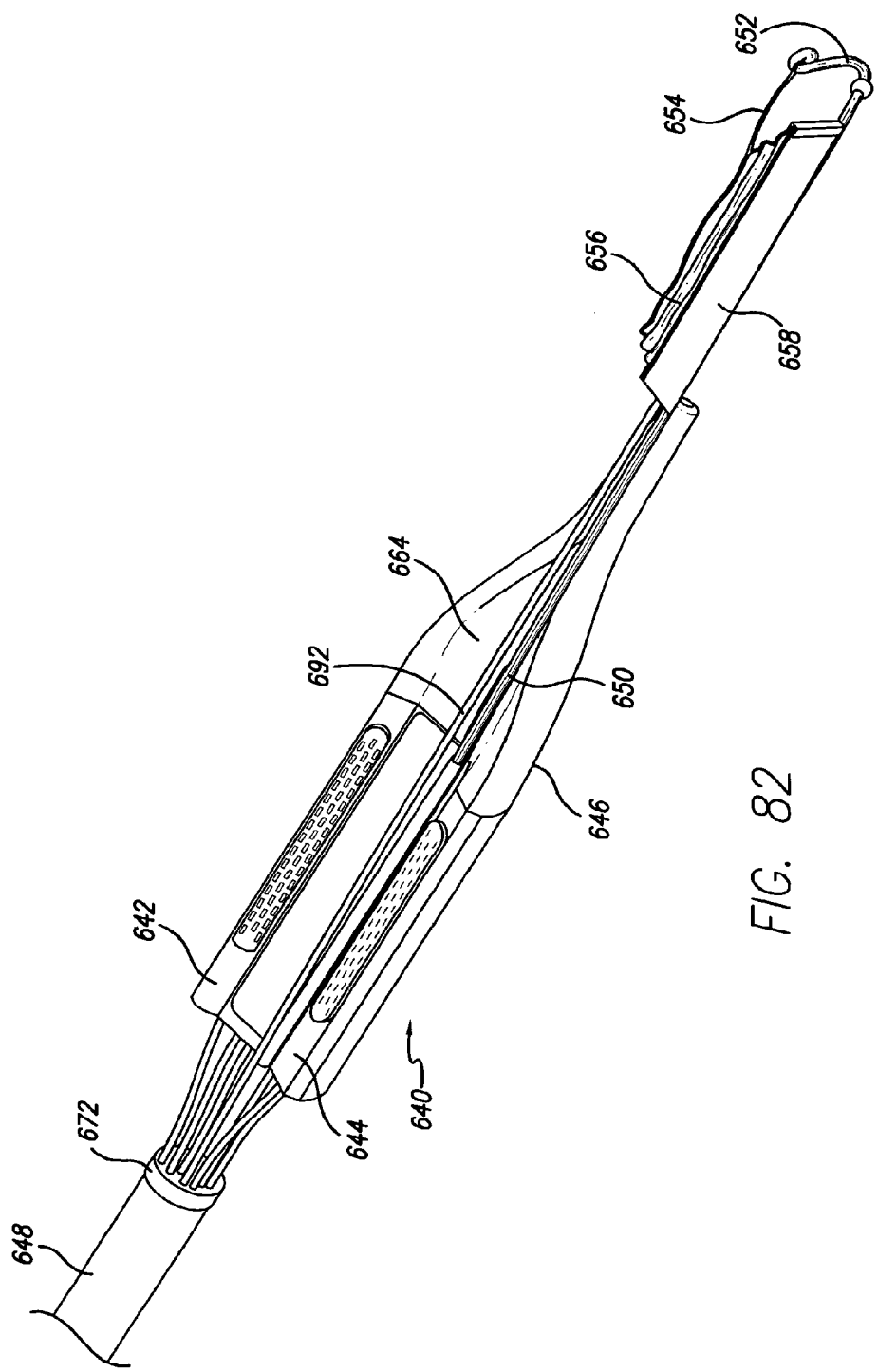
FIG. 82 depicts the tissue treatment device of FIG. 81 with septum and sail removed from the jaws of the tissue treatment device.

After acquiring separate regions of tissue in each vacuum pod of the tissue treatment device 640, the septum 658 and sail 656 need to be removed before the two regions of tissue are stapled together. First, the retractor wire 650 is pulled proximally until its distal end is near the split flexible tip 646 and the sail 656 is collapsed as shown in FIG. 81. Next, the septum is pushed distally away from the jaws of the tissue treatment device by a septum wire 692 as shown in FIG. 82. Once the septum is removed, the cartridge member 642 and anvil member 644 are closed together and a staple line is fired within the stomach cavity. After the stapling procedure is completed, the entire device including the endoscope is removed from the stomach cavity. The sail is flexible enough so that when it is removed from the stomach cavity, it does not cause trauma to the esophagus of the patient.

Figure 83:
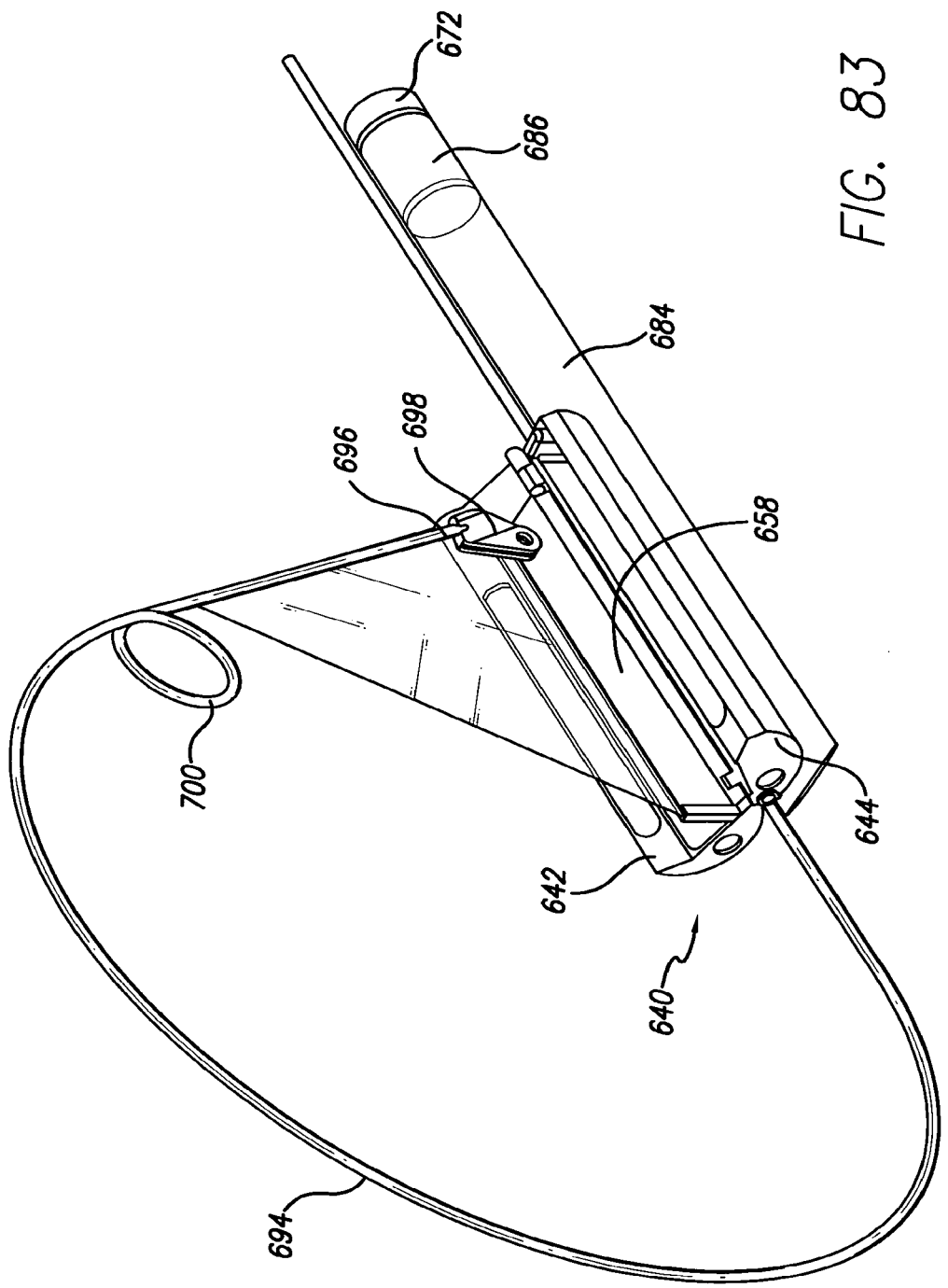
FIG. 83 depicts another embodiment of a tissue treatment device, wherein the sail is attached to the retractor wire.

In another embodiment of an integrated device, the sail 656 of the integrated device may be directly attached to a wire retractor 694 and the septum 658 as shown in FIG. 83. Although not shown in FIG. 83, the split flexible tip 646 can also be attached to the distal end of the tissue treatment device. A first end 696 of the retractor wire 694 is attached to a septum hinge 698 that is hinged to the proximal end of the septum as shown in FIG. 83. The retractor wire also includes a loop 700 that acts as a hinge to allow the retractor wire to fold into the delivery diameter, which is approximately 54 French. The loop and the septum hinge allow the sail to fold down to the top of the septum when the device is in the delivery configuration, and in this delivery configuration the loop is positioned within the split 664 of the split flexible tip 646. It has also been contemplated that the loop of the wire can be replaced with a hinge. The sail, which can be a polyimide tape is attached along the distal end of the retractor wire, below the loop and to the first end as shown in the figure, and the sail is attached to the septum, leaving one side of the triangular shaped sail unattached. In use, the septum and sail are removed from the tissue treatment device in a similar manner as described above. Also, in another embodiment, the tissue treatment device may not include the septum and the septum hinge and sail may be connected between the jaws of the tissue treatment device.

Figure 84:
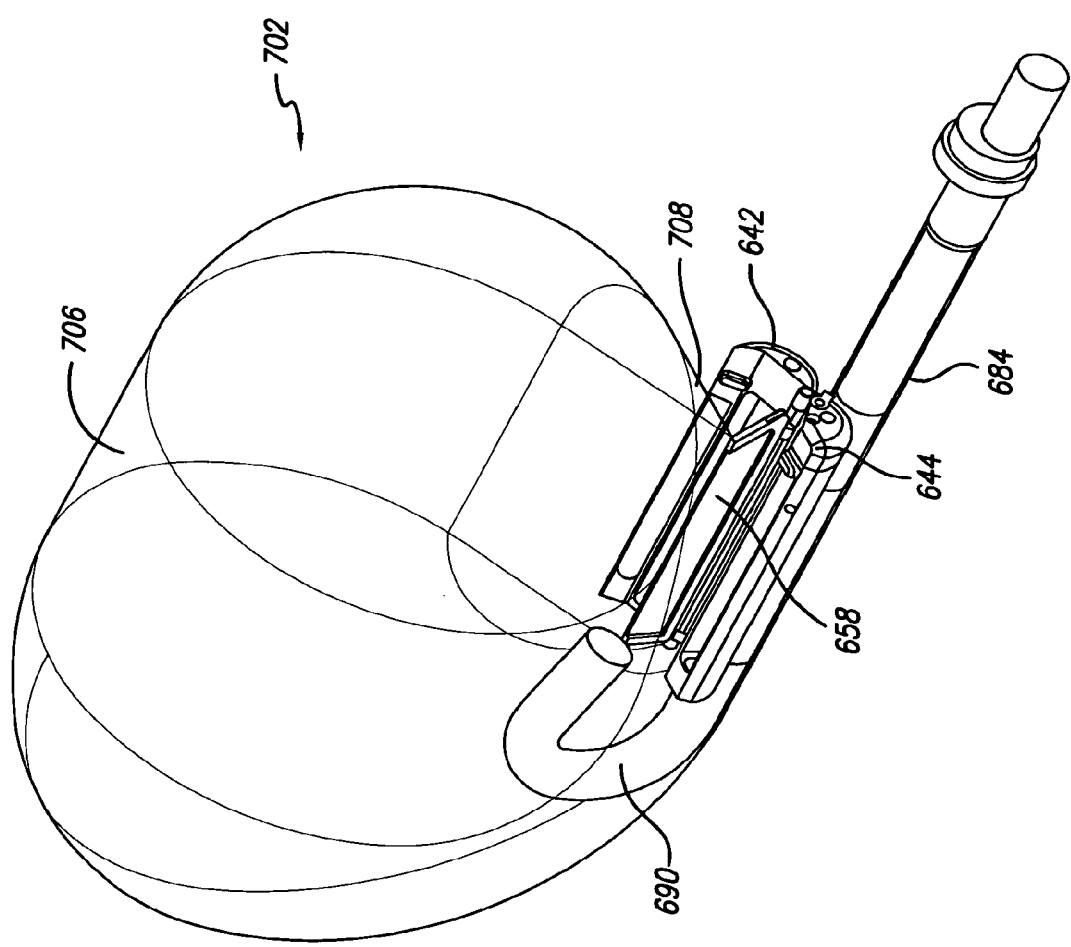
FIG. 84 depicts a perspective view of an embodiment of a tissue treatment device with a balloon retractor attached to the septum of the tissue treatment device.
Figure 85:
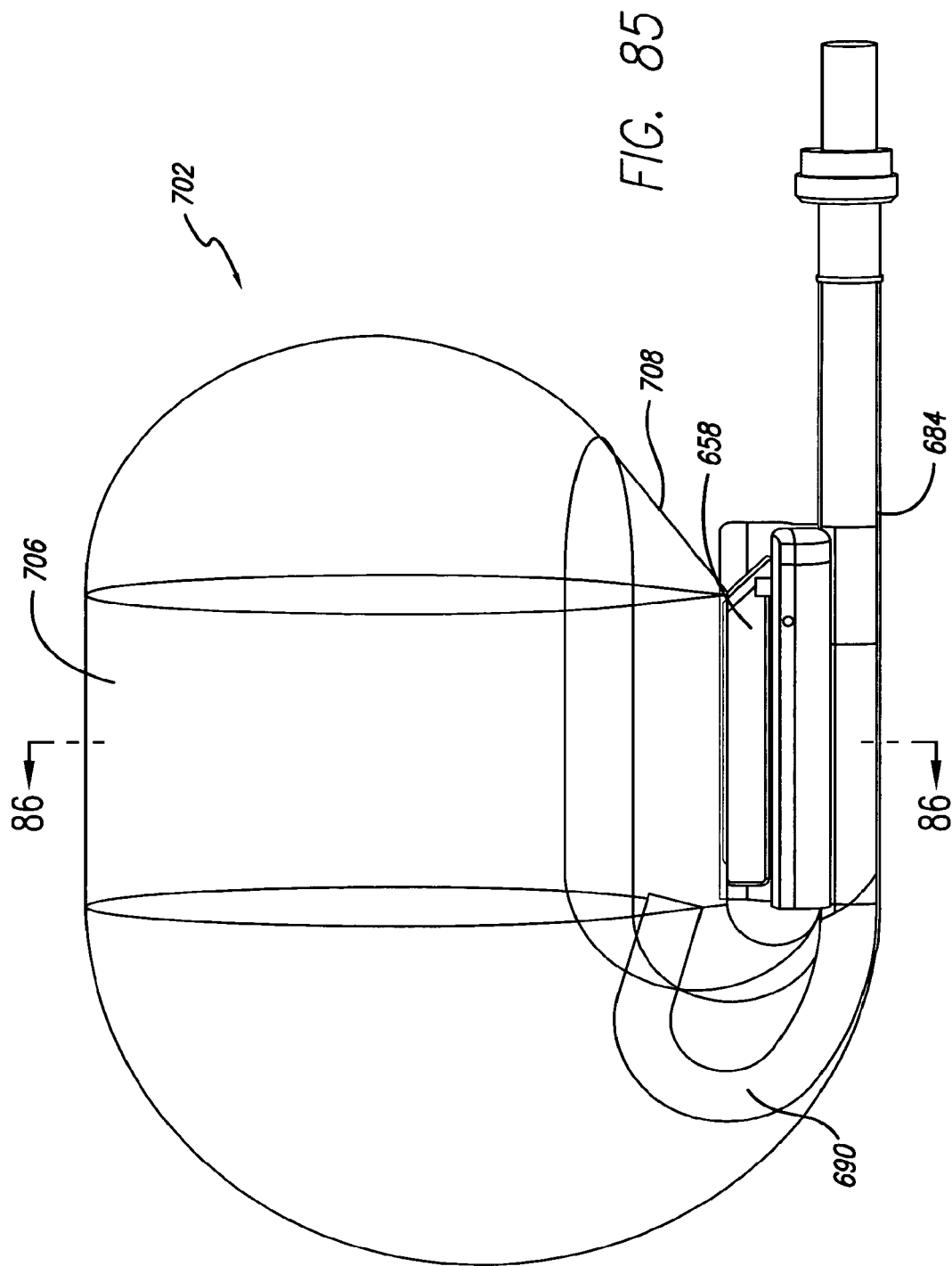
FIG. 85 depicts a side elevational view of the tissue treatment device and balloon retractor of FIG. 84.

In yet another embodiment, the wire retractor and sail are replaced with a balloon that performs the same functions, i.e., retracts unwanted tissue away from the target area and prevents tissue from crossing over from one vacuum pod to the other. An additional advantage of the balloon retractor is that it can funnel target tissue into the jaws of the tissue treatment device. A balloon retractor 702 as shown in FIGS. 84-86 includes an inlet 704 that is in fluid communication with the shroud 684, a top hemisphere 706 and a bottom hemisphere 708. The bottom hemisphere is attached to the top edge of the septum 658, preferably through an adhesive. In another embodiment, the bottom hemisphere is attached between the jaws of the tissue treatment device without the septum. The balloon may be compliant or non-compliant, and can be formed with polyester or other such material previously described above, that is transparent to allow the endoscope 690 to view the target area from within the balloon. Within the stomach cavity, the top hemisphere of the balloon will manage the fundus tissue of the stomach cavity, and its volume will occupy more stomach wall area than a wire. While the top hemisphere retracts unwanted tissue away from the tissue treatment device, the bottom hemisphere, which is attached to the septum, acts much like the sail described above to prevent tissue from crossing or jumping over the septum and into the alternative vacuum pod of the tissue treatment device.

In use, the balloon 702 is deflated and folded along the tissue treatment device 640 for delivery to the stomach cavity. Once in position, the jaws of the tissue treatment device are opened and a fluid, either air or liquid, is sent through the flexible shaft 648 or a catheter disposed within the flexible shaft to inflate the balloon through its inlet 704. In one embodiment, the inlet is directly in fluid communication with the flexible shaft or catheter, and in another embodiment the inlet is in communication with the flexible shaft or catheter by being in communication with the shroud 684. The balloon expands to retract tissue, and then a vacuum is created within pods of the cartridge member 642 and anvil member 644 to gather targeted tissue. The bottom hemisphere keeps the regions of tissue separate in each of the pods. Once the tissue is acquired, the balloon is then deflated, and then removed from between the jaws of the tissue treatment device. In an embodiment including a septum, the septum is also removed along with the balloon. The jaws of the tissue treatment device are then closed to secure the regions of tissue together with a staple line. The tissue treatment device is then removed from the stomach.

The cross-sectional shape of the balloon retractor 702 is shown in FIG. 86, and in this embodiment the balloon has a generally circular shape. Other cross-sectional shapes, such as those shown in FIGS. 87 and 88, may also be used. The balloon 710 of FIG. 87 is wedge shaped, and the formed balloon 712 of FIG. 88 has a generally oval shape. All of these shapes provide enough capture space 714 above the jaws of the tissue treatment device 640 to gather a sufficient amount of targeted tissue within the vacuum pods located within the cartridge member 642 and anvil member 644. The bottom hemisphere of the balloon can be tailored in any manner to allow for more or less volume in the capture space.

Although the present invention has been described in terms of certain preferred embodiments, other embodiments that are apparent to those of ordinary skill in the art are also within the scope of the invention. Accordingly, the scope of the invention is intended to be defined only by reference to the appended claims. While the dimensions, types of materials described herein are intended to define the parameters of the invention, they are by no means limiting and are exemplary embodiments.

We claim:

1. A device for managing tissue in an organ, comprising:
   an elongated body having a proximal end and a distal end;
   a tissue treatment device attached to the distal end of the elongated body, the tissue treatment device having a first jaw opposite a second jaw, the first jaw and the second jaw being movable between a closed position and an open position; and
   a septum including first and second blades disposed between the first jaw and the second jaw of the tissue treatment device, the first and second blades having a sheet coupled thereto that is disposed between the first jaw and the second jaw, and the first and second blades being attached to an actuator that extends through the elongated body;
   wherein proximal movement of the actuator is configured to pivot the first blade relative to the second blade such that the first blade is raised from between the first and second jaws to extend the sheet from between the first and second jaws.

2. The device for managing tissue of claim 1, wherein the sheet comprises plastic film.

3. The device for managing tissue of claim 1, wherein the actuator comprises a cable.

4. The device for managing tissue of claim 1, further comprising a pin that attaches the second blade to the tissue treatment device, the pin being releasable from the second blade so as to allow the second blade to be raised from between the first and second jaws.

5. The device for managing tissue of claim 1, wherein the tissue treatment device includes a slot formed therein that receives the first and second blades.

6. The device for managing tissue of claim 5, wherein proximal movement of the actuator is configured to pivot the first and second blades into the slot.

7. The device for managing tissue of claim 1, wherein the first and second blades of the septum are attached to a pulley, and the proximal movement of the actuator is configured to turn the pulley and raise the first and second blades.

8. The device for managing tissue of claim 1, wherein the proximal movement of the actuator is configured to pivot an end of the first blade distally relative to the tissue treatment device.

9. The device for managing tissue of claim 1, wherein first and second blades are attached to a pulley that raises the first blade from between the first and second jaws.

10. A device for managing tissue in an organ, comprising:
an elongated body having a proximal end and a distal end;
a tissue treatment device attached to the distal end of the elongated body, the tissue treatment device having a first jaw opposite a second jaw, the first jaw and the second jaw being movable between a closed position and an open position; and
a septum having at least two blades disposed between the first jaw and the second jaw of the tissue treatment device, the at least two blades each having a first end and a second end, and the at least two blades having a sheet attached thereto;
wherein the second ends of the at least two blades are attached to the tissue treatment device and the at least two blades are configured to move from a collapsed configuration in which longitudinal axes of the at least two blades are parallel to longitudinal axes of the first and second jaws, to a deployed configuration in which the first ends of the at least two blades are not directly attached to the tissue treatment device and move along an arc-shaped path.

11. The device for managing tissue of claim 10, further comprising a pin that connects at least one of the at least two blades to the tissue treatment device and that is releasable from the at least one of the at least two blades.

12. The device for managing tissue of claim 10, wherein the tissue treatment device includes a slot therein that receives the at least two blades after the at least two blades move along the arc-shaped path.

13. The device for managing tissue of claim 10, wherein a size of the sheet determines a maximum possible angle between the at least two blades when the sheet is stretched between the first and second blades.

14. A device for managing tissue in an organ, comprising:
an elongated body having a proximal end and a distal end, the elongated body being configured to extend into a patient's body with the proximal end positioned outside of the patient's body and the distal end positioned inside of the patient's body;
a first jaw opposite a second jaw, the first jaw and the second jaw being attached to the distal end of the elongated body, the first and second jaw being movable between a closed position and an open position; and
at least one blade having a first end and a second end;
wherein, when the distal end of the elongated body is positioned inside of the patient's body and when the first and second jaws are in the open position, the at least one blade is configured to pivot, in response to actuation of an actuator at the proximal end of the elongated body, from a first position, in which the at least one blade is sandwiched between the first and second jaws, to a second position, in which the at least one blade is not sandwiched between the first and second jaws;
wherein moving the at least one blade from the first position to the second position directs tissue of the patient into the first and second jaws when the first and second jaws are in the open position;
wherein, in moving from the first position to the second position, the first end of the at least one blade moves distally along an arc-shaped path about the second end of the at least one blade while the first and second jaws remain stationary relative to the elongated body;
further comprising a slot that receives the at least one blade after the at least one blade pivots about the second end thereof.

15. The device for managing tissue of claim 14, wherein the first end of the at least one blade is configured to move distally along the arc-shaped path beyond a distal end of the first jaw and a distal end of the second jaw.

16. The device for managing tissue of claim 14, wherein the actuator comprises a cable extending through the elongated body and configured to be pulled proximally to pivot the at least one blade.

17. The device for managing tissue of claim 14, wherein at least one of the first and second jaws are pivotable about a longitudinal axis of the elongated body to move between the closed and open positions.

18. The device for managing tissue of claim 14, further comprising a sheet coupled to the at least one blade;
wherein movement of the at least one blade from the first position to the second position causes the sheet to extend from between the first and second jaws.

19. The device for managing tissue of claim 14, wherein when the at least one blade is in the first position and when the at least one blade is in the second position, a longitudinal axis of the at least one blade is parallel to a longitudinal axis of the elongated body.

* * * * *